US009623262B2

(12) United States Patent
Vaziri et al.

(10) Patent No.: US 9,623,262 B2
(45) Date of Patent: Apr. 18, 2017

(54) METHODS AND SYSTEMS FOR DETERMINING THE DISTRIBUTION OF RADIATION DOSE AND RESPONSE

(71) Applicant: Rutgers, The State University of New Jersey, New Brunswick, NJ (US)

(72) Inventors: Behrooz Vaziri, Livingston, NJ (US); Han Wu, Kearny, NJ (US); Roger W. Howell, Millington, NJ (US); John M. Akudugu, Bellville (ZA); Venkata S. Neti, Branchburg, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 175 days.

(21) Appl. No.: 14/213,231

(22) Filed: Mar. 14, 2014

(65) Prior Publication Data
US 2014/0275709 A1 Sep. 18, 2014

Related U.S. Application Data

(60) Provisional application No. 61/785,146, filed on Mar. 14, 2013.

(51) Int. Cl.
*A61N 5/10* (2006.01)
(52) U.S. Cl.
CPC .................. *A61N 5/1031* (2013.01)
(58) Field of Classification Search
CPC ........ A61N 5/10; A61N 5/103; A61N 5/1031; A61N 5/1039
See application file for complete search history.

(56) References Cited

U.S. PATENT DOCUMENTS

| 6,327,490 | B1* | 12/2001 | Spetz ..................... A61N 5/103 600/427 |
| 6,699,473 | B2 | 3/2004 | Raisch et al. |
| 2012/0106703 | A1* | 5/2012 | Roy ..................... A61N 5/1042 378/65 |
| 2012/0107234 | A1 | 5/2012 | Pedersen et al. |

(Continued)

OTHER PUBLICATIONS

Li et al., "Feasibility of Eradication of Breast Cancer Cells Remaining in Postlumpectomy Cavity and Draining Lymph Nodes Following Intracavity Injection of Radioactive Immunoliposomes" Molecular Pharmaceutics, 2012, vol. 9, pp. 2513-2522.

(Continued)

*Primary Examiner* — Charles A Marmor, II
*Assistant Examiner* — Thaddeus Cox
(74) *Attorney, Agent, or Firm* — Fox Rothschild LLP

(57) ABSTRACT

A system, method and computer program product to determine radiation dose from radionuclides used to treat a patient in need thereof. The present invention allows users to visualize and understand the impact of radionuclide choice, distribution of activity in the cell, distribution of activity among the cells, cell dimensions, cell separation distance, cluster size, and radiobiological response parameters on the capacity to kill populations of cells. All of these parameters can play a substantial role in determining the surviving fraction of cells. Accordingly, this system, method and computer program product can assist in designing treatment plans for therapeutic radiopharmaceuticals suited to individual needs.

6 Claims, 31 Drawing Sheets

(56) References Cited

U.S. PATENT DOCUMENTS

2012/0148491 A1* 6/2012 Akudugu ........... G01N 33/5008
424/1.65
2013/0079581 A1* 3/2013 Agamaite ............ A61N 5/1027
600/4
2013/0123567 A1* 5/2013 Agamaite ............ A61N 5/1007
600/4

OTHER PUBLICATIONS

Goddu et al., "Cellular Dosimetry: Absorbed Fractions for Monoenergetic Electron and Alpha Particle Sources and S-Values for Radionuclides Uniformly Distributed in Different Cell Compartments," J. Nucl Med, 1994, vol. 35, pp. 303-316.

Goddu et al., "Multicellular Dosimetry for Micrometastases: Dependence of Self-Dose Versus Cross-Dose to Cell Nuclei on Type and Energy of Radiation and Subcellular Distribution of Radionuclides," J Nucl Med, 1994, vol. 35, 521-530.

Akudugen and Howell, "A Method to Predict Response of Cell Populations to Cocktails of Chemotherapautics and Radiopharmacauticals: Validation With Daunomycin, Doxorubisin, and the Alpha Particle Emitter (210)Po," Nucl Med Biol, Oct. 2012, vol. 39, No. 7, pp. 954-961.

Rajon et al., "Lognormal Distribution of Cellular Uptake of Radioactivity: Monte Carlo Simulation of Irradiation and Cell Killing in 3-Dimensional Populations in Carbon Scaffolds," J Nucl Med, 2011, vol. 52, pp. 926-933.

* cited by examiner

STEP 1

Flow cytometry
measurement of
drug uptake $I_i$

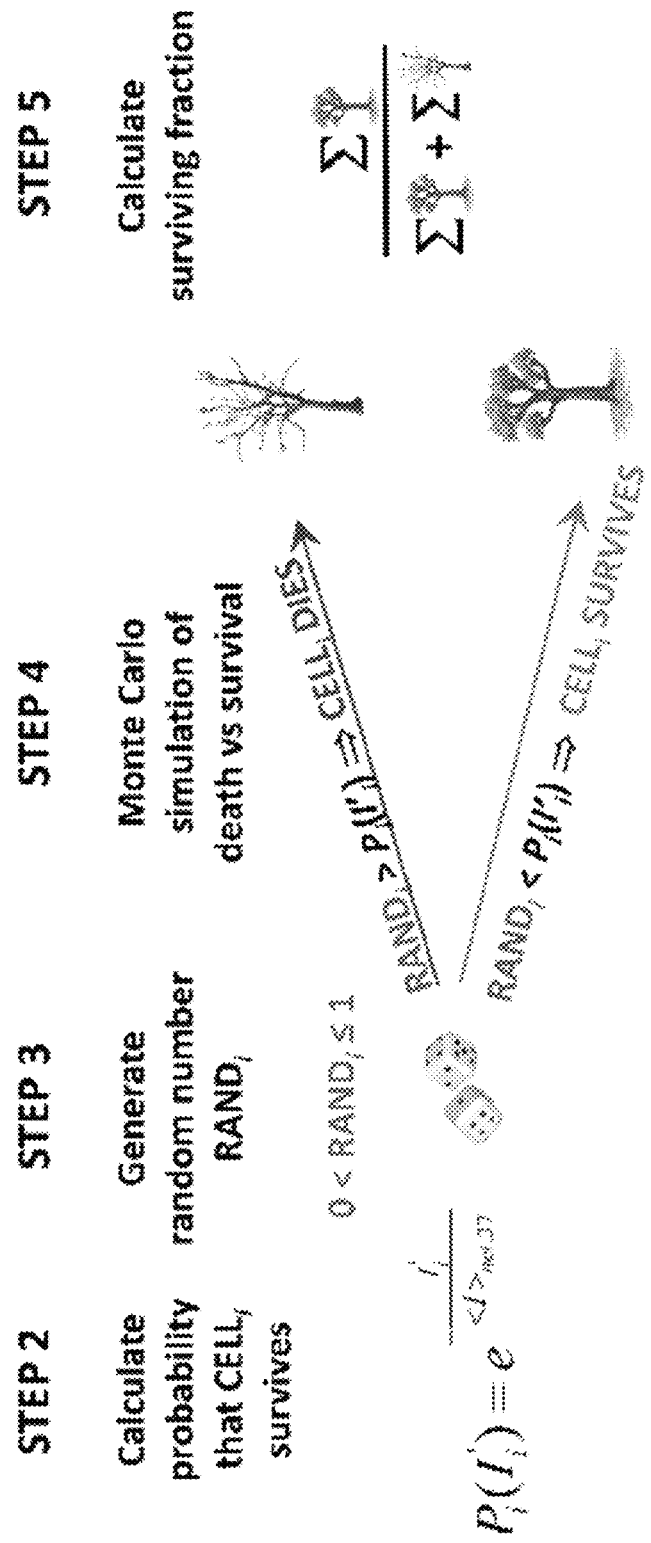
FIGURE 5 - Continued

STEP 1

Flow cytometry measurement of drug uptake $I_i$

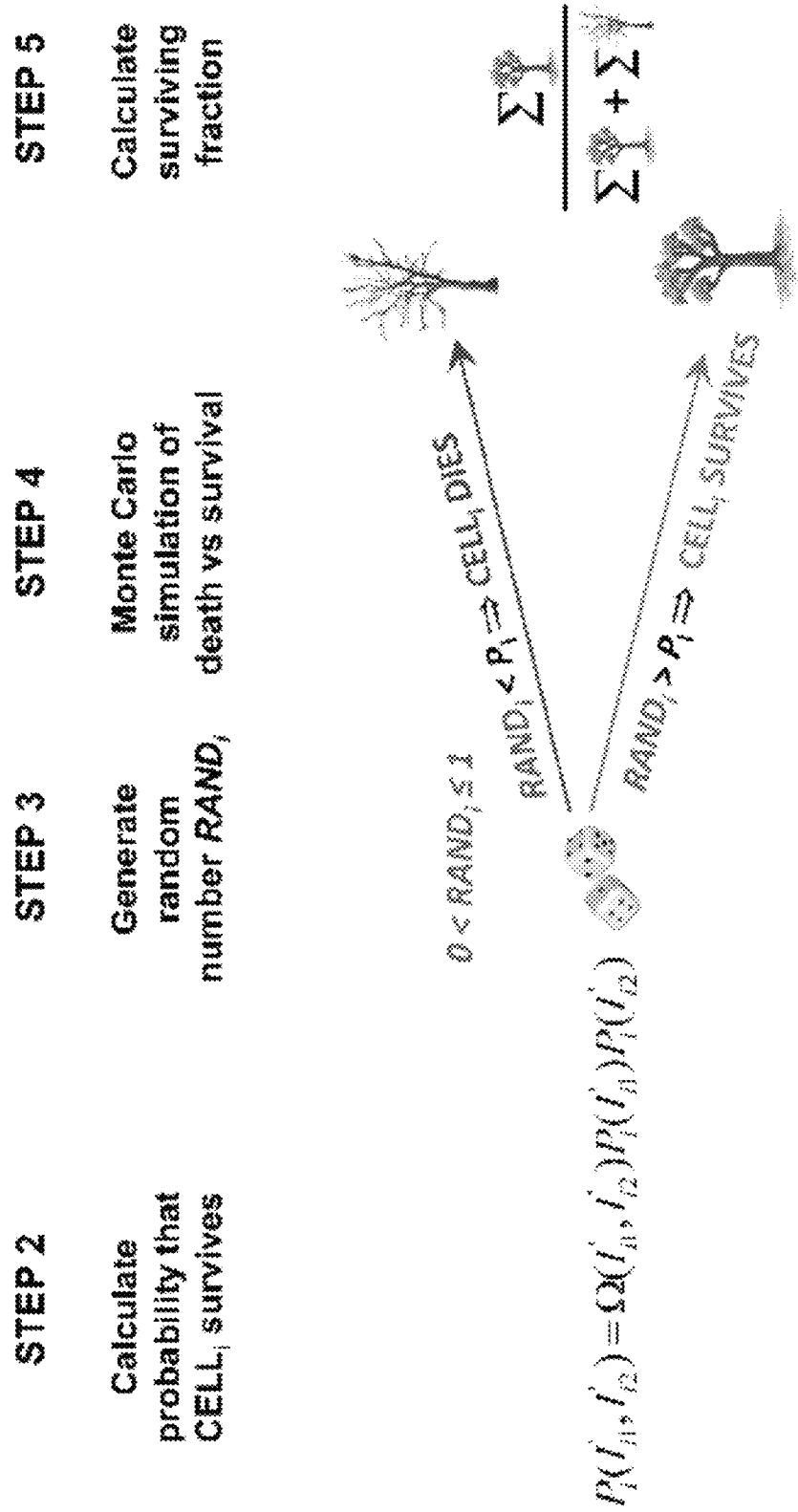
FIGURE 8 - Continued

METHODS AND SYSTEMS FOR DETERMINING THE DISTRIBUTION OF RADIATION DOSE AND RESPONSE

CROSS-REFERENCE TO RELATED APPLICATIONS

The present application claims the benefit of priority of U.S. Provisional Application No. 61/785,146 filed on Mar. 14, 2013, the disclosures of which is incorporated by reference herein in its entirety.

STATEMENT REGARDING FEDERALLY SPONSORED RESEARCH OR DEVELOPMENT

The invention was made with government support under Grant No. R01 CA083838 awarded by the NIH/NCI. The government has certain rights in the invention.

BACKGROUND

The use of chemotherapeutic drugs as an adjuvant to external beam radiotherapy, surgery, or other treatment modalities is common practice for the treatment of a wide variety of solid tumors. This approach has demonstrated some success in the management of certain cancers. The rationale for combining chemotherapeutic agents with external beam radiotherapy is to radiosensitize the irradiated tumor tissue and/or to target subpopulations of malignant cells that have metastasized from the primary lesion demarcated for beam therapy. Although the tradition of chemoradiotherapy has been practiced for decades and shows promise, some attempts have not succeeded in demonstrating either an added therapeutic benefit or a reduction of normal tissue toxicity. In another approach, radiolabeled chemotherapy agents have been used in an attempt to achieve enhanced cytotoxicity both in human cancer cells and apparently normal hamster fibroblasts. Chemotherapy has also been combined with radioimmunotherapy.

One limitation of chemoradiotherapy is the frequent lack of interaction between chemotherapeutics and ionizing radiation. This often leads to escalation of radiation and drug doses, which in turn, results in elevated normal tissue toxicity. Moreover, lack of specificity of chemotherapy drugs for tumor tissue can result in an insignificant difference in toxicity towards malignant and normal tissues thereby providing no added therapeutic benefit compared to surgery and radiation alone. Despite these limitations, chemoradiotherapy often provides considerable therapeutic benefit. However, observed inconsistencies in treatment outcomes may be due to the widely varying chemotherapeutic drug concentrations employed and radiation absorbed doses achieved. In addition, there is evidence demonstrating that optimization of radiation dose and drug concentration, and the time sequence for administering drugs and radiation play important roles in treatment responses both in vitro and in vivo. Also, regardless of the quality of radiation used, the wide variability in drug toxicity in normal cells of different histologies has to be considered in favor of the most sensitive tissue in chemoradiotherapy. Unfavorable outcomes in therapies involving the use of chemotherapy drugs and radiopharmaceuticals have been attributed to insufficient tumor specificity, poor tumor vascularization, and nonuniformities in agent distribution at the macroscopic, cellular, and subcellular levels. Determination of drug and radionuclide incorporation at the single-cell level has been difficult. As such, estimation of intracellular chemotherapy drug concentration and intra-cellular radioactivity (required to determine radiation absorbed dose to the cell) has largely been restricted to the macroscopic level. Accordingly, it has been difficult to establish a relationship between therapeutic agent incorporation and biologic response.

In addition, the limited success in chemo-radiotherapy of primary solid tumors and metastatic disease is likely due to this lognornnal phenomenon, in which minute subpopulations of cells take up very little or no therapeutic agent. Repopulation by these subpopulations could mask a possible treatment benefit and result in an even more resistant neoplastic form. Thus, to enhance tumor response, there continues to be a need to address the nonuniform, lognormal distribution of chemotherapy drugs and radiopharmaceuticals.

Prediction of tumor and normal-tissue responses in therapeutic nuclear medicine relies heavily on calculation of the absorbed dose. A general formalism was developed by the Medical Internal Radiation Dose (MIRD) Committee of the Society of Nuclear Medicine to calculate absorbed doses from tissue-incorporated radioactivity. However, absorbed-dose specification is complex due to the wide variety of radiations emitted, heterogeneity in activity distribution and biokinetics, and other confounding factors. Following the administration of a radiopharmaceutical, the radioactivity is taken up by tumors (if any) and the various organs within the body and the radioactivity is then eliminated through both biological clearance and physical decay.

The extent to which nonuniform distributions of radioactivity within a small tissue element impact the absorbed dose distribution, and ultimately the biological effect, is strongly dependent on the number, type, and energy of the radiations emitted by the radionuclide. Many radionuclides used in nuclear medicine decay by electron capture and/or internal conversion (e.g. $^{67}$Ga, $^{99m}$Tc, $^{111}$In, $^{123}$I, $^{201}$Tl) and consequently emit a large number of low-energy Auger and conversion electrons. Many of these electrons deposit their energy over subcellular dimensions and therefore produce nonuniform dose distributions. Similarly, the short range of alpha particles in biological tissues (40-100 μm) also leads to nonuniform dose distributions from $^{223}$Ra and other alpha particle emitters of potential use in nuclear medicine. Energetic beta emitters such as $^{90}$Y have a greater degree of cross-irradiation because their mean range in tissue is at least several hundred microns. However, the nonuniform distribution of these radionuclides invariably leads to nonuniform dose distributions as well. While it is essential to consider the dose distributions that arise from nonuniform distributions of radioactivity, it is also necessary to know whether the dose to a given cell arises from radioactive decays within itself (self-dose) or decays in surrounding cells or other parts of the body (cross-dose). Cellular response to self-dose delivered by a radiopharmaceutical can be considerably different than its response to cross-dose from the same radiopharmaceutical. Accordingly, there is a need for tools and methods that can model biological responses to nonuniform activity distributions encountered in nuclear medicine, to assist in designing therapeutic nuclear medicine treatment strategies for patients undergoing nuclear medicine procedures for cancer therapy.

BRIEF SUMMARY OF THE INVENTION

An embodiment of the present invention relates to a novel method for predicting the optimal amount of radiopharmaceutical and chemotherapy agents to administer to a patient, by determining the level of cell saturation, geometry of a cluster(s) of cells, and cross dose to a neighboring cell. This includes a method of predicting the response of an individual patient's disease to therapeutic intervention with radiopharmaceuticals, chemo-therapeutics, targeted therapeutics such as radiolabeled monoclonal antibodies, or other agents. Cellular incorporation of therapeutic agents may be measured in the target cell population on a cell-by-cell basis using a flow cytometer. The resulting fluorescence spectra are fitted to the lognormal probability density function to obtain the lognormal shape parameter, σ, also known as the standard deviation, for each treated sample. Surprisingly it has been discovered that: (1) changes in the lognormal shape parameter, σ, upon exposure of the cells to increasing drug concentrations, correlate with changes in the shape of the cell survival curve, and therefore can identify the optimal drug concentration for use in a drug cocktail; (2) the surviving fraction of a target cell population exposed to the therapeutic agent can be predicted using a flow-cytometry assisted Monte Carlo simulation that accounts for the lognormal characteristics of the distribution; and (3) the optimal cocktail of therapeutic drugs can be identified by exposing target cells to combinations of drugs, whereby the optimal concentration of each drug is identified using (1), by employing flow cytometry to simultaneously measure the uptake of each drug, then simulating the surviving fraction of the target population using (2), and using the simulated results to identify the combination of drugs that affords the optimum degree of killing of the target cells. (1) and (2) have been demonstrated with a radiochemical ($^{210}$Po-citrate) and two anticancer drugs (daunomycin and doxorubicin) in Chinese hamster V79 cells. (3) has been demonstrated with a combination of $^{210}$Po and daunomycin and a combination of $^{210}$Po and doxorubicin. Another aspect of the invention provides patient-specific cocktail formulations by identifying existing drugs that can be added to a cocktail to facilitate targeting subpopulations of cells that would otherwise escape targeting.

An additional embodiment of the invention is directed to a computing-implemented method of determining a dose of radiation for a patient for radiation therapy treatment planning, the method comprising: receiving, by a computing device, one or more features associated with a dose of radiation; displaying, by the computing device, a menu of one or more of the features associated with the dose of radiation, wherein each feature corresponds to a category of information; receiving, by the computing device from the user, a selection of one or more feature from the menu of features; and for each selected feature: receiving, by the computing device, information pertaining to the selected feature, determining, by the computing device radiation data for a radionuclide, determining, by the computing device a radiobiological parameter, determining, by the computing device a target volume and source volume, determining, by the computing device a cell geometry, and determining, by the computing device, a dose of radiation based upon the selected features. In a further embodiment, displaying a menu of one or more features comprises displaying a menu comprising an option associated with one or more of the following: a source of radiation; a cell source; a radiobiological parameter, and a cell geometry feature.

In another embodiment, the source of radiation feature is a radionuclide or a monoenergetic particle. In a further embodiment, the cell source feature comprises a target volume in a cell for which radiation absorbed dose will be calculated. In another embodiment, the radiobiological parameter feature comprises select values for calculating the probability that a given cell survives using the linear quadratic model. In a further embodiment, the cell geometry feature comprises one of the following: a one dimensional cell pair, a cell population that resides on a plane, or a three dimensional configuration of cells. In another embodiment, the radiation data for a radionuclide feature further comprises select values for radiopharmaceutical agents. In a further embodiment, the radiobiological parameter feature comprises select values for calculating the probability that a given cell survives using the linear quadratic model, and then determining the surviving fraction of cells within a colony of cells or a three dimensional cluster of cells. In another embodiment, the cell geometry feature comprises the distribution of activity among the cells that is based on data from a patient or from a laboratory.

An additional embodiment of the invention is directed to a radiation therapy planning system configured to determine a dose of radiation for a patient for radiation therapy treatment planning, the system comprising: a computing device; and a computer-readable storage medium in communication with the computing device, wherein the computer-readable storage medium comprises one or more programming instructions that, when executed, causes the computing device to: receive, one or more features associated with a dose of radiation from a computing source; display, a menu of one or more of the features associated with the dose of radiation, wherein each feature corresponds to a category of information; receive, a selection of one or more feature from the menu of features; and for each selected feature: receive information pertaining to the selected feature, determine radiation data for a radionuclide; determine a radiobiological parameter; determine a target volume and source volume; determine a cell geometry; and determine a dose of radiation based upon the selected features.

In a further embodiment, one or more programming instructions that, when executed, cause the computing device to display a menu of one or more features comprise one or more programming instructions that, when executed, cause the computing device to display a menu comprising an option associated with one or more of the following: a source of radiation; a cell source; a radiobiological parameter; and a cell geometry feature. In another embodiment, the source of radiation feature is a radionuclide or a monoenergetic particle. In a further embodiment, the cell source feature comprises a target volume in a cell for which radiation absorbed dose will be calculated. In another embodiment, the radiobiological parameter feature comprises select values for calculating the probability that a given cell survives using the linear quadratic model. In a further embodiment, the cell geometry feature comprises one of the following: a one dimensional cell pair, a cell population that resides on a plane, or a three dimensional configuration of cells. In another embodiment, the radiation data for a radionuclide feature further comprises select values for radiopharmaceutical agents. In a further embodiment, the radiobiological parameter feature comprises select values for calculating the probability that a given cell survives using the linear quadratic model, and then determining the surviving fraction of cells within a colony of cells or a three dimensional cluster of cells. In another embodiment, the distribution of activity among the cells is based on data from a patient or from a laboratory.

DETAILED DESCRIPTION

Figures 1A, 1B:
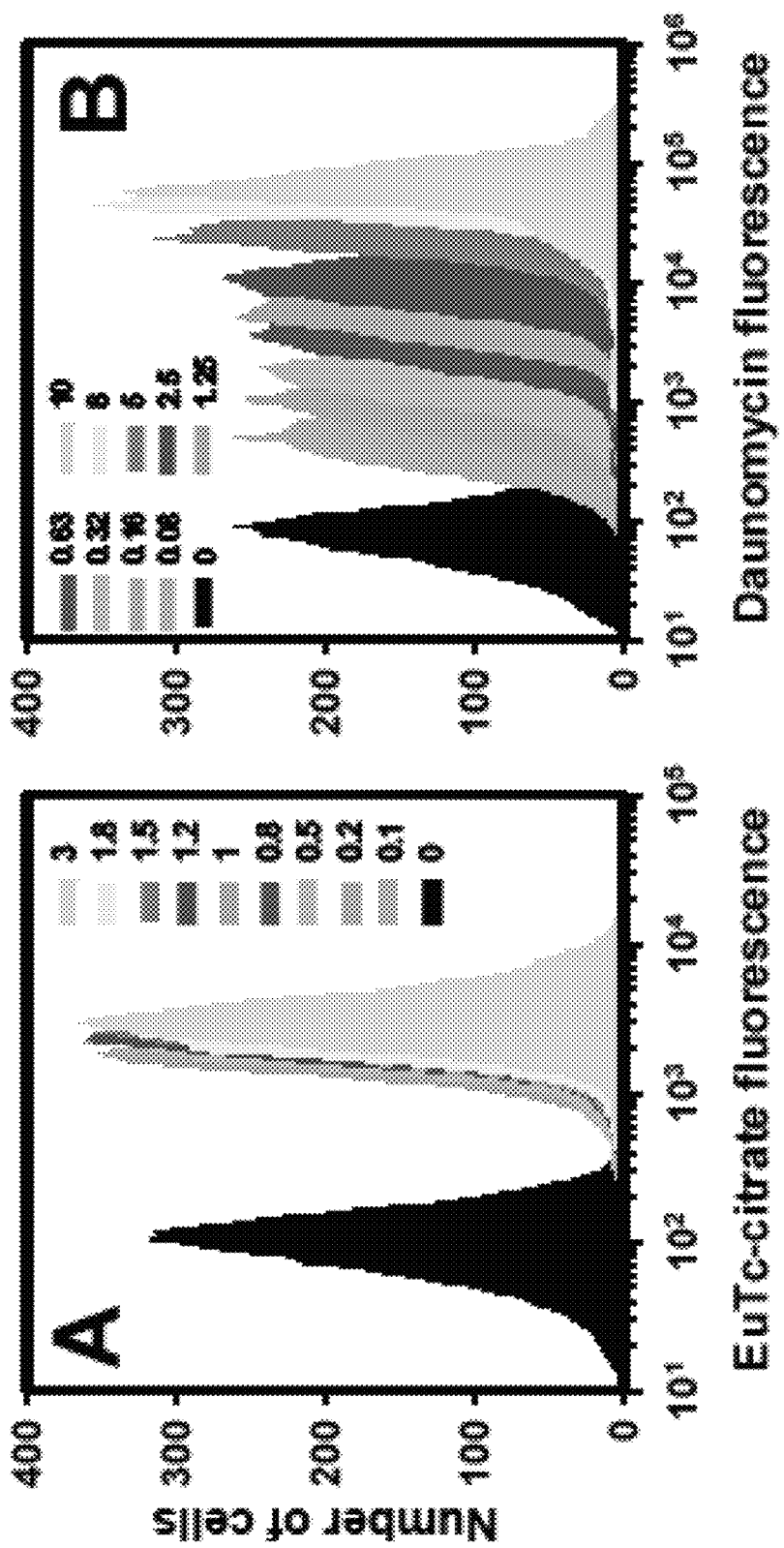
FIG. 1 shows the distribution of cellular uptake of citrate, daunomycin, and doxorubicin by V79 cells in a suspension culture. Displayed are representative flow cytometry generated histograms of cellular fluorescence intensity after treatment with 0-3 mmol/L EuTc-citrate (A), 0-10 μmol/L daunomycin (B), or 0-10 μmol/L doxorubicin (C).

The therapeutic significance of nonuniform incorporation of chemotherapy drugs and radiopharmaceuticals by cancer cells has been recognized as an issue of long standing in the art. Yet, the impact of lognormal drug distributions on the capacity of an agent to sterilize a population of cells has not been previously recognized. A small lognormal shape parameter ($\sigma$) implies a narrow distribution profile, and $\sigma$ approaches zero when all cells incorporate the same amount of agent. On the other hand, a large $\sigma$ signifies a wide spread in distribution, and agent incorporation may range from very low (potentially nontoxic) to high (lethal). The ubiquity of lognormal drug distributions has now been demonstrated by using flow cytometry to assess the distribution of radionuclides, for example, $^{210}$Po-citrate, and pharmaceutical agents, for example, daunomycin, and doxorubicin. Equally important is the discovery that changes in the value of $\sigma$ as a function of increasing drug concentration parallel marked changes in the shapes of the corresponding clonogenic cell survival curves. Further, surprisingly it has now been discovered that experimental lognormal distributions (i.e. individual drug uptake on a cell-by-cell basis) can be used to accurately predict the saturation that is observed in experimental cell survival-curves (e.g. two-component exponential curves). This saturation has now been observed repeatedly in studies on the lethal effects of nonuniform distributions of radioactivity. Furthermore, theoretical studies now show that lognormal distributions can lead to such two-component exponential survival curves in both monolayer and three-dimensional tissue constructs.

The overall biological response must be influenced by the magnitude of the mean cellular drug uptake and the degree of heterogeneity in agent distribution. Therefore, a change in the capacity of an agent to sterilize a cell population is related to both the change in width of the distribution and the peak-shift as the agent concentration increases. While the former is a measure of the broadness of a distribution profile of the agent among a cell population and can be represented by the lognormal shape parameter, $\sigma$, the latter is a shift in the lognormal scale parameter $\mu$ which is an indication of cells accumulating increasing levels of the agent. Changes in $\sigma$ are prognostic of whether a survival curve will exhibit saturation, and that $\sigma$ may guide in the selection of agents for multimodality cocktail design by providing information on agent concentrations at which the first component of cell kill ends. However, the shape parameter only describes the agent distribution profile of the cell population as a whole, but does not provide information on the fate of individual cells of the population.

Surprisingly, it has also now been discovered that clonogenic cell survival can be predicted based only on knowledge of the initial slope of the cell survival curve and information on the distribution of agent incorporation among the treated cell population. For example, the distribution of $^{210}$Po, daunomycin and doxorubicin among populations of Chinese hamster V79 cells was assessed using flow cytometry techniques and used to theoretically model the surviving fraction. Several modeling approaches were compared, including flow-cytometry gating of agent-negative cells, Monte Carlo simulation of cell survival based on the experimental distributions of drug uptake, and Monte Carlo simulation of cell survival based on the more conventional approach of using mean cellular uptake of the drugs.

Monte Carlo simulation using cellular agent incorporation based on individual cell fluorescence intensity of therapeutic agents is a suitable predictor of cell survival. This flow cytometry based approach, which takes explicit account of the lognormal distribution of cellular uptake of the agents, offers a rapid means for determining treatment response on a cell-by-cell basis, and allows the selection of agents for the design of highly effective therapeutic cocktails that are capable of targeting the diversity in tumor cell populations. Such cocktails can be created not only for treatment of cancer, but also for infectious diseases and other diseases that may be amenable to targeted therapies. Furthermore, this single-cell Monte Carlo technique can be used to resolve difficulties encountered when attempting to predict biological response at the multicellular level using macroscopic mean agent doses.

An embodiment of the invention is directed to a method for predicting the response of an individual patient's cells to therapeutic intervention comprising the steps of:

(a) exposing populations of said cells to increasing concentrations of a candidate therapeutic agent for said condition;
(b) measuring the incorporation of said therapeutic agent in said populations on a cell-by-cell basis, preferably employing a high-speed technique, preferably flow cytometry, with the incorporation being measured using fluorescence spectroscopy, preferably the individual cell fluorescence intensities and the mean fluorescence intensity (MFI);
(c) plotting the number of cells versus the amount of incorporated therapeutic agent, to obtain distribution plots for said populations;
(d) fitting said distribution plots to a probability density function, preferably a lognormal function, to obtain a distribution curve and the standard deviation, $\sigma$, for each population; and
(e) identifying the optimal concentration of said therapeutic agent for said patient by identifying changes in the slope of a plot of $\sigma$ as a function of concentration of said therapeutic agent.

The method may further comprise the steps of determining the surviving fraction of cells, plotting the surviving fraction versus the amount of incorporated therapeutic agent, and fitting the plot to a probability function, preferably selected from the group of functions consisting of exponential and linear-quadratic. Preferably, the method also further comprises the step of predicting the surviving fraction of said cell populations using a simulation, preferably a Monte Carlo simulation, that accounts for the characteristics of said distribution curve, preferably flow-cytometry assisted Monte Carlo simulation.

In a further embodiment of the invention, cells are exposed to increasing concentrations of a plurality of therapeutic agents, and the optimal concentration of each drug is identified. The simulation results are then used to identify an effective combination of therapeutic agents in their therapeutically effective amounts.

The biological targets of the method include cells with uncontrolled growth, such as tumor cells, or cells infected with pathogens, including without limitation, bacteria, viruses, prions, and parasites. The biological target may also include stem cells. In a preferred embodiment of the method, the individual patient's cells comprise cancer cells.

The therapeutic agents comprise, without limitation, antibodies, peptides, chemo-therapeutics, radiopharmaceuticals, antifungals, antiobiotics and other pharmaceuticals.

Any high-speed technique for assaying drug uptake on a cell-by-cell basis, as known in the art, can be used, including, without limitation, microfluidic techniques such as flow cytometry and microfluidic impedance cytometry; laser scanning microscopy; and gas chromatography/mass spectrometry (GC/MS). Preferably, the high-speed technique for assaying therapeutic agent uptake on a cell-by-cell basis comprises flow cytometry. The analytical method used to determine the incorporation of therapeutic agent preferably comprises fluorescence spectroscopy. The fluorescence measurement preferably comprises individual cell fluorescence intensities and the mean fluorescence intensity (MFI).

Preferably, the probability density function of step (d) is selected from the group of functions consisting of lognormal, normal, Weibull and exponential. The probability function chosen will have some impact on the value of $\sigma$, and therefore will have some impact when determining the optimal concentration from plots of $\sigma$ versus concentration. Most preferably, the probability density function is lognormal. However, the simulation of the surviving fraction can also directly employ the incorporation data (e.g. flow cytometry data) without relying on a lognormal or other function fit to obtain $\sigma$.

The probability function of the plot of surviving cell fraction versus the amount of incorporated therapeutic agent can be any typical dose-response function. Preferably this survival probability function is selected from the group of functions consisting of exponential and linear-quadratic, and is most preferably exponential.

Preferably, the Monte Carlo simulation method comprises flow-cytometry assisted Monte Carlo simulation.

In a further embodiment of the invention is directed to a method for predicting the response of an individual patient's cancer cells to therapeutic intervention comprising the steps of:
(a) exposing populations of said cancer cells to increasing concentrations of a candidate therapeutic agent for said cancer;
(b) measuring by fluorescence spectroscopy the incorporation of said therapeutic agent in said populations on a cell-by-cell basis using a flow cytometer, to provide net mean fluorescence intensity (MFI);
(c) plotting the number of cells versus the net MFI, to obtain a distribution plot for said population;
(d) fitting said distribution plot to a lognormal probability density function to obtain a lognormal distribution curve and the standard deviation, $\sigma$, for each population; and
(e) identifying the optimal concentration of said therapeutic agent for said cancer patient from changes in slope of a plot of $\sigma$ as a function of concentration of said therapeutic agent.

Preferably, the method further comprises the step of predicting the surviving fractions of said cell populations using a flow-cytometry assisted Monte Carlo simulation that accounts for the characteristics of said lognormal distribution curve.

In a further embodiment of the invention, the cancer cells are exposed to increasing concentrations of a plurality of therapeutic agents, and the optimal concentration of each drug/agent is identified, and the simulation results are used to identify a combination of therapeutic agents that affords a high degree of killing of the cancer cells. Preferably the degree of killing of the cancer cells is about 99% or greater, more preferably 99.9% or greater, and most preferably 99.99% or greater. The method can also be used to identify a combination of drugs that affords the optimum degree of killing of the cancer cells.

In yet another embodiment of the invention, the method further comprises the step of identifying one or more drugs that can be added to a combination of therapeutic agents to facilitate the killing of subpopulations of cells that would otherwise escape killing by said combination.

Yet another embodiment of the invention comprises a method of high-throughput drug discovery comprising the method described above for predicting the response of an individual patient's cells to therapeutic intervention. Such an embodiment can be implemented on a high-throughput drug discovery platform. For example, in one embodiment, a tissue sample from a patient would be cultured and loaded into a high-throughput drug discovery device which is coupled to a flow cytometer, numerous combinations from a library of drugs would be screened, and a cocktail specific for the patient at hand would be identified.

Still another embodiment of the invention is directed to a 2-stage targeting method of treating a disease or condition for a patient in need thereof, the method comprising:

(1) identifying and providing a plurality of candidate targeting agents relevant to the disease or condition of said patient, wherein said targeting agents are two-stage agents comprising:
   (a) Stage 1 agents which are non-toxic and target the diseased or affected cells; and
   (b) Stage 2 agents which bind to said Stage 1 agents and carry at least one additional agent selected from the group consisting of toxins, radionuclides and fluorochromes, wherein each Stage 2 agent can only bind to a single corresponding Stage 1 agent;
(2) injecting said patient with a cocktail of Stage 1 agents via a route appropriate to said disease or condition, and allowing sufficient time for maximum uptake by said diseased or affected cells and substantial clearance of unbound Stage 1 agents;
(3) withdrawing a sample of said patient's diseased or affected cells loaded with Stage 1 agents;
(4) treating said sample of said cells in vitro with a cocktail of said Stage 2 agents, wherein each Stage 2 agent carries a unique fluorochrome, and wherein said Stage 2 agents bind to said Stage 1 agents loaded into said cells;
(5) quantifying the amount of each Stage 2 agent binding to each diseased or affected cell using fluorescence spectroscopy;
(6) predicting the response of said diseased or affected cells for every possible combination of Stage 1 and Stage 2 agents using the above method for predicting the response of an individual patient's cells to account for the lognormal distribution of each agent, and identifying the optimal combination of said agents;
(7) arming each Stage 2 agent of said optimal combination with one or more therapeutic agents selected from the group consisting of toxins, radionuclides, and combinations or two or more thereof, to form an armed cocktail;
(8) optionally, repeating step (2); and
(9) injecting said armed cocktail into said patient.

The method may further comprise repeating steps (3) through (6) with healthy cells of said patient in place of diseased/affected cells, in order to assess the uptake of said Stage 1 and Stage 2 agents in each healthy cell.

A further embodiment of the invention is directed to a computational method for processing the above-indicated data, including flow cytometry data, in order to determine the parameter $\sigma$ and calculate therefrom the optimal dose, or effective dose, of each component of the drug cocktail.

In addition, the above-identified methods can be used in radioimmunochemotherapy to predict the toxicity of cocktails of $\alpha$-emitting radiopharmaceuticals and chemotherapy drugs in a manner that takes into account the effects of lognormal and other nonuniform distributions of agents within cell populations. These agents can interact with one another and cause greater than expected effects based on their single-agent toxicities. The approach is employed advantageously in the selection of agents for the design of highly effective $\alpha$-particle based therapeutic cocktails that are capable of targeting the diversity in tumor cell populations.

The above-identified methods have the capacity to predict clonogenic survival after multi-modality therapy, using flow cytometry-assisted Monte Carlo simulation. It is demonstrated herein that Monte Carlo simulation using cellular agent incorporation based on individual cell fluorescence intensities of therapeutic agents is a suitable predictor of cell survival. This model accounts for the lognormal distribution of cellular uptake of the agents, and is capable of predicting treatment response on a cell-by-cell basis.

Cellular Uptake of $^{210}$Po-Citrate, Daunomycin, and Doxorubicin

Figure 1C:
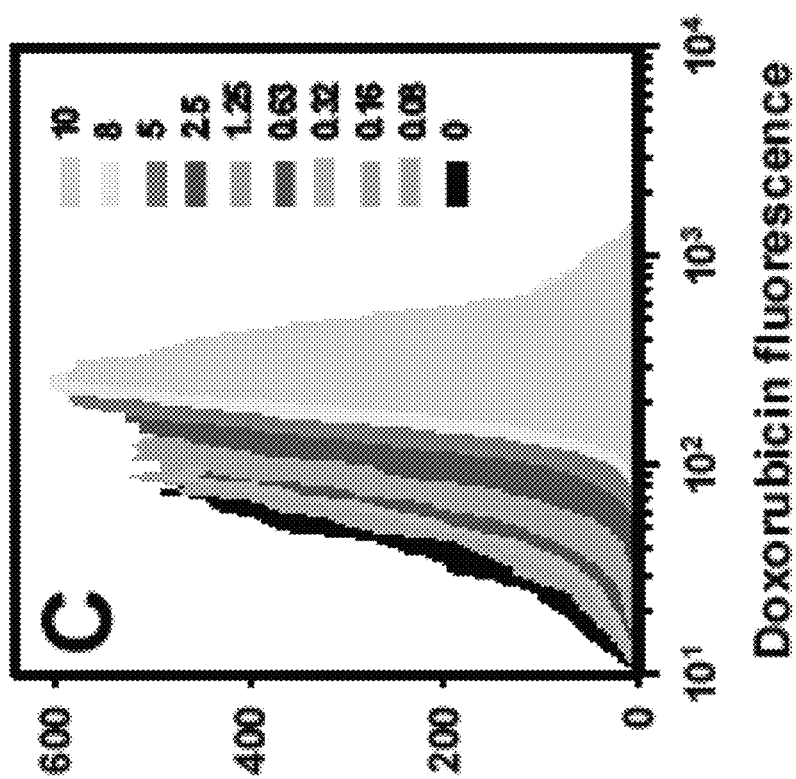
Figures 2A, 2B, 2C:
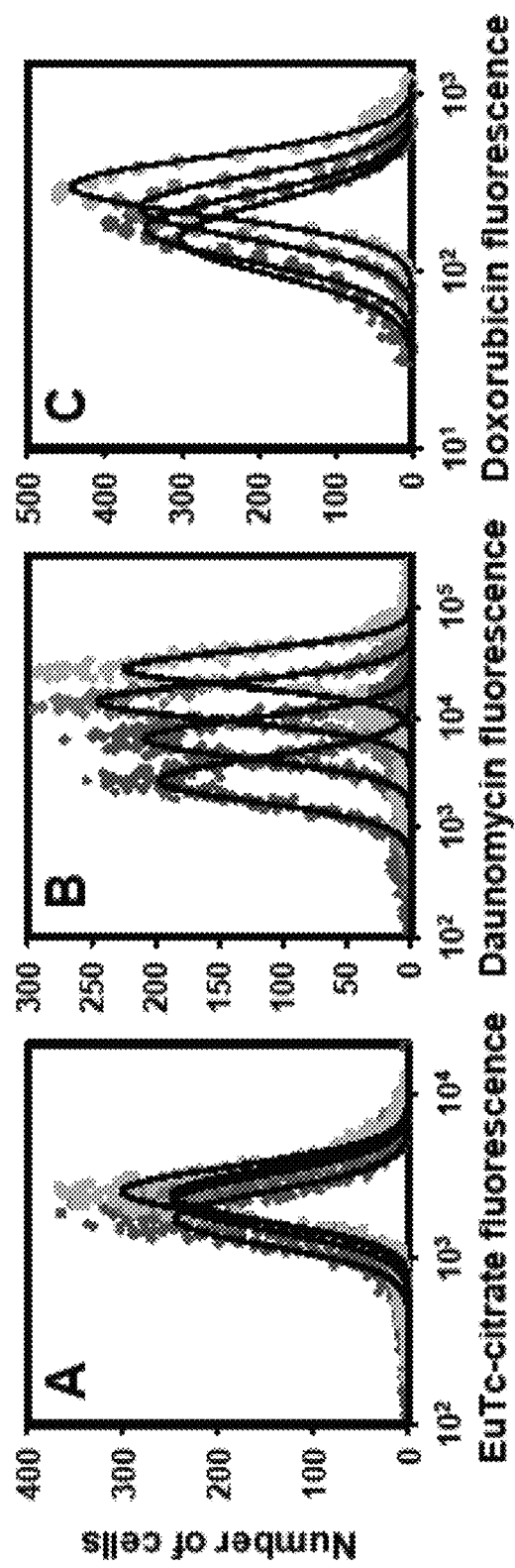
FIG. 2 shows the least squares fits of the flow cytometry fluorescence intensity histograms to a lognormal probability distribution. The histograms correspond to (A) EuTc-citrate, (B) daunomycin, and (C) doxorubicin.
Figures 3A, 3B, 3C:
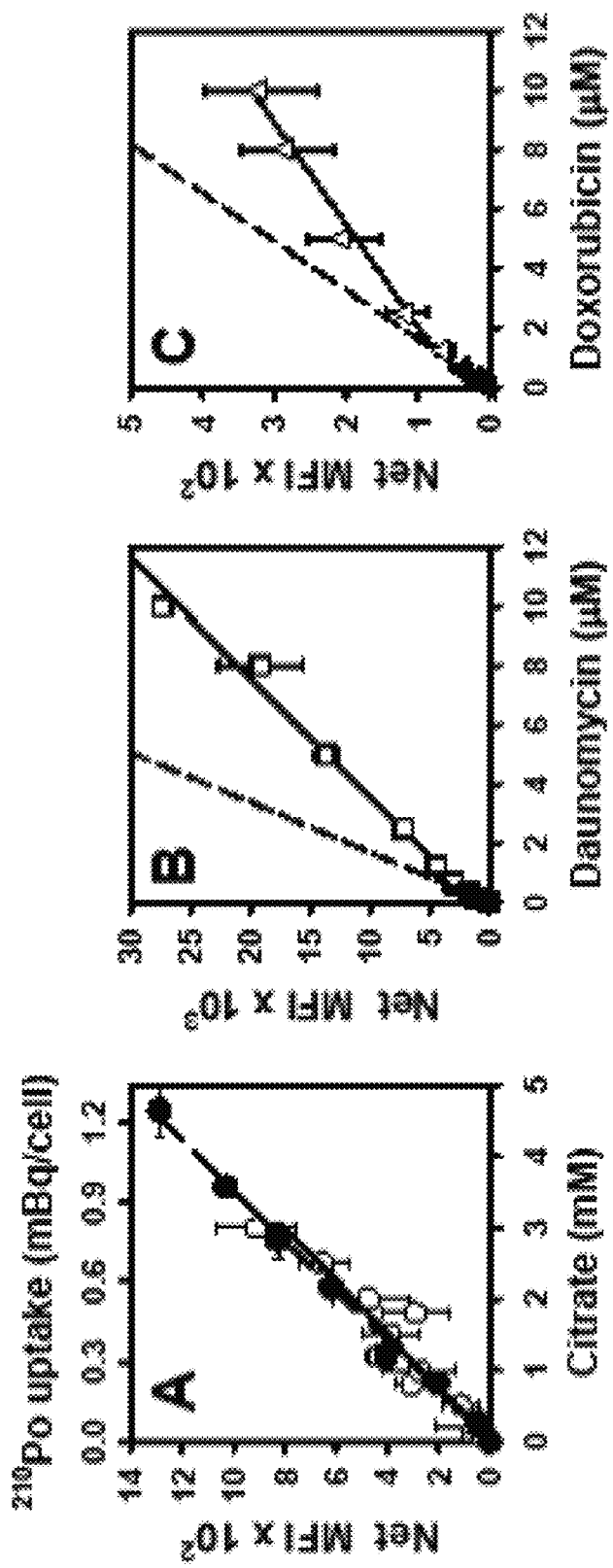
FIG. 3A displays net mean fluorescence intensity (MFI) of europium tetracycline-citrate complex (EuTc-citrate) as a function of extracellular citrate concentration (open circle, solid line) and corresponding mean $^{210}$Po activity per cell (filled circle, dashed line). Lines represent least squares fits of the data to linear functions: $MFI=267\pm16(mmol/L)^{-1} \times C_{cit}$, and $MFI=1058\pm19(mBq/cell)^{-1} \times \langle a_0 \rangle$, where $C_{cit}$ and $\langle a_0 \rangle$ are the extracellular citrate concentration and mean cellular activity of $^{210}$Po, respectively. B displays net MFI of intracellular daunomycin after exposure to low extracellular concentrations (filled square, dashed line) and high concentrations (open square, solid line). Linear least squares fits to the data give $MFI_{dauno}(C_{dauno}<0.6 \, \mu mol/L)=5922 \, (\mu mol/L)^{-1} \times C_{dauno}$ and $MFI_{dauno}(C_{dauno}>0.6 \, \mu mol/L)=2480 \, (\mu mol/L)^{-1} \times C_{dauno}+1161$. C. Net MFI of intracellular doxorubicin after exposure to low extracellular concentrations (filled triangle, dashed line) and high concentrations (open triangle, solid line). Linear least squares fits to the data give $MFI_{doxo}(C_{doxo}<1 \, \mu mol/L)=61 \, (\mu mol/L)^{-1} \times C_{doxo}$ and $MFI_{doxo}(C_{doxo}-1 \, \mu mol/L)=40(\mu mol/L)^{-1} \times C_{doxo}+29$. For all cases, error bars represent standard error (SE) of three independent experiments.

FIG. 1 shows flow cytometry histograms of the fluorescence intensity of V79 cells that were treated with $^{210}$Po-citrate (FIG. 1A), daunomycin (FIG. 1B), or doxorubicin (FIG. 1C) at concentrations ranging from 0-3 mmol/L, 0-10 µmol/L, and 0-10 µmol/L, respectively. Note that the peaks shift toward higher mean fluorescence as the extracellular concentration of the drug increases. The relatively symmetric nature of the histograms as plotted on a linear-log scale is suggestive of a lognormal distribution of each agent among the cell population. Fluorescence intensity distribution is a lognormal function of the fluorescence intensity I, $$f(I) = \frac{g}{I\sigma\sqrt{2\pi}} e^{-\frac{(\ln I - \mu_I)^2}{2\sigma^2}}, I > 0$$

where $\mu_I$ is the scale parameter, $\sigma$ is the shape parameter, and g is a constant. Least squares fits of the data to this distribution are shown in FIG. 2. Although not observed for EuTc-citrate (FIG. 2A), there is a decrease in the breadth of the lognormal distributions corresponding to daunomycin (FIG. 2B) and doxorubicin (FIG. 2C). Treatment with 0.1 mmol/L citrate resulted in a large increase in mean fluorescence intensity (MFI) from ~163 in untreated samples to ~2000. This can be attributed to the high sensitivity of EuTc for detecting citrate. EuTc is capable of detecting citrate in solutions at concentrations ~1000-fold lower. Since 0.1 mmol/L corresponded to an intracellular $^{210}$Po activity of ~0.02 mBq/cell, which translates to no significant cell kill, background fluorescence of 2000 units was subtracted from the MFI of each sample to obtain a net MFI. The net MFI was then plotted as a function of extracellular citrate concentration (FIG. 3A). With knowledge of the linear correlation between MFI and extracellular citrate concentration, and knowledge of the linear correlation between cellular uptake of $^{210}$Po and extracellular $^{210}$Po-citrate concentration, a similar correlation could be established between MFI and intracellular $^{210}$Po activity (FIG. 3A). A very strong correlation is apparent between cellular incorporation of the vehicle citrate and intracellular $^{210}$Po-activity. Similarly, the fluorescence histograms obtained after treatment of cells with daunomycin and doxorubicin are presented in FIGS. 3B and 3C, respectively. For both drugs, the MFI for the untreated controls were subtracted as background from the MFI of each sample, and the net MFI was plotted against extracellular drug concentration. In each case, net MFI was linearly correlated with drug concentration.

Briefly, flow cytometry was used to quantify their mean fluorescence intensity (MFI) per cell, $<I>$, as a function of the concentration of the agent in the cell culture medium. The net mean fluorescence intensities per cell, $<I>_{net}$, were determined by subtracting control autofluorescence $<I>_{control}$, Equation (1):

$$<I>_{net} = <I> - <I>_{control} \tag{1}$$

The surviving fraction SF of cells exposed to the agent was assessed with a clonogenic survival assay and plotted as a function of several different variables including extracellular concentration, $<I>_{net}$, absorbed dose (Gy), and mean cellular activity (mBq/cell). The resulting survival curves were of a 1- or 2-component exponential form. Analogous to the cellular activity and absorbed dose required to achieve 37% survival, $a_{37}$ and $D_{37}$, the net mean lethal fluorescence intensity of the drug required to achieve 37% survival, $<I>_{net,37}$, can be defined similarly and obtained from plots of SF versus $<I>_{net}$.

Cellular Dosimetry

The absorbed dose to the cell nucleus was determined as known in the art. Since cells were treated with $^{210}$Po-citrate as a single-cell suspension and were subsequently seeded for colony formation, the small contribution of cross-irradiation from neighboring cells in the colony can be ignored because it is essentially counterbalanced by the reduction in self-dose caused by flattening of cells during the colony forming period. The data was least squares fitted to obtain a mean biologic half-time of 11.6 h. Considering the physical half-life of 138 d for $^{210}$Po, this yields an effective half-time $T_e$ of 11.6 h. This $T_e$, the maintenance period of 2.5 h, the subcellular distribution of $^{210}$Po-citrate (28% nucleus, 72% cytoplasm) for V79 cells and published S values, were used to calculate a mean absorbed dose to the cell nucleus of 5.8 Gy/mBq of $^{210}$Po incorporated into the cell.

Toxicity of $^{210}$Po-Citrate, Daunomycin, and Doxorubicin

Figures 4A, 4B, 4C:
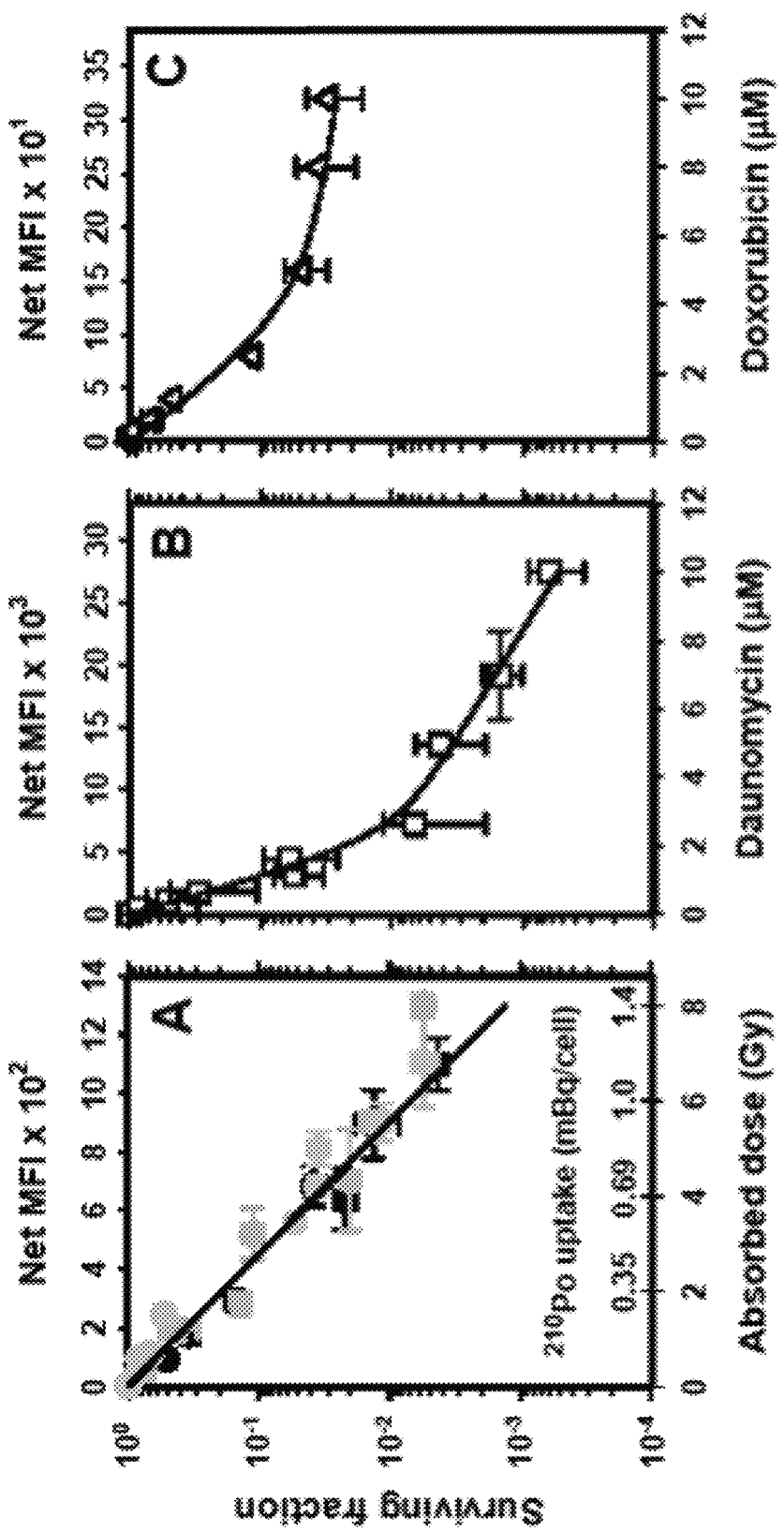
FIG. 4 shows the surviving fraction (SF) of V79 cells after treatment with various agents. A displays $^{210}$Po-citrate for three independent experiments, SF plotted against absorbed dose to the cell nucleus, intracellular $^{210}$Po activity, and net mean fluorescence intensity (MFI) of the europium tetracycline-citrate complex. Data plotted are from three independent experiments. Curve represents a least squares fit of the data to a single component exponential function. B displays daunomycin (open square), SF plotted against extracellular drug concentration and against net MFI of the drug. C displays doxorubicin (open triangle), SF plotted against extra-cellular drug concentration and against net MFI of the drug. Curves for daunomycin and doxo-rubicin represent least-squares fits to a two-component exponential function. For $^{210}$Po-citrate, horizontal and vertical error bars represent SE of mean cellular activity and surviving fraction of triplicate measurements, respectively. For daunomycin and doxorubicin, horizontal and vertical error bars represent SE of Net MFI and surviving fraction for three independent experiments.

To evaluate $^{210}$Po cytotoxicity, the surviving fraction was plotted as a function of EuTc-citrate net MFI, mean cellular uptake of $^{210}$Po, and mean absorbed dose to the nucleus (FIG. 4A). The data indicate that net MFI of the vehicle (citrate) is a good predictor of $^{210}$Po toxicity within the range of cellular activities employed. The relationships between cell survival and EuTc-citrate net MFI or cellular $^{210}$Po activity can be described by an exponential function SF=exp$(-A/A_1)$. The relationship between cell survival and drug net MFI (or extracellular concentration) for daunomycin and doxorubicin are illustrated in FIGS. 4B and 4C, respectively. For both drugs, clonogenic survival and cellular drug uptake (as determined by net MFI) are related via two component exponential functions SF=b exp$(-A/A_1)$+(1−b) exp$(-A/A_2)$. A is the intracellular activity of $^{210}$Po-citrate, absorbed dose to the cell nucleus, or drug concentration. Least squares fits of the survival data to this function were performed. The variable b is a fitted parameter.

Role of Agent Distribution in Cellular Toxicity

To evaluate the role of the distribution of $^{210}$Po-citrate, daunomycin, and doxorubicin within a cell population in their subsequent toxicity, the fluorescence histograms presented in FIG. 1 were fitted to the lognormal probability density function to obtain the shape parameter σ (FIGS. 1 and 2). Although increasing intracellular $^{210}$Po activity did not have an appreciable effect on σ over the entire range of concentrations studied for $^{210}$Po-citrate, increases in extracellular drug concentration had a marked impact on σ for both daunomycin and doxorubicin. The relationship between cell survival and σ for the three agents is illustrated in FIGS. 6 and 7. These plots show that σ for $^{210}$Po-citrate does not change appreciably as the surviving fraction decreases. However, σ for daunomycin and doxorubicin decreases substantially as the surviving fraction decreases.

Chemotherapy drugs and radiopharmaceuticals are typically heterogeneously distributed in tissues at the macroscopic, cellular, and subcellular levels. In the case of radiopharmaceuticals, this complicates estimation of cellular absorbed doses based on cellular activities, and causes the relationship between incorporated radioactivity and biologic response to be complex. Several in vitro studies have demonstrated saturation in cell kill with increasing activity per cell following exposure to a variety of radiochemicals, and have attributed the phenomenon to the lognormal nature of the agent distribution. This has also been shown for two chemotherapeutics, daunomycin and doxorubicin. Given the difficulty that is being experienced clinically in terms of sterilizing tumor cell populations with these and other agents, a more thorough understanding of their lognormal distributions and how they affect cell killing is needed to assist in selecting combinations of agents and guide the dosing of the constituent agents. Some enlightenment can be obtained by interpreting the flow cytometric and clonogenic survival studies described above. FIG. 1 demonstrates that flow cytometry can, under certain circumstances, be used to quantitate intracellular drug concentration. In the present case, this approach is used for EuTc-citrate (surrogate for $^{210}$Po-citrate), and two different chemotherapy drugs, daunomycin and doxorubicin. The distributions of intracellular agent concentration are lognormal (FIG. 2). As shown in FIG. 2A and FIG. 1, the EuTc-citrate is exquisitely lognormal throughout the range of extracellular drug concentrations studied. Not only is it lognormal, but the breadth of the peak remains consistent as well. This fact is confirmed by the absence of change in σ that is observed for EuTc-citrate in FIGS. 6 and 7. In contrast, the breadths of the peaks and their corresponding σ values change markedly for daunomycin and doxorubicin (FIG. 7). Furthermore, there are notable exceptions to the lognormality of the data acquired for daunomycin and doxorubicin (FIG. 1). In the case of daunomycin, there appears to be a growing population of cells on the low fluorescence side of the peak as the extracellular concentration increases. Conversely, doxorubicin's small departure from lognormality occurs at low extracellular drug concentrations. These changes occur in concert with changes in the slope of the drug uptake versus concentration of the drug in the extracellular medium, as emphasized by the dashed versus solid lines in FIGS. 3B and 3C. The net MFI of intracellular EuTc-citrate is strongly correlated with both extracellular citrate concentration and intracellular $^{210}$Po activity (FIG. 3A), indicating that MFI of EuTc-citrate is related to $^{210}$Po toxicity. Similarly, the data for daunomycin and doxorubicin in FIGS. 3B-C support the notion that the extent of agent incorporation by cells can be used as a predictor of their cytotoxicity. To validate the latter, cell survival is plotted against net MFI and extracellular drug concentration, or against intracellular $^{210}$Po activity and absorbed dose to the cell nucleus from $^{210}$Po-citrate (FIG. 4A). For $^{210}$Po-citrate, less than 2-logs of cell killing is observed. The relationship between the surviving fraction and net MFI (or cellular activity or absorbed dose) is exponential. Notably, neither the slope of the cellular uptake curve (FIG. 3A), nor the slope of the survival curve (FIG. 4A), nor the value of the shape parameter (FIGS. 6 and 7), change over the course of the concentrations required to achieve zero to two logs of cell kill. These conditions may be requirements needed to achieve a monoexponential survival curve and avert tailing of the survival curve. The data in FIGS. 4B-C illustrate that cell survival is related to extracellular concentration (or net MFI) of daunomycin and doxorubicin by a 2-component exponential function, with tails analogous to those observed using radiochemicals. Daunomycin and doxorubicin are closely related anthracyclines and interact with DNA by intercalation. Based on extracellular drug concentration in V79 cell cultures, daunomycin ultimately emerged to be more cytotoxic than doxorubicin. While this may be due to differences in the extent to which the drugs are incorporated, this cannot be ascertained by flow cytometry alone but rather with the help of cellular uptake studies with daunomycin and doxorubicin labeled with $^3$H or $^{14}$C at known specific activities. What is certain is that the slope of the cellular uptake curves (FIGS. 3B-C), and the slope of the survival curves (FIGS. 4B-C), and the value of the shape parameter (FIG. 7), all changed over the span of concentrations required to see the emergence of a tail in the survival curves. The presence of these conditions appears to be related to the two-component exponential survival curves. In fact, the concentration (ca. 1-2 μmol/L) at which these parameters begin to change (FIGS. 2, 3, 6 and 7) appears to coincide with the transition to the second component (FIG. 4).

The mean lethal concentrations for daunomycin and doxorubicin are 0.24 and 1.26 μmol/L, respectively. This indicates that low extracellular concentrations of daunomycin are ~5× more lethal than doxorubicin in V79 cells. The mean lethal absorbed dose for $^{210}$Po-citrate is 1.2 Gy. This arises from an uptake of 0.21 mBq/cell which corresponds to about 3600 atoms of $^{210}$Po. Although the survival curve is similar to that obtained previously, the present mean lethal dose is higher than the former value of 0.7 Gy. This is largely due to improved S values. Although, there is an interest in using multimodal approaches that involve the concomitant delivery of chemotherapeutic and radiotherapeutic agents for cancer treatment, the efforts have mostly not been directed at using agent-specific distribution profiles to target all malignant cells. To facilitate the design of cocktails that effectively target all cells of interest, an in-depth knowledge of the distribution profile of each agent is required. This warrants the ability to express cellular incorporation of agents in absolute units on a cell-by-cell basis. As an initial step towards this end, the flow cytometric histograms presented in FIG. 2 were fitted to the lognormal probability density function, and the derived shape parameters (σ) were plotted against intracellular $^{210}$Po activity or extracellular drug concentration. It is not surprising that these data are closely analogous to the established relationship between heterogeneity of intracellular incorporation of doxorubicin and extracellular drug concentration, as the shape parameter is a measure of the broadness of a distribution profile. While a small σ implies a narrow distribution profile (i.e. σ→0) when all cells incorporate the same amount of agent), a large σ signifies a wide spread in distribution. In practice, σ>0 and therefore subpopulations of cells will always incorporate subtoxic amounts of any given agent. However, as it has been shown as part of the present invention, the value of σ is not itself necessarily the primary determinant of the shape of the survival curve. Rather, changes in the value of σ (FIG. 7) and changes in the slope of the cellular uptake curves (FIGS. 3B and 3C), appear to correlate with changes in the transition from the first component to second component of the two-component exponential survival curves (FIGS. 4B and 4C). Hence, formulation of recipes for combined modality therapy should seek to use flow cytometry distribution information to identify the drug concentration that will achieve the first component of killing. A similarly optimized additional agent could then be added with the aim of targeting cells that had low uptake of the first drug. Successively adding additional drugs would ultimately seek to achieve a net heterogeneity of σ→0, based on incorporation of all agents. It should be noted that findings related to the distribution of therapeutic agents among a population of cells, and their corresponding dose response characteristics, may vary considerably depending on cell type and the microenviroment within which the cells reside. In addition, factors such as resistant subpopulations can have a significant impact on the shape of the response curve. Therefore, caution is needed when cocktails are formulated based on in vitro findings and then extrapolated to the in vivo setting encountered in the clinic.

The present invention demonstrates that the distribution of cellular radioactivity within a cell population is adequately described by a lognormal probability density function. The ubiquitousness of the lognormal distribution has been further demonstrated by the cellular uptake profiles of two different chemotherapeutic drugs. Changes in the value of the lognormal shape parameter and changes in the slope of the cellular uptake curves with increasing drug concentration flag the onset of saturation in the dose response curve. Accordingly, measurement of these changes using flow cytometry, or another analytical technique, preferably a high-speed technique, can be employed to rapidly predict biological response to the drug, and ultimately to formulate a highly effective therapeutic cocktail.

Cocktails of Therapeutic Agents

One multiple-therapeutic agent embodiment of the present invention involves a cocktail of radioimmunotherapy and chemotherapy agents. Informed radioimmunotherapy/chemotherapy is one option for front-line defense against metastatic and residual disease in adjuvant external beam radiotherapy and surgery. However, one major limitation has been the difficulty in relating cellular incorporation of therapeutic agents, on a cell-by-cell basis, to resulting biological effects. The models for predicting the distribution of cytotoxic agents among a cell population, at the single-cell level, as disclosed above, now also provide a cocktail approach whereby all malignant cells can be effectively targeted. This flow cytometry-based approach, taking explicit account of the lognormal distribution of cellular uptake of the agents, enables prediction of treatment response on a cell-by-cell basis, and has now been shown to be invaluable in the selection of agents for the design of highly effective therapeutic cocktails that are capable of targeting the diversity in tumor cell populations. Further, such cocktails can be created not only for treatment of cancer, but also for infectious diseases, and other diseases that are amenable to targeted therapies. Furthermore, this single-cell Monte Carlo technique can be used to resolve difficulties encountered when attempting to predict biological response at the multicellular level using macroscopic mean agent doses.

Over the past two decades, interest in the use of α-emitting radionuclides in radioimmunotherapy has grown significantly. However, a major unresolved concern is that the toxicity of α-emitting radionuclides does not allow administration of high activities. As such, targeting procedures would need to be optimized to minimize normal tissue toxicity. This can be achieved via multi-modality radioimmunotherapy, which employs combinations of radioimmunotherapy and chemotherapy. Multi-modality radioimmunotherapy approaches seek not only to effectively target all malignant cells, but also to significantly reduce the amount of each constituent of the cocktail. To guide design of effective cocktails of α-emitting radiopharmaceuticals and chemotherapy drugs, there is the need to assess the role of nonuniform agent distribution on modification of α-particle radiotoxicity by chemotherapy drugs. Furthermore, the capacity to predict such modifications in treatment response on a cell-by-cell basis should greatly improve treatment outcomes through individualized staging prior to therapy.

As has now been demonstrated, concomitant treatment of Chinese hamster V79 cells with an α-emitting radiochemical, $^{210}$Po-citrate, and either daunomycin or doxorubicin, resulted in an enhancement of α-particle radiotoxicity. Further, the toxicity of the combination treatment can be predicted with a Monte Carlo simulation approach based only on knowledge of the initial slope of the cell survival curves of the individual agents and information on the distribution of agent incorporation among cell populations.

Methods and Systems for Determining the Distribution of Radiation Dose and Response The present invention further includes the previously described methods that can be further included a system, method, and computer program product for clinical treatment planning for patients in need of nuclear medicine procedures, as well as chemotherapy procedures to treat cancer, and/or for diagnostic purposes. The present invention also allows users to visualize and understand the impact of radionuclide choice, distribution of activity (cross-dose) in and among cells (disease and normal), cell dimensions, inter-cell distances, cluster size, and radiobiological response parameters on the capacity to kill populations of cells. The data used to populate may be laboratory or patient data, and one with ordinary skill in the art may create additional features and/or incorporate patient data accordingly. Embodiments of the invention may include ten or more radiopharmaceutical and/or chemotherapy/biologic agents that can be simultaneously analyzed, by incorporating the methods previously described.

This disclosure is not limited to the particular systems, methodologies or protocols described, as these may vary. The terminology used in this description is for the purpose of describing the particular versions or embodiments only, and is not intended to limit the scope.

The following terms shall have, for purposes of this application, the respective meanings set forth below:

A "computing device" refers to a device that includes a processor and tangible, computing-readable memory. The memory may contain programming instructions that, when executed by the processor, cause the computing device to perform one or more operations according to the programming instructions. Examples of computing devices include personal computers, servers, mainframes, gaming systems, televisions, and portable electronic devices such as smartphones, personal digital assistants, cameras, tablet computers, laptop computers, media players and the like. When used in the claims, reference to "a computing device" may include a single device, or it may refer to any number of devices having one or more processors that communicate with each other and share data and/or instructions to perform the claimed steps.

An "application" refers to a software program that is configured to operate on a computing device. An application may assist a user in accessing network resources from a user's computing device, e.g., a mobile application may be linked to a database to receive parameters concerning a tissue sample from a patient.

A "mobile device" refers to a portable computing device. Examples of mobile devices include mobile phones, smartphones, personal digital assistants (PDA), tablet computers, e-readers or e-books, netbooks, notebook computers, and the like. A mobile device may include one or more input devices such as a keypad, a touch-pad, a track-pad, and a touch-sensitive component that is integrated within a display, such as a captive, resistive or other type of touch screen. A mobile computing device may be configured to access a communication network via a wired or wireless connection.

A "feature" refers to a unit of software, or a distinct section of a user interface, that displays a category or related group of information associated with at least a portion of an application.

An "option" refers to a visual feature of a graphical user interface. An option may be a button, a radio dial, a drop-down menu, a hyperlink, an icon, an image, a text box, a text field and/or the like.

The term "derive(d)" is used interchangeably with the term "calculate", and is generally used in reference to the calculation of a feature.

Figure 11:
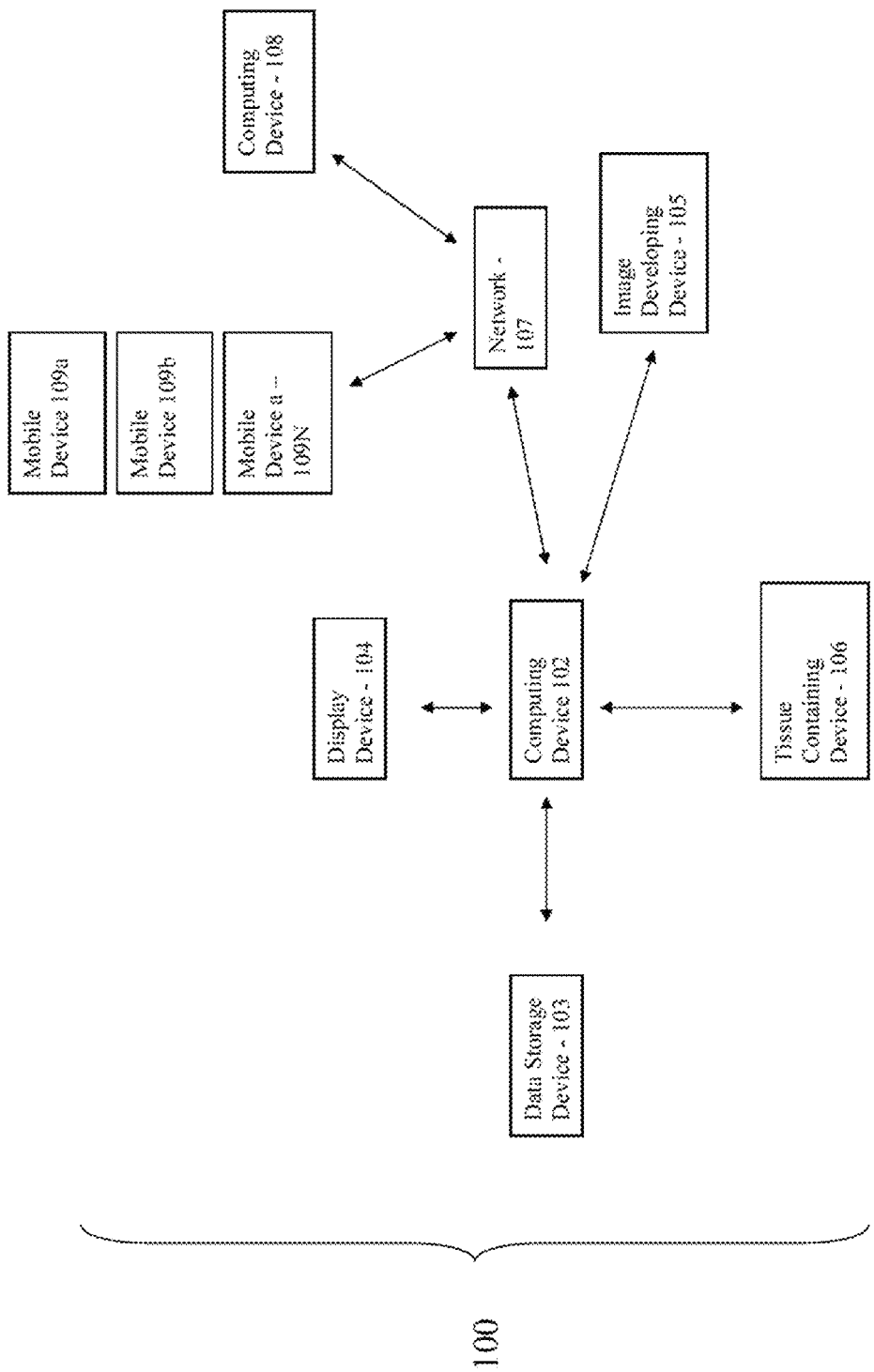
FIG. 11 illustrates a block diagram of an example system for determining a dose of radiation according to an embodiment.

FIG. 11 illustrates a block diagram of a system 100 for clinical treatment planning of a dose of radiation in accordance with the present invention. As illustrated by FIG. 1, the system 100 may include a computing device 102, a data storage device 103, a display device 104, an image developing device 105, and a device to contain tissue from a patient 106. A device to contain tissue from a patient 106 may provide certain parameters regarding the tissue, the tissue may be in the form of a histology slide with tissue, and the device may provide information regarding e.g. the type of cells and/or other parameters that would characterize the tissue sample. Examples of other devices that may acquire information from the tissue sample are flow cytometry, various types of mass spectroscopy devices, cDNA arrays, etc. A computing device 102 may be a computing device used to create an application as described herein. A computing device 102 may be in communication with a mobile device 109a-N and/or another computing device 108 via a communication network 107. In various embodiments, the communication network 107 may be a local area network (LAN), a wide area network (WAN), a mobile or cellular communication network, an extranet, an intranet, the Internet and/or the like. In an embodiment, the communication network 107 may provide communication capability between a computing device 102 and another computing device 108 or a mobile device 109a-N. Although FIG. 11 illustrates a single computing device 102, it is understood that the system 100 may include additional computing devices 102 within the scope of this disclosure. For clarity and brevity, in FIG. 11 a single system for determining a dose of radiation 100 is shown, but it should be understood that any number of systems for determining a dose of radiation may be accessed or connected by a communication network with which to perform methods in accordance with the invention.

The system 100 may include a computing device 102 configured to operate an application for determining a dose of radiation for a patient. The determination of the dose of radiation is made in accordance with configuration data and/or patient data.

In an embodiment, a computing device 102 or 108 may create an application based, at least in part, on information it receives from a computing device 102. The computing device 102 or 108 may make an application available to one or more mobile devices 109a-N. In an embodiment, a computing device 102 may be in communication with a mobile device 109a-N via a communication network 107.

Figure 12:
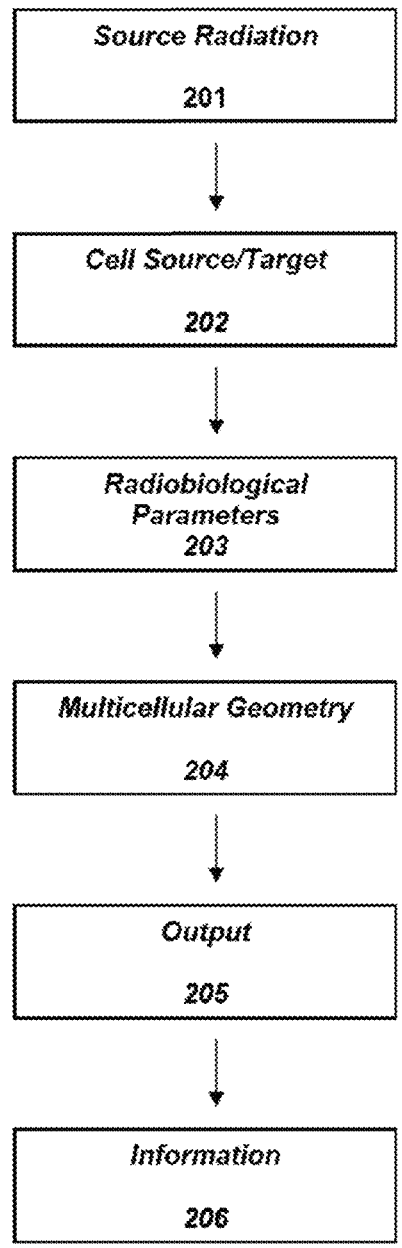
FIG. 12 illustrates a flow chart of an example for a method of determining a dose of radiation according to an embodiment for an application.

FIG. 12 illustrates a flow chart of an example method of determining a dose of radiation according to an embodiment by a computing device and/or an application of a computing device or a mobile device.

Figure 13:
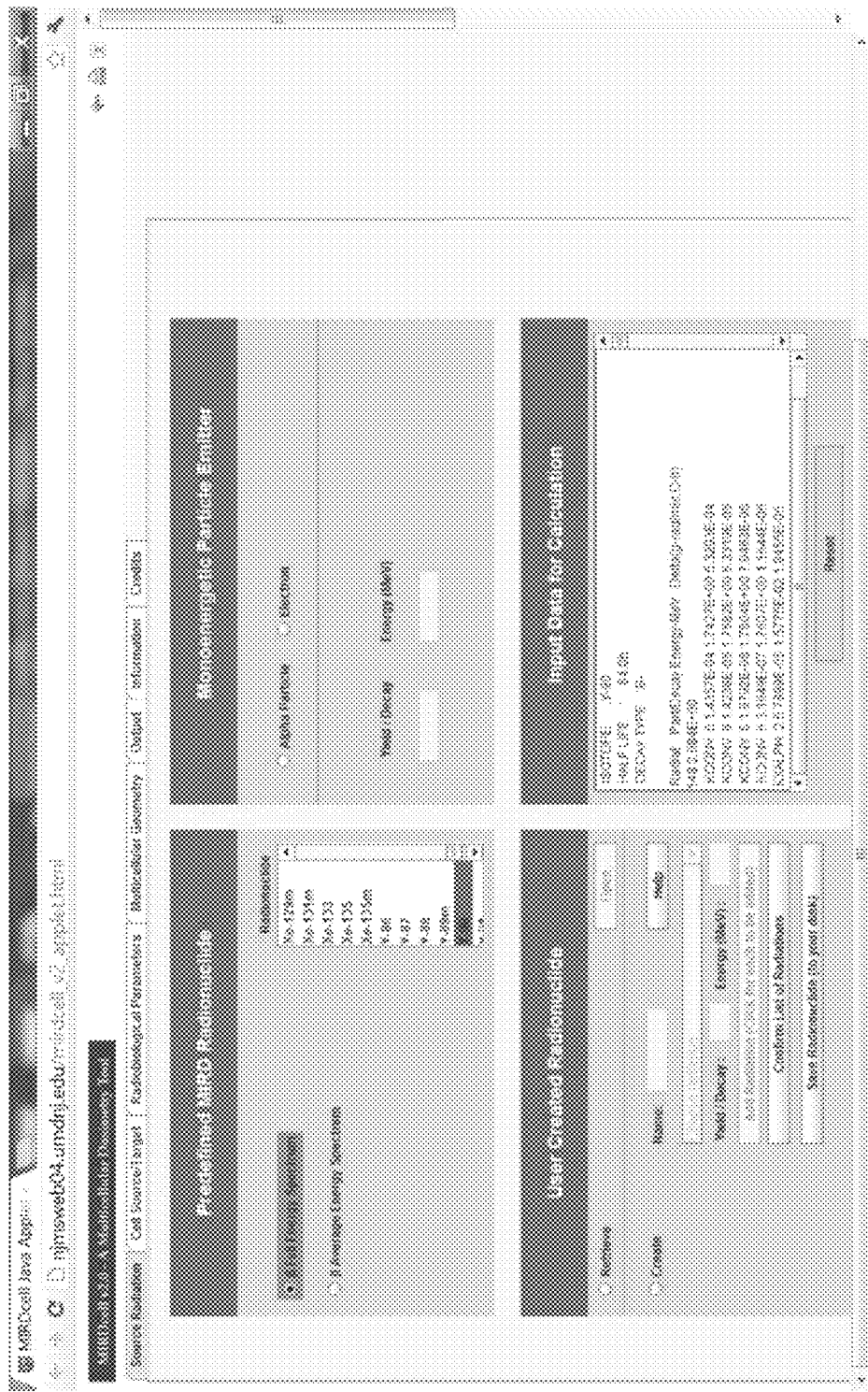
FIG. 13 illustrates an example graphical user interface (GUI) of the Source Radiation feature. This feature provides three major options for selecting the type of radioactivity to be placed in the labeled cells: 1) Predefined MIRD Radionuclide (upper left). Radiation spectra are available for predefined radionuclides that include either average beta particle energies (β Average Energy Spectrum) or the complete beta particle spectrum (β Full Energy Spectrum). 2) Monoenergetic Particle Emitter (upper right). Here, the user can select either an alpha particle or electron, and specify the particle yield per disintegration and energy. 3) User-Created Radionuclide (lower left). The user can create a radionuclide that includes a variety of selectable radiations (alpha, Auger electron, beta minus, and beta plus). Once the radionuclide is selected, its corresponding data are streamed into the lower right box entitled Input Data for Calculation, that a user may use to create a new application according to an embodiment.

FIG. 13 illustrates a GUI for a Source Radiation 201 feature. This feature allows a user to select the radioactivity in the source cells (i.e. cells labeled with radioactivity). Upon making a selection, the radiation data may be shown in a field such as the box entitled Input Data for Calculation. In an embodiment as shown in Table 1, two or more choices may be available. The choices may include: Predefined MIRD radionuclide, Monoenergetic Particle Emitter and user-defined radionuclide. This feature may also include the background dose for low-LET or high-LET radiation. In a further embodiment, this feature or a new similar feature may include a time-factor in dose response function, account for different radiation types and/or provide distribution of biologically effective doses (BED) and equieffective doses (EQD2).

In other embodiments, this feature or a new feature can include other types of agents, such as chemotherapeutic and/or biologic drugs to treat a condition such as cancer or an infection, and may further include parameters for physical half-life, biological half times, pharmacokinetic and/or phamacodynamic data regarding the agents.

In an embodiment, there may be two or more options within the Predefined MIRD Radionuclide. The "β Full Energy Spectrum" option provides a dropdown list of the radionuclides for which data are provided in the MIRD Radionuclide Decay Scheme monograph. In an embodiment, data sets correspond to the radiation data from which the monograph was prepared; however, the yield and mean energies for all beta particle (β−) and positron (β+) emitters maybe replaced with full logarithmically binned β spectra. Use of the continuous β spectrum as opposed to the mean β energy can play an important role in cellular dosimetry. This altered data set was originally created for calculating cellular S values in the MIRD Cellular S Values monograph. Some of the spectra contained in excess of one thousand different radiations for a given radionuclide, many of which are insignificant with respect to internal dosimetry, in certain embodiments, radiations which contributed greater than 0.1% to the total energy emitted per nuclear transformation (Δ) for that particular radiation type may be retained. Recoil energy of the residual daughter following alpha decay may not be included because experiments indicate that this energy is not biologically relevant. The "β Average Energy Spectrum" option provides the radiation data contained on the compact disk that accompanies the MIRD Radionuclide Decay Scheme 2nd Edition. In certain embodiments, average β particle energies may be contained within this data set.

In regards to radionuclides that are part of a decay chain (e.g. 211 At, 213Bi, 223Ra, 225Ac) parent and daughter radionuclides may not be in equilibrium due to differences in biokinetics behavior. In certain embodiments, users can create files that include daughters provided that branching ratios are accounted for and should be done when the parent and daughter radionuclides are in equilibrium.

The "Monoenergetic Particle Emitter" option allows a user to select a hypothetical monoenergetic electron or alpha particle emitter. Particle energy and yield per nuclear transformation may be specified by a user.

The "User Created Radionuclide" option provides maximum flexibility by allowing the user to create a radionuclide that is not available in the predefined dropdown lists. After specifying the name of the radionuclide, the user may choose a radiation type, its yield and energy, and then selects "Add Radiation." This process is repeated until all desired radiations have been added. "Confirm List of Radiations" is then selected. If it is desired to save the radionuclide for later use, "Save" may be selected and it may be saved to a local storage location.

Finally, once the user selects the desired radionuclide from one of the three exemplified options above, the radiation data is calculated and exemplified in the box entitled Input Data for Calculation. Specified in descending order are the radionuclide, physical half-life, and principal decay type. This is followed by the radiation data for the radionuclide; these include the total number of radiations in the file and the radiation type, yield, energy, and mean energy emitted per nuclear transition for each radiation $\Delta_i$.

Figure 14:
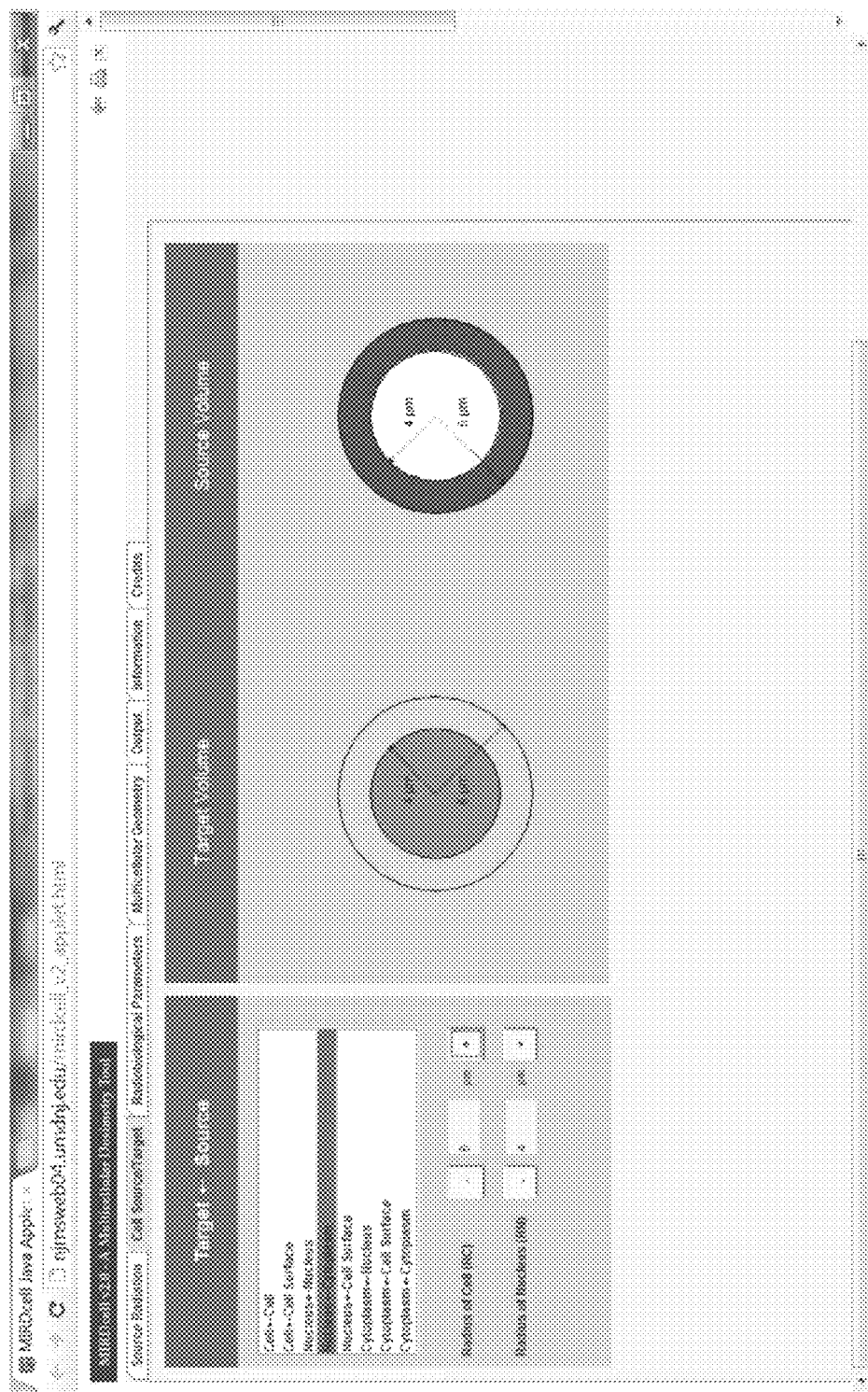
FIG. 14 illustrates an example GUI of a Cell Source/Target feature. The source region (red/dark grey) in the cell that contains the radiopharmaceutical can be selected as cell, cell surface, nucleus, or cytoplasm (top left). Selectable target regions (blue/light grey) include cell, nucleus, or cytoplasm (top left). The cell and cell nucleus are represented by concentric shells of unit density water with cell radius ($R_C$) and cell nucleus radius ($R_N$), which can be set as desired (bottom left). The selections made by the user are then depicted (right) that a user may use to identify one or more features associated with an application according to an embodiment.

FIG. 14 illustrates a GUI for a Cell Source/Target feature 202. This feature allows a user to select source volume in cell where radioactivity is distributed. Select target volume in the cell for which radiation absorbed dose will be calculated. Select radius of cell and nucleus. The cell is modeled as two concentric spheres with radii corresponding to those for the nucleus ($R_N$) and cell ($R_C$), respectively, however additional models that take into account the cell membrane or other regions of a cell can be implemented. The cells are assumed to be composed of liquid water of unit density. The radioactivity in the cell is assumed to be uniformly distributed in the source region of the cell; selectable among cell (C), cell nucleus (N), cytoplasm (Cy), or cell surface (CS). In certain embodiments, the target region in the cell for which the radiation absorbed dose will be calculated, can be selected for example, as the entire cell, the cell nucleus and/or the cell membrane. The radii of the cell and cell nucleus may be limited to integer values and are specified by a user.

In another embodiment, the Cell Source/Target feature may contain or import patient or laboratory data regarding the target cells or diseased tissue of a patient. The patient or laboratory data may be imported through a network. This feature or an additional feature may also take into consideration the bystander effect.

Figure 15:
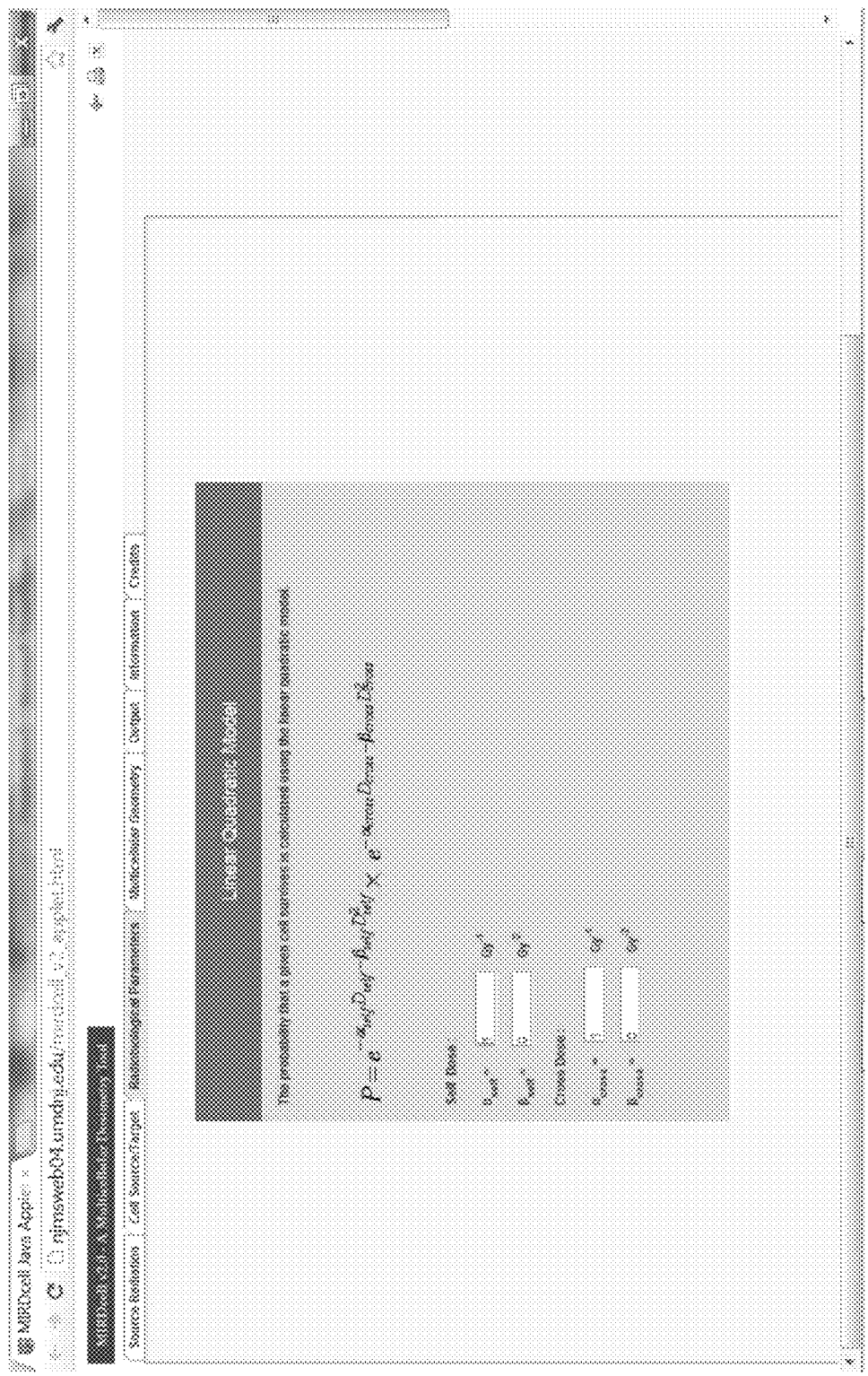
FIG. 15 illustrates an example GUI of a Radiobiological Parameters feature. The self-dose and cross-dose is tallied for each cell in the multicellular geometry. The probability that a given cell survives is calculated using the linear quadratic model. The responses to self-dose and cross-dose can be set independently using the parameters $\alpha_{self}$, $\beta_{self}$ and $\alpha_{cross}$, $\beta_{cross}$, respectively.

FIG. 15 illustrates a GUI for a Radiobiological Parameters feature 203. This feature allows a user to model the surviving fraction of cells in a specified cell population based on the calculated absorbed doses to the individual cells (see subsections that follow). The probability P that a given cell survives is calculated with the linear quadratic model (Eq. 1), $$P = e^{-\alpha_{self}D_{self} - \beta_{self}D_{self}^2} \times e^{-\alpha_{cross}D_{cross} - \beta_{cross}D_{cross}^2} \qquad (1)$$

Where $\alpha_{self}$ and $\beta_{self}$ are the linear-quadratic parameters that characterize the cellular response to self-dose ($D_{self}$) and $\alpha_{cross}$ and $\beta_{cross}$ characterize the cellular response to cross-dose ($D_{cross}$). This distinction can often be necessary for Auger electron emitters, or even beta particle emitters, when they are incorporated into the DNA. Under these circumstances, the relative biological effectiveness of Auger emitters can be akin to alpha particles. The default parameters are set to $\alpha_{self} = \alpha_{cross} = 1$ Gy$^{-1}$, and $\beta_{self} = \beta_{cross} = 0$ Gy$^{-2}$. These default values are arbitrary and a user may use values that are relevant to their use of the application. The Monte Carlo method can be used to determine whether a given cell survives. This feature may also enable assessment of the surviving fraction of a population of small multicellular clusters. This additional embodiment may allow a user to select the number of clusters and distribution of cluster sizes. This feature or an additional feature may take into consideration the bystander effect.

Figure 16:
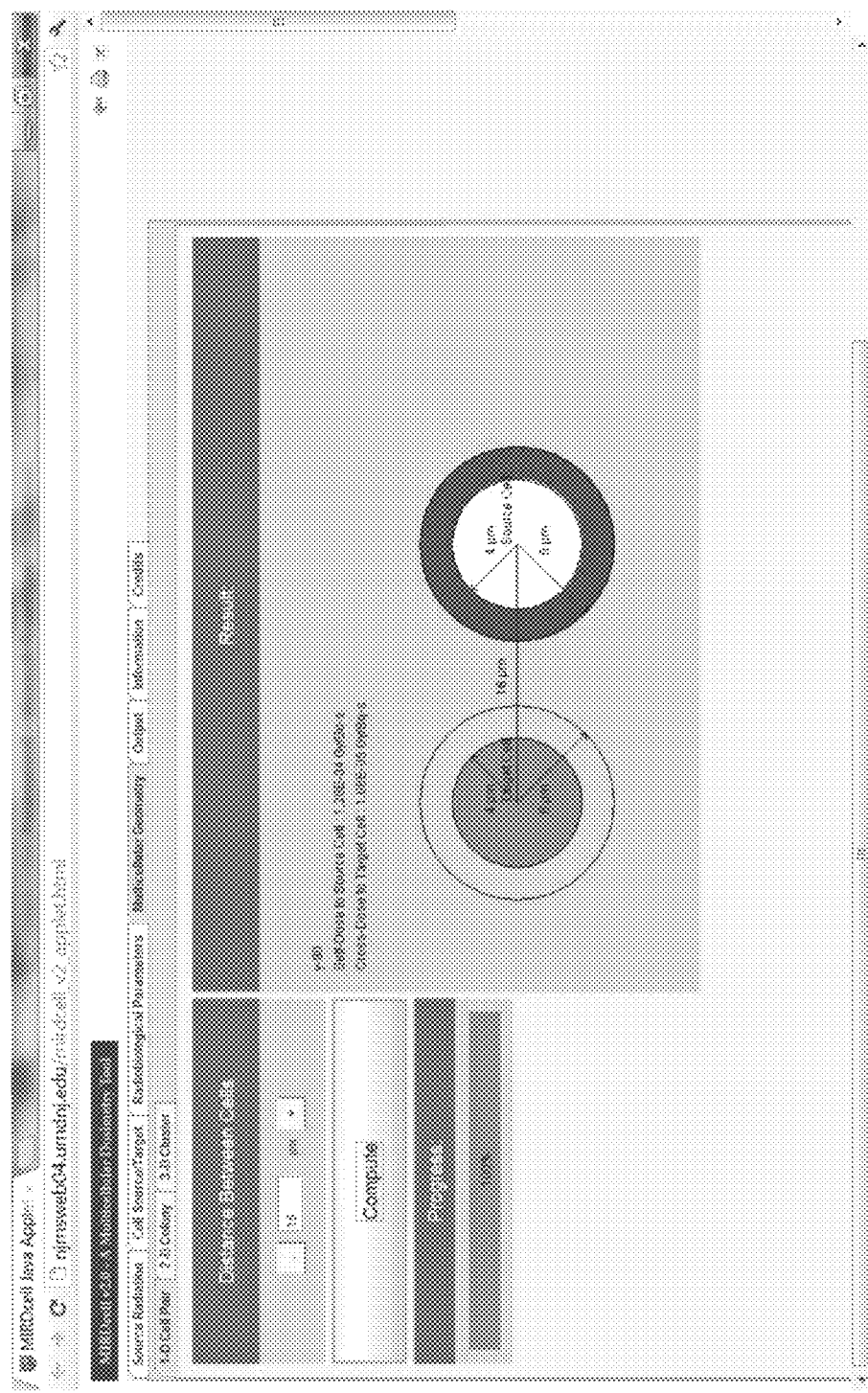
FIG. 16 illustrates an example GUI of a Multicellular Geometry<1-D Cell Pair sub-feature. This sub-feature enables rapid calculation of the self-dose to a labeled cell and cross-dose to a neighboring cell that lies at some distance (i.e. 16 μm between centers in this example). The self- and cross-doses per unit cumulated activity in the source cell (Gy $Bq^{-1}$ $s^{-1}$), also known as S value, are reported for the selected source radiation (i.e., Y-90 in this example) in the box labeled Result. The calculation can be repeated for different cell separation distances (top left).

FIG. 16 illustrates a GUI for a Multicellular Geometry feature 204. Within the Multicellular Geometry feature, a user may input the activity distribution, or select the activity distribution provided by a computing device, a data storage device, an image developing device or a tissue containing device. Multicellular Geometry<1-D cell Pair sub-feature. FIG. 16 depicts the cell geometry that is used to calculate the self- and cross-doses for a pair of cells. This configuration is considered 1-dimensional (1-D). The source volume that contains radioactivity is generally defined by a color such as the color red. The target volume in the neighboring cell is also generally defined by a color such as the color blue. The user may set the distance (d) between the centers of two cells that are nearest neighbors. The self-dose and cross-dose S values (mean absorbed dose per unit cumulated activity in the source region) for the specified source and target regions are calculated upon selecting a (Compute button. The self-dose and cross-dose S values are calculated using stopping powers and geometric factors (*J Nucl Med.* 1994; 35:303-316 and *J Nucl Med.* 1994; 35:521-530). As in the MIRD Cellular S value monograph, the stopping power relationship of Cole may be used for electrons and alpha-particle stopping powers from reports of the International Commission on Radiation Units and Measurements. Also, Also, Monte Carlo radiation transport codes are available for low-energy Auger electron emitters such as $^{125}$I localized on the cell surface or cytoplasm. In principle, stopping power data from other literature could be used. In addition, stopping power data for media other than water could also be used.

Figure 17A:
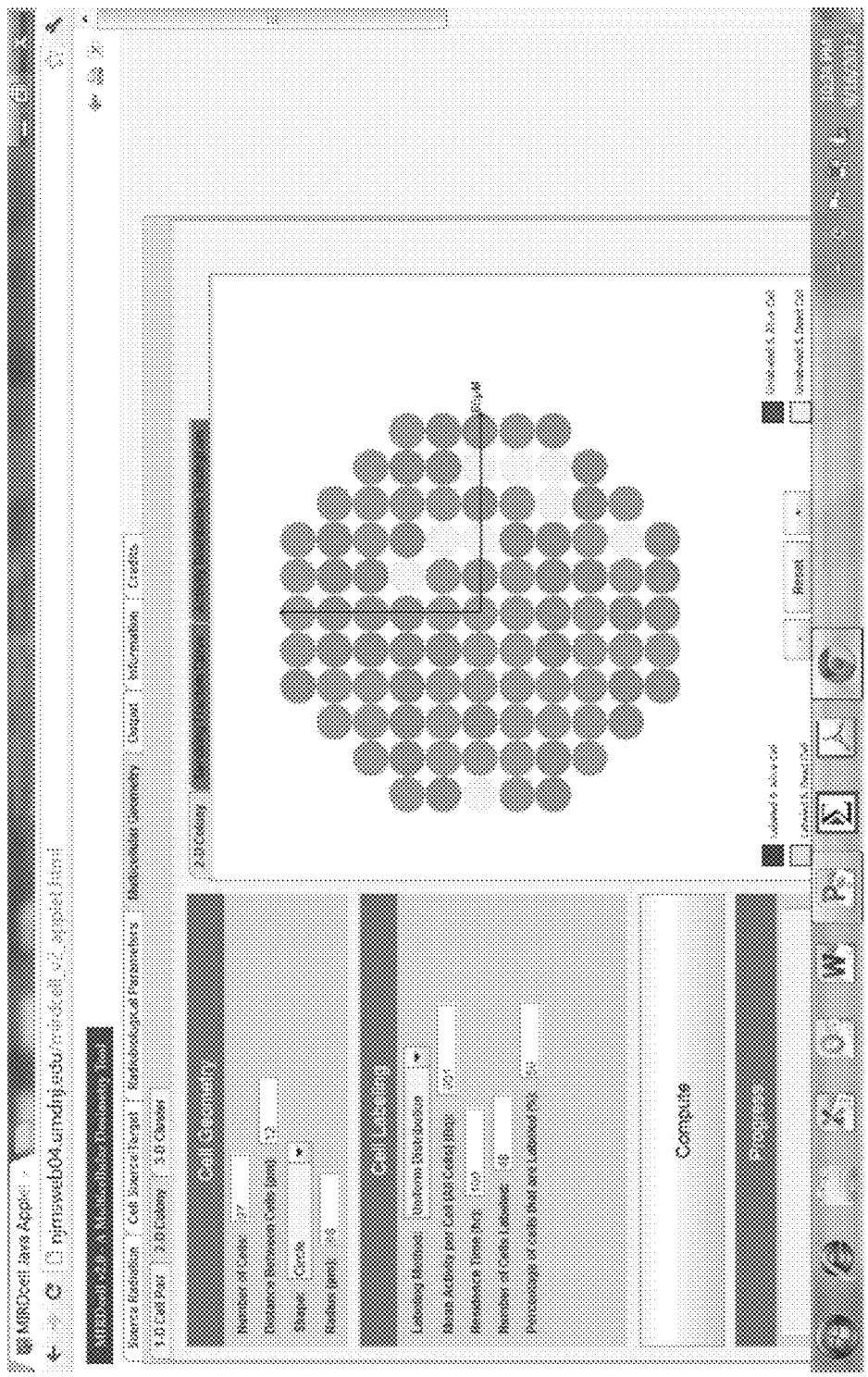
FIG. 17A illustrates an example GUI of a Multicellular Geometry<2-D Colony<2-D Colony sub-feature. The user can select a multicellular geometry wherein the cell population lies on a plane. In the Cell Geometry box, the cell population can be constrained to different selectable shapes including circle (shown), ellipse, and rectangle (upper left). Dimensions of each shape are provided by the user (i.e. circle with 66 μm radius in this example). In the Cell Labeling box, the activity can be distributed amongst the cell population according to selectable labeling methods: uniform (shown), normal, and lognormal. The mean activity per cell, residence time, and percentage of cells that are labeled can be specified. Upon selecting parameters and selecting Compute, the resulting multicellular geometry is plotted on the right in a manner that indicates whether a cell is labeled (red/dark grey) or unlabeled (green/light grey), and the transparency represents whether the cell is dead (transparent) or alive (opaque), an example analytic chart according to an embodiment.
Figure 17B:
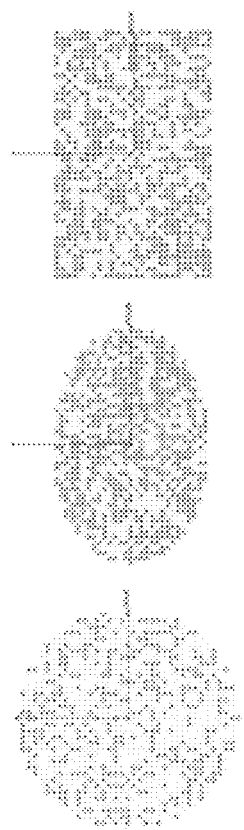
FIG. 17B illustrates an example GUI of additional geometries available in Multicellular Geometry<2-D Colony<2-D Colony. These are 2-D Colony shapes containing 1000 cells, with 50% of the cells labeled with Y-90. Circular, ellipsoidal, and rectangular colony shapes are shown as examples. Cells are labeled (red/dark grey) or unlabeled (green/light grey), and the transparency represents whether the cell is dead (transparent) or alive (opaque).

FIG. 17A illustrates a GUI for a Multicellular Geometry<2-D Colony<2-D Colony, another sub-feature, within the Multicellular Geometry feature. This sub-feature is used to create a cell population that resides on a plane (i.e. colony). It is preferable that the application contain a Cell Geometry box, to allow a user to specify the number of cells in the colony, distance between the cells, and the shape and dimensions of the colony (circle, rectangle, ellipse, as shown in FIG. 17B). Alternatively, the shape can be selected first and then the dimensions of the colony can be specified. It is preferable that the application contain a Cell Labeling box, a user may select the distribution of activity among the labeled cell population (uniform, normal, lognormal) and enter the standard deviation of the mean for the normal distribution or shape factor for the lognormal distribution. A uniform activity distribution among the labeled cells implies that each labeled cell has the same initial activity A in its source region. In the normal distribution, the initial activity per cell is distributed according to the probability density function:

$$f(A) = \frac{1}{A\sigma\sqrt{2\pi}} e^{\frac{-(A-<A>)^3}{2\sigma^3}} \quad (2)$$

Where <A> is the mean initial activity per cell and σ is the standard deviation of the mean. It is preferable that a user avoid entering standard deviations that can result in negative values of A. When this occurs, the user is prompted to choose a smaller value for σ. In the case of the lognormal distribution, the activity per cell is distributed according to the probability density function:

$$f(A) = \frac{1}{A\sigma\sqrt{2\pi}} e^{\frac{-(\ln A - (\ln <A> - \sigma^2/2))^2}{2\sigma^2}}, A > 0 \quad (3)$$

where σ is the lognormal shape parameter. Thus, if <A> is known experimentally, then only σ is required. Mean Activity per Cell (labeled+unlabeled) and time-integrated activity coefficient (ã) are then entered. The time integrated activity coefficient (also known as the cumulated activity) is defined in MIRD Pamphlet No. 21. A user may then specify either the Number of Cells Labeled with radioactivity or the Percentage of cells that are Labeled. Once all the parameters are specified the user instructs the computing device to calculate the inputted variables to derive a Multicellular Geometry and its biological response. Calculation times may vary dramatically depending on the number of radiations emitted by the selected radionuclide, the range of the particles emitted, and the percentage of cells that are labeled. A progress bar appears below the Compute button to provide the status of the calculation. Progress for Part 1 corresponds to the calculation of all necessary self- and cross-dose S values. Progress for Part 2 corresponds to the process of creating a virtual assembly of cells in a Cartesian coordinate system with a close packed square lattice (number of cells is displayed), assigning activity to each cell, tallying self- and cross-doses for each cell, calculating the surviving fraction of cells (see below), and plotting the colony geometry in the graphical user interface. Labeled cells are selected randomly and each cell randomly assigned an initial activity according to user-selected distribution. The time integrated activity in the source compartment of each cell is calculated by taking the product of the initial activity in the cell and the user-specified time-integrated activity coefficient (ã). The activity in all labeled cells is assumed to have the same residence time.

In another embodiment, the activity distribution can be predicted based on input from devices that analyze patient samples. For example, as described in the literature (J. M. Akudugu and R. W. Howell, A method to predict response of cell populations to cocktails of chemotherapeutics and radiopharmaceuticals: Validation with daunomycin, doxorubicin, and the alpha particle emitter $^{210}$Po. Nucl Med Biol 39, 954-961 (2012)), flow cytometry can be used to determine the distribution of drug uptake of one or more drugs among the cell population. The methods previously described to determine to predict an individual patient's cells may be incorporated into this or an additional related feature. Each of these drugs can be labeled with radioactivity so the activity distribution for each is known. Each of these drugs can be labeled with radioactivity so the activity distribution for each is known. These data can then be used to calculate the self- and cross-dose to each cell in the population analogous to the description above. High throughput methods that quantify drug targets on a cell-by-cell basis can also be used to provide input information. Finally, in another embodiment, both nonradioactive drugs and radioactive drugs can be analyzed to obtain the optimum therapeutic cocktail.

Figure 18:
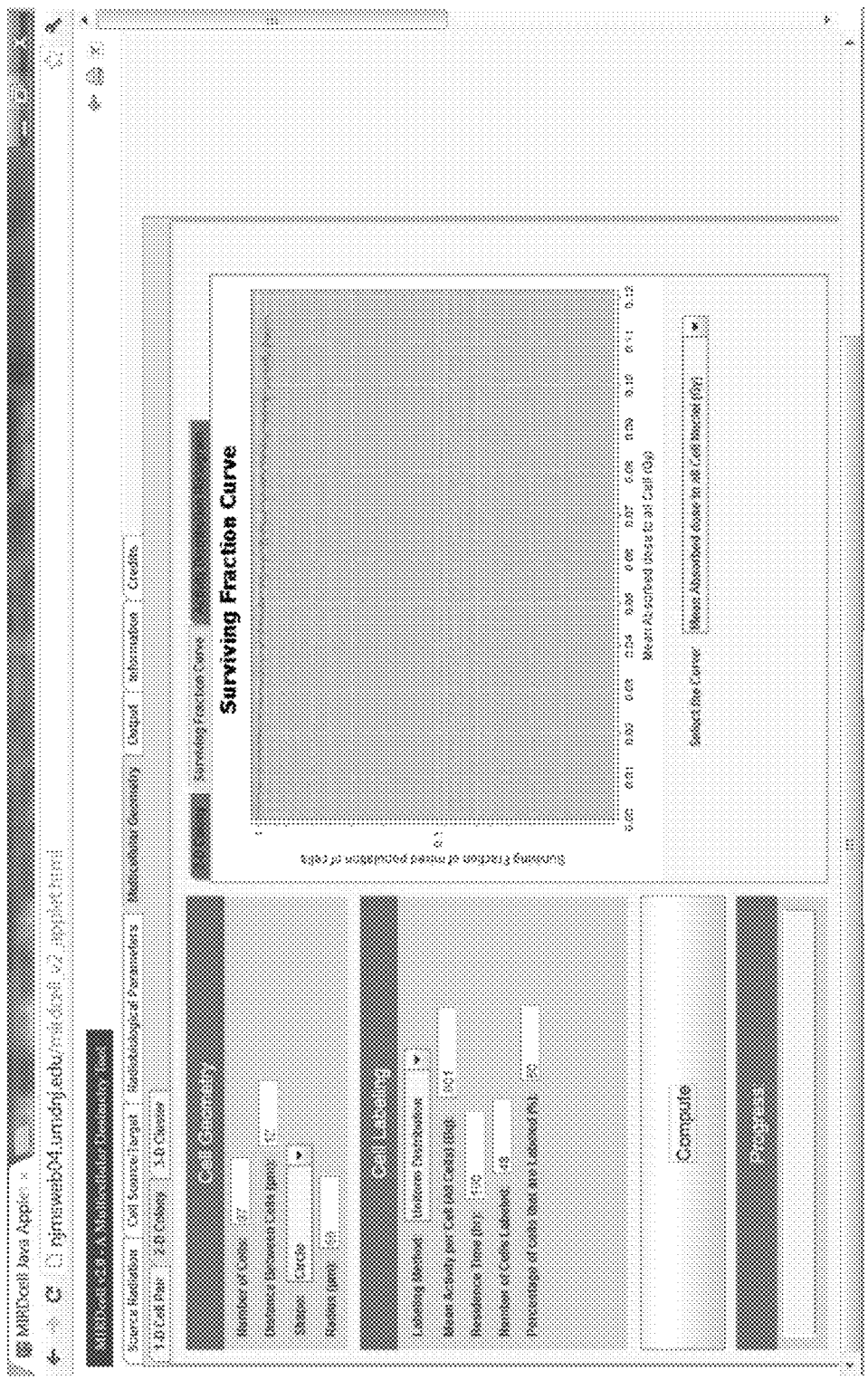
FIG. 18 illustrates an example GUI of a Multicellular Geometry<2-D Colony<Surviving Fraction Curve. Selecting the Surviving Fraction Curve sub-feature provides a survival curve for the cell population under consideration based on entries in the tabs. Using the drop-down menu labeled "Select the Curve", located below the abscissa, three different plots are available: 1) Surviving fraction of mixed population of cells versus mean absorbed dose to all cell nuclei, 2) Surviving fraction of labeled cells versus mean absorbed dose to labeled cells, and 3) Surviving fraction of unlabeled cells versus mean absorbed dose to unlabeled cells.

FIG. 18 illustrates a GUI for a Multicellular Geometry<2-D Colony<Surviving Fraction sub-feature within the Multicellular Geometry feature. A user may instruct the computing device to calculate and derive the surviving fraction of cells in the colony. The surviving fraction is calculated using the Monte Carlo method. For each cell, a survival probability is calculated by substituting its self- and cross-dose into Equation 1. A random number between 0.0 and 1.0, which may be generated with Java method Math.random, is compared with the survival probability. If the random number was smaller than the generated probability, the cell was scored as a survivor. Otherwise, it is scored as dead (i.e., having undergone reproductive failure). The fraction of survivors among the cell population that compose a given simulation represents the surviving fraction of the cell population. This process is repeated for numerous values of <A> up to a maximum value corresponding to the user assigned mean activity per cell. The resulting surviving fractions are plotted as a function of cellular activity or absorbed dose to the labeled, unlabeled, and entire cell population according to user-selectable ordinates and abscissae. These choices allow the user to explore characteristics of the response of each population of cells. In general labeled cells receive both self- and cross-doses, whereas unlabeled cells receive only cross-dose.

Figure 19A:
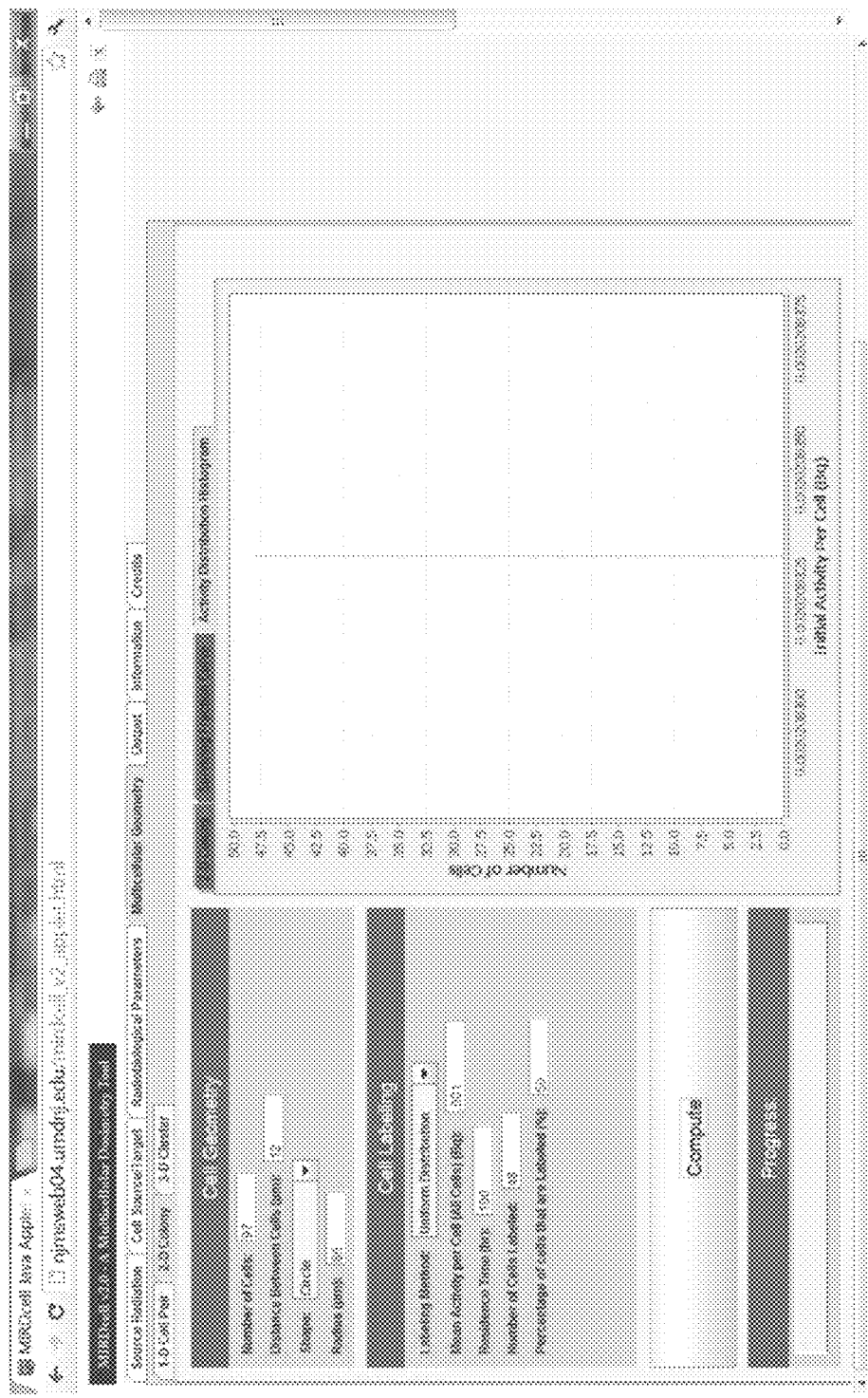
FIG. 19A illustrates an example GUI of a Multicellular Geometry<2-D Colony<Activity Distribution Histogram. Selecting the Activity Distribution Histogram sub-feature provides the distribution of activity among the labeled cell population under consideration based on entries in the sub-feature. This example shows a uniform distribution of activity among the labeled cells (each labeled cell has same activity).

FIG. 19A illustrates a GUI for a Multicellular Geometry<2-D Colony<Activity Distribution Histogram sub-feature. The user-specified activity distribution is plotted in this feature. Data for this feature can be imported from laboratory or patient data.

Figure 19B:
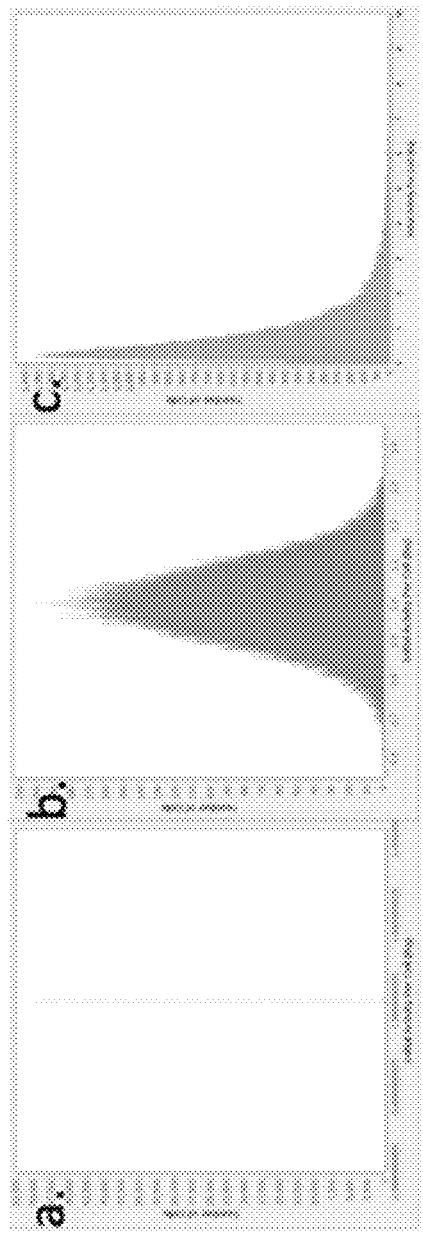
FIG. 19B illustrates examples of the different cellular activity distributions that can be selected. Initial activity histogram for labeled cells: a) Uniform Distribution, b) Normal Distribution with mean activity per cell equal to 1 Bq and standard deviation equal to 0.1 Bq, c) Lognormal Distribution with mean activity per cell equal to 1 Bq and shape factor equal to 1. These distributions are also available in the 3-D Cluster.

FIG. 19B illustrates examples of uniform, normal and lognormal distributions. Initial activity histogram for labeled cells: a) Uniform Distribution, b) Normal Distribution with mean activity per cell equal to 1 Bq and standard deviation equal to 0.1 Bq, c) Lognormal Distribution with mean activity per cell equal to 1 Bq and shape factor equal to 1. These distributions are also available in the 3-D Cluster.

Figure 20A:
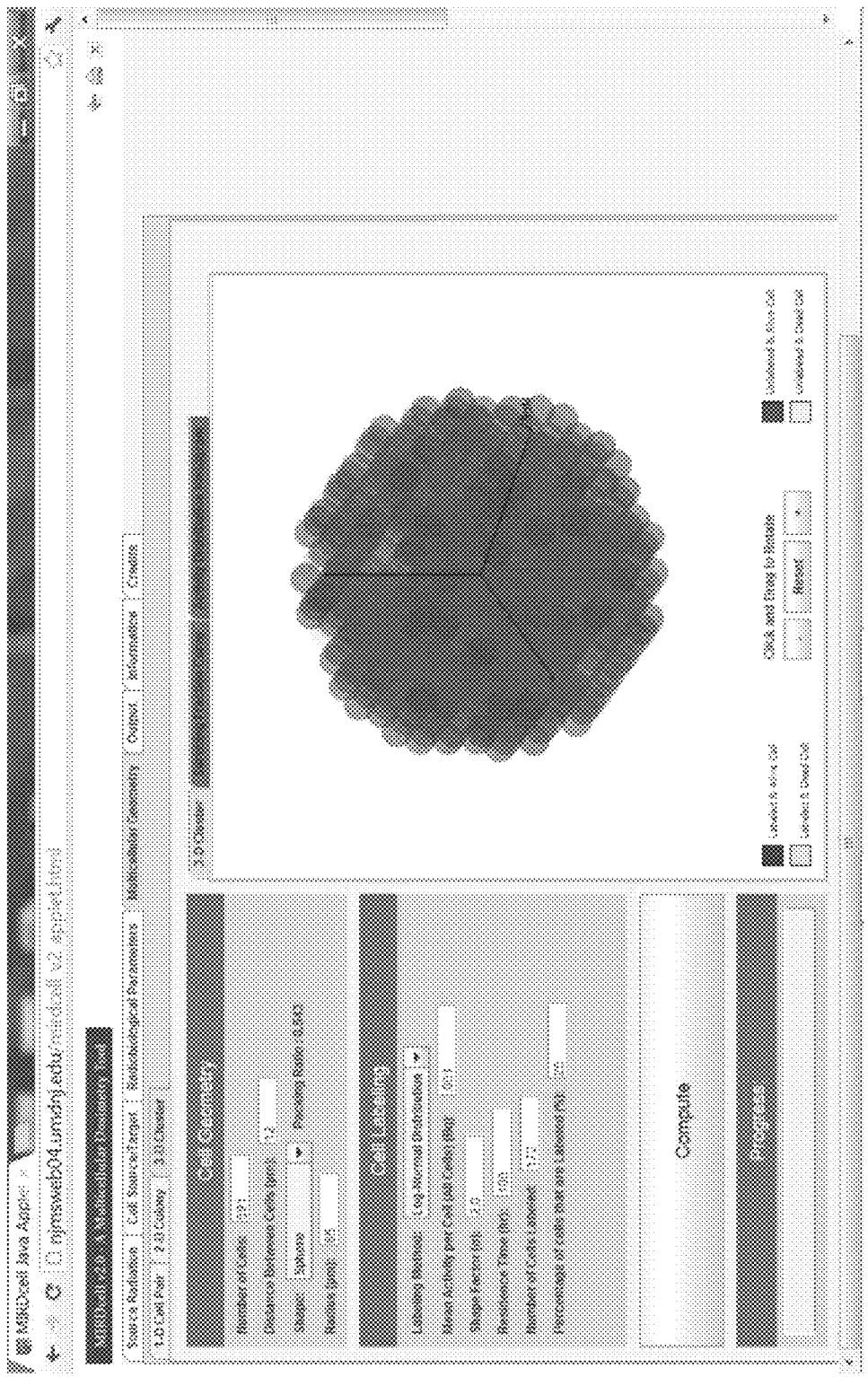
FIG. 20A illustrates an example GUI of a Multicellular Geometry<3-D Cluster<3-D Cluster. Here, the user can select a multicellular geometry wherein the cell population is contained within a three-dimensional geometry. In the Cell Geometry box, the cell population can be constrained to different selectable shapes including sphere (shown), ellipsoid, and cone. Dimensions of each shape are provided by the user (i.e. sphere with 65 μm radius in this example). In the Cell Labeling box, the activity can be distributed amongst the cell population according to selectable labeling distributions: uniform, normal, and lognormal (shown). The mean activity per cell, residence time, and percentage of cells that are labeled can be specified. Upon selecting parameters and selecting "Compute", the resulting multicellular geometry is plotted on the right in a manner that indicates whether a cell is labeled (red/dark grey) or unlabeled (green/light grey), and the transparency represents whether the cell is dead (transparent) or alive (opaque).
Figure 20B:
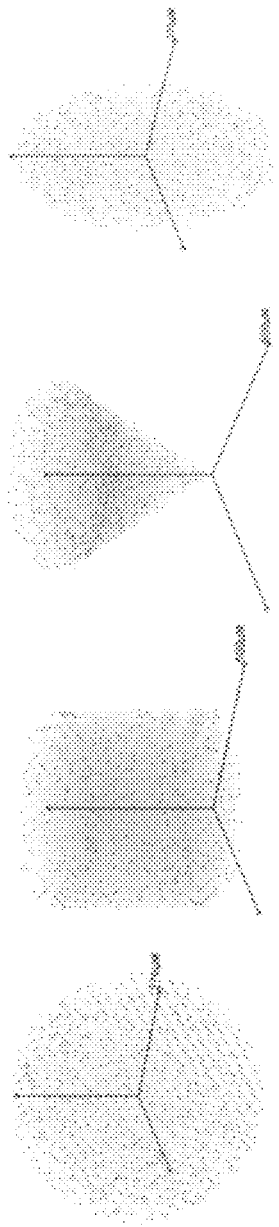
FIG. 20B illustrates examples of additional geometries available in Multicellular Geometry<3-D Cluster<3-D Cluster. These are 3-D Cluster shapes containing 10000 cells, with 50% of the cells labeled with Y-90, a user may define the amount of cells per cluster, several to in excess of 100,000 cells. Cluster shapes are Sphere, Rod, Cone, and Ellipsoid. Cells are labeled (red/dark grey) or unlabeled (green/light grey), and the transparency represents whether the cell is dead (transparent) or alive (opaque).

FIG. 20A illustrates a GUI for a Multicellular Geometry<3-D Cluster<3-D Cluster sub-feature. The planar cell configuration described above may be extended to three dimensional clusters as shown in FIG. 20A. The user may select the shape of the cluster to be a sphere, ellipsoid, rod, or cone, or other shapes that a user may define for an application (FIG. 20B). The desired dimensions of the cluster are then entered along with the time-integrated activity coefficient (ã), mean activity per cell (labeled+unlabeled cells), and number or percentage of cells labeled. The user instructs the computing device to calculate and derive a Multicellular Geometry<3-D Cluster e.g. by selecting for example, a Compute button, the simulation and modeling begin. The process is essentially the same as for the 2-D Colony except that the cluster is assembled in a three-dimensional Cartesian coordinate system in a close-packed cubic lattice. Other embodiments could use different cell packing configurations (e.g. hexagonal close packed). Varying cell diameters and shapes could be supported in yet another embodiment, and data for this feature can be imported from laboratory or patient data.

FIG. 20B illustrates examples of additional geometries available in Multicellular Geometry<3-D Cluster<3-D Cluster. These are 3-D Cluster shapes containing 10000 cells, with 50% of the cells labeled with Y-90, a user may define the amount of cells per cluster, several to in excess of 100,000 cells. Cluster shapes are Sphere, Rod, Cone, and Ellipsoid. Cells are labeled (red/dark grey) or unlabeled (green/light grey), and the transparency represents whether the cell is dead (transparent) or alive (opaque).

Figure 21:
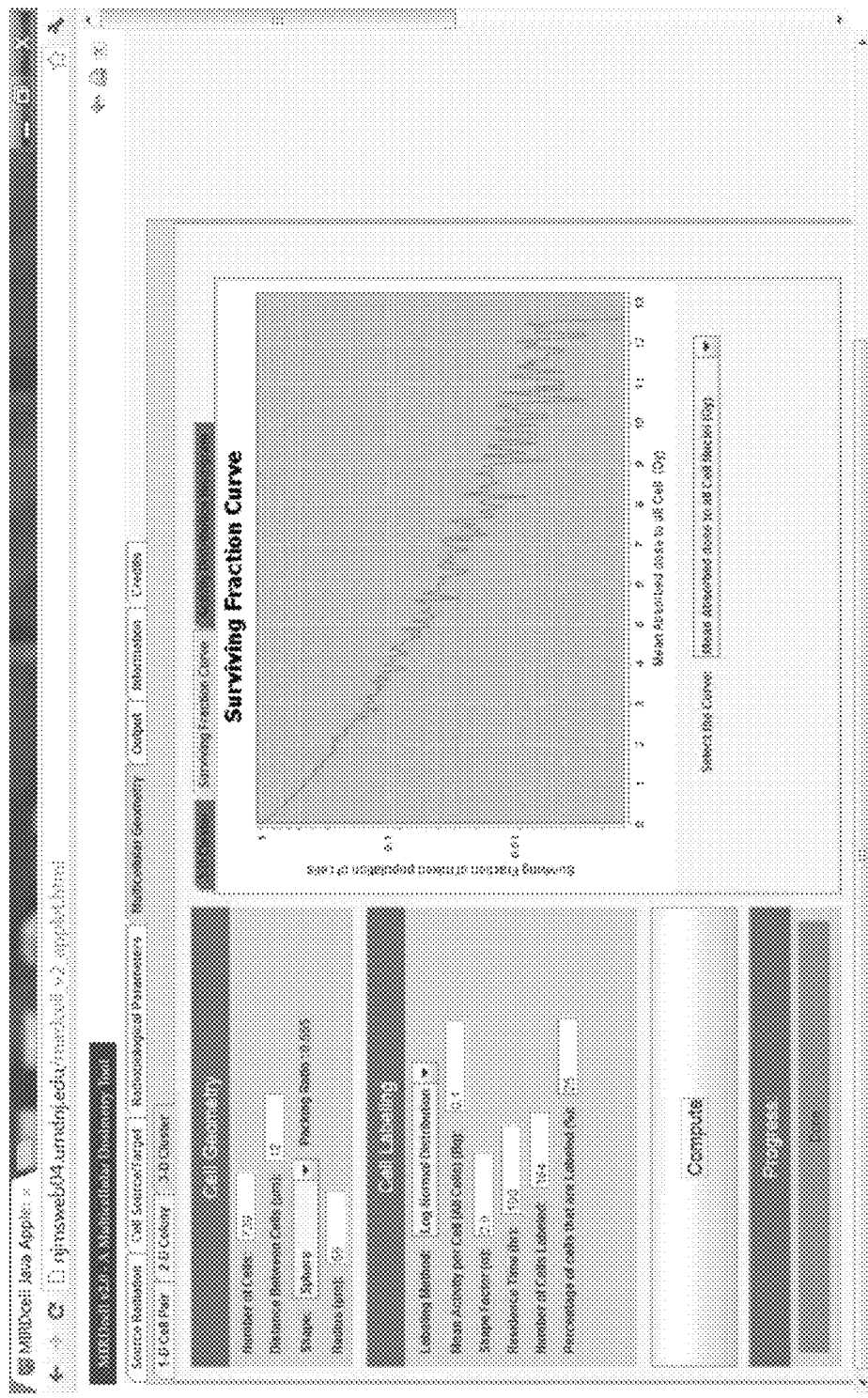
FIG. 21 illustrates an example GUI of a Multicellular Geometry<3-D Cluster<Surviving Fraction Curve. Selecting the "Surviving Fraction Curve" sub-feature provides a survival curve for the cell population under consideration based on entries in the sub-feature. Using the drop-down menu labeled "Select the Curve", located below the abscissa, three different plots are available: 1) Surviving fraction of mixed population of cells versus mean absorbed dose to all cell nuclei, 2) Surviving fraction of labeled cells versus mean absorbed dose to labeled cells, and 3) Surviving fraction of unlabeled cells versus mean absorbed dose to unlabeled cells.

FIG. 21 illustrates a GUI for a Multicellular Geometry<3-D Cluster<Surviving Fraction sub-feature (FIG. 21). As in the 2-D colony case, a user may instruct the computing device to calculate and derive a Multicellular Geometry<3-D Cluster<Surviving Fraction e.g. also calculated upon selecting the Compute button.

Figures 9A, 9B:
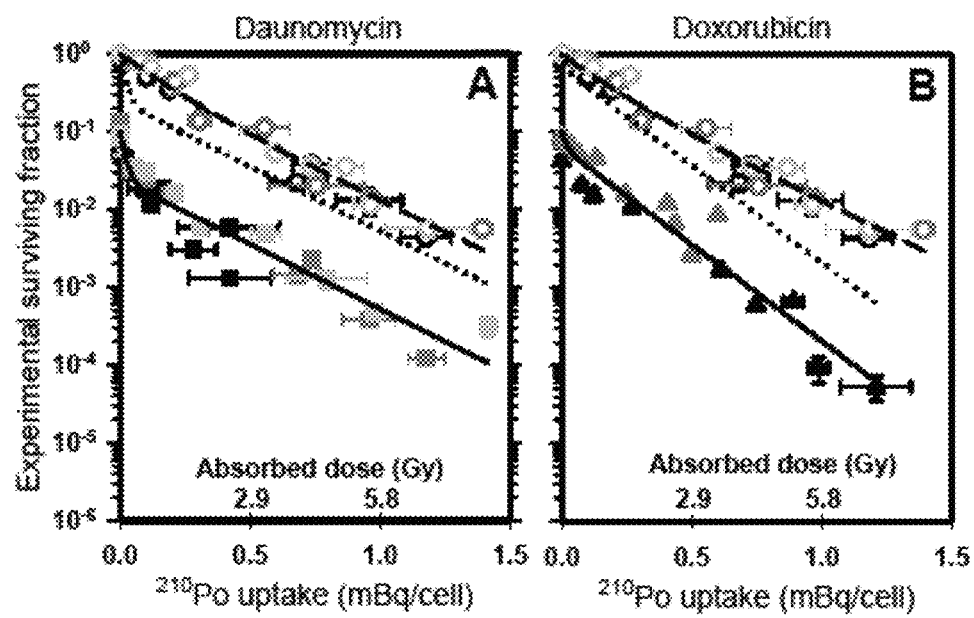
FIG. 9 displays the surviving fraction of V79 cells after treatment with graded amounts of $^{210}$Po-citrate in the absence or presence of: (A) 0.63 μM daunomycin or (B) 2.50 μM doxo-rubicin. Three independent experiments (○ $^{210}$Po-citrate; ■ $^{210}$Po-citrate+daunomycin; ▲ $^{210}$Po-citrate+doxorubicin). Dashed lines represent least-squares fits of data for $^{210}$Po-citrate to a 1-component exponential function. Solid curves represent least-squares fits of data for the combined treatment to 2-component exponential functions. Correction of the combined treatment curves for drug toxicity yielded the dotted curves. Horizontal and vertical error bars represent SE of mean cellular activity and surviving fraction of triplicate measurements, respectively. Some error bars are smaller than the symbols.
Figure 22:
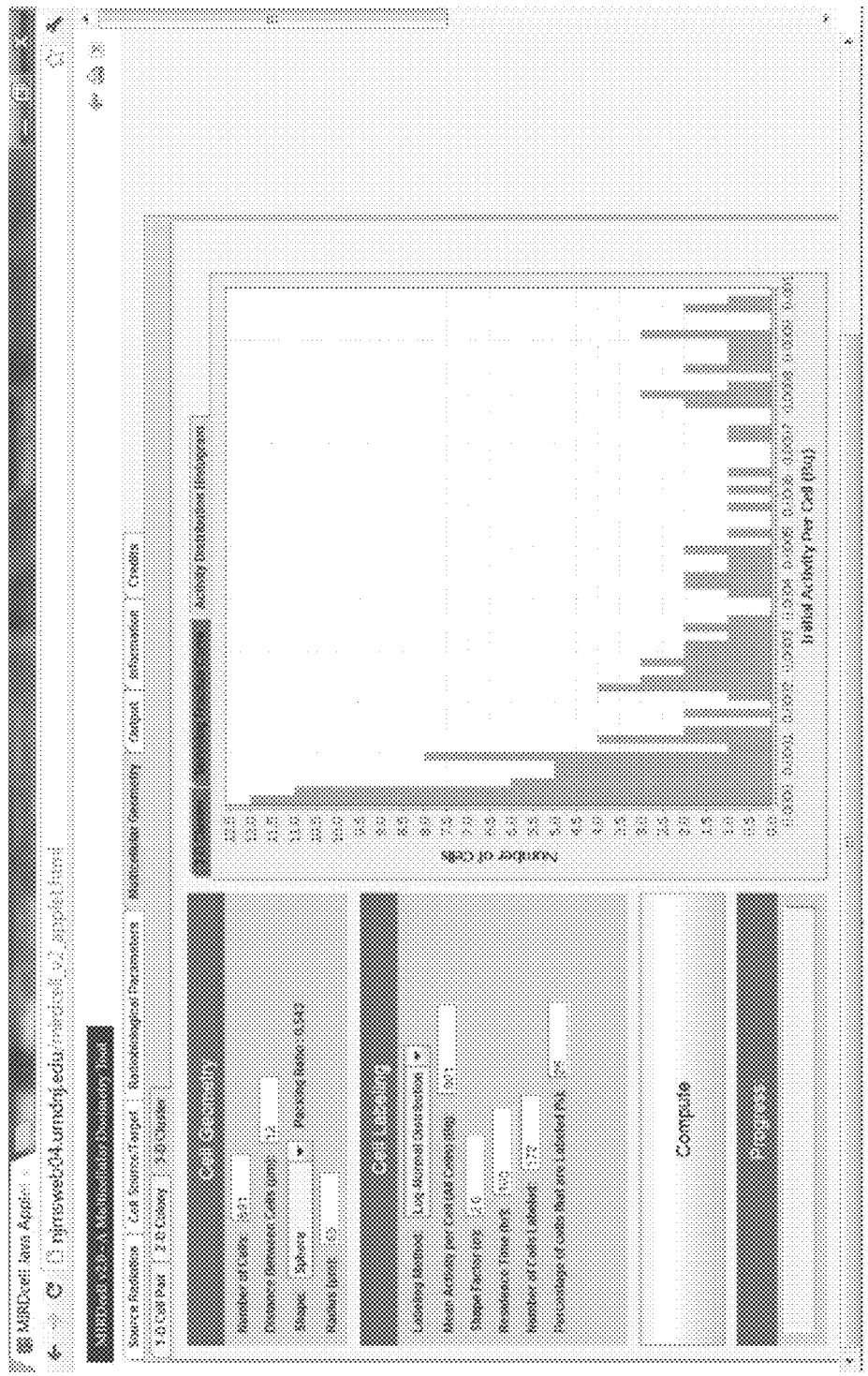
FIG. 22 illustrates an example GUI of a of Multicellular Geometry<3-D Cluster<Activity Distribution Histogram. Selecting the Activity Distribution Histogram sub-feature provides the distribution of activity among the labeled cell population under consideration based on entries in the tabs. This example shows a lognormal distribution. The small number of labeled cells (in this case it is 172) magnifies the stochastic aspects of the distribution in such a small population. Repeated selection of the Compute feature shows variations in the distribution when the Monte Carlo calculations are repeated.

FIG. 22 illustrates a GUI for a Multicellular Geometry<3-D Cluster<Activity Distribution Histogram category. As in the 2-D colony case, the user-specified activity distribution is plotted in this sub-feature. Examples of uniform, normal and lognormal distributions are shown in FIG. 9B.

Figure 23:
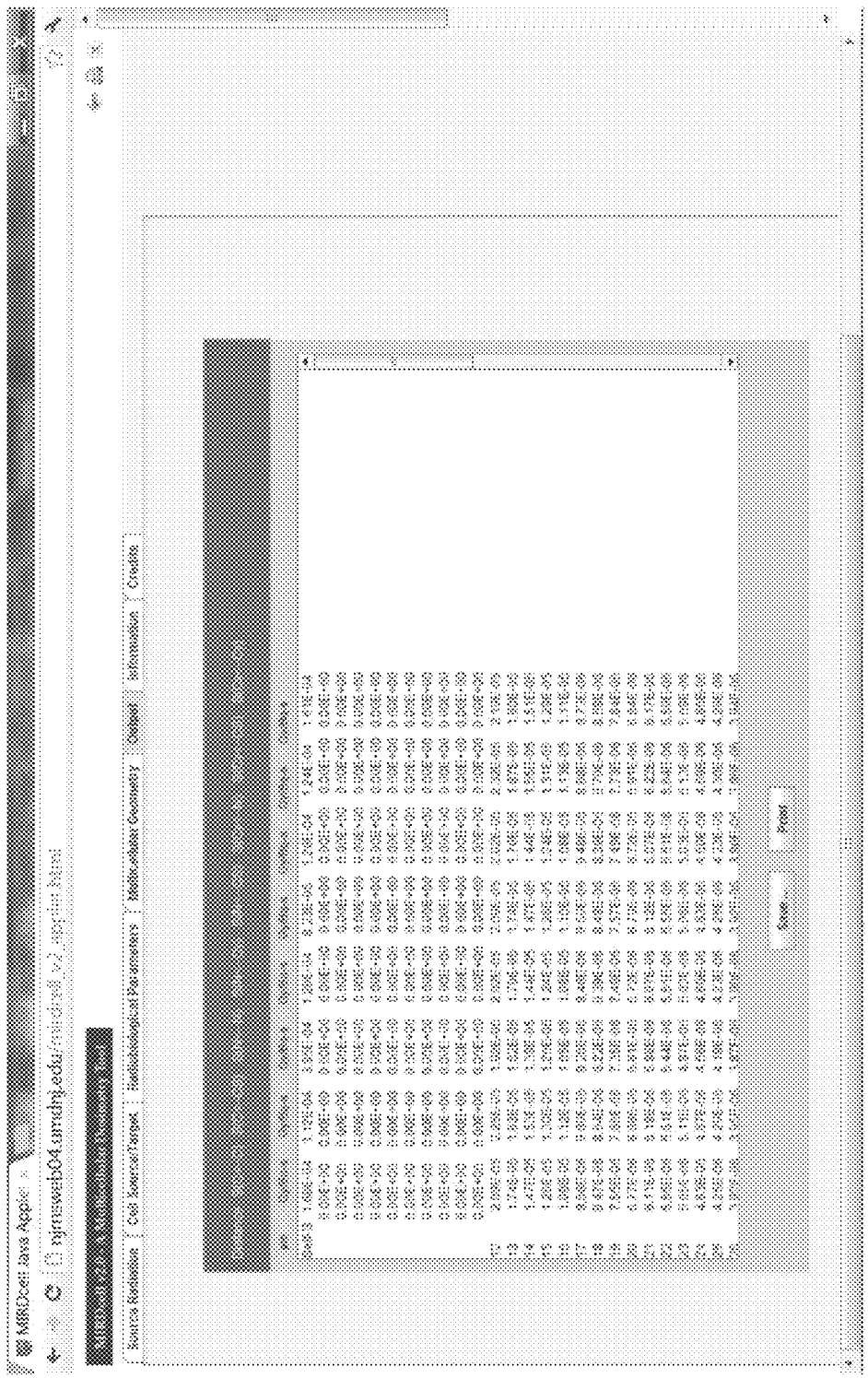
FIG. 23 illustrates an example GUI of an Output feature. This is a tabulation of the mean absorbed dose per unit cumulated activity (S value) for the various target and source volumes in cells of the dimensions selected in the Cell Source/Target feature. In this example, the cell radius is 6 μm which is half of the minimum cell separation distance of 12 μm (row 12). The top row provides the S values for a labeled cell. The cross-dose S values are provided by row 12 and higher. The distance represents the distance between the two cells for which the cross-dose S value is being calculated.

FIG. 23 illustrates a GUI for an Output feature 205. Upon completion of a calculation, a tabulation of the self- and cross-dose S values may be written to the text box within the Output feature. Other embodiments could provide the self- and cross-doses for each cell and their mean values, along with the surviving fraction. These results could be provided as tables and/or graphs including dose volume histograms and other formats suitable for the clinical environment.

Figure 24:
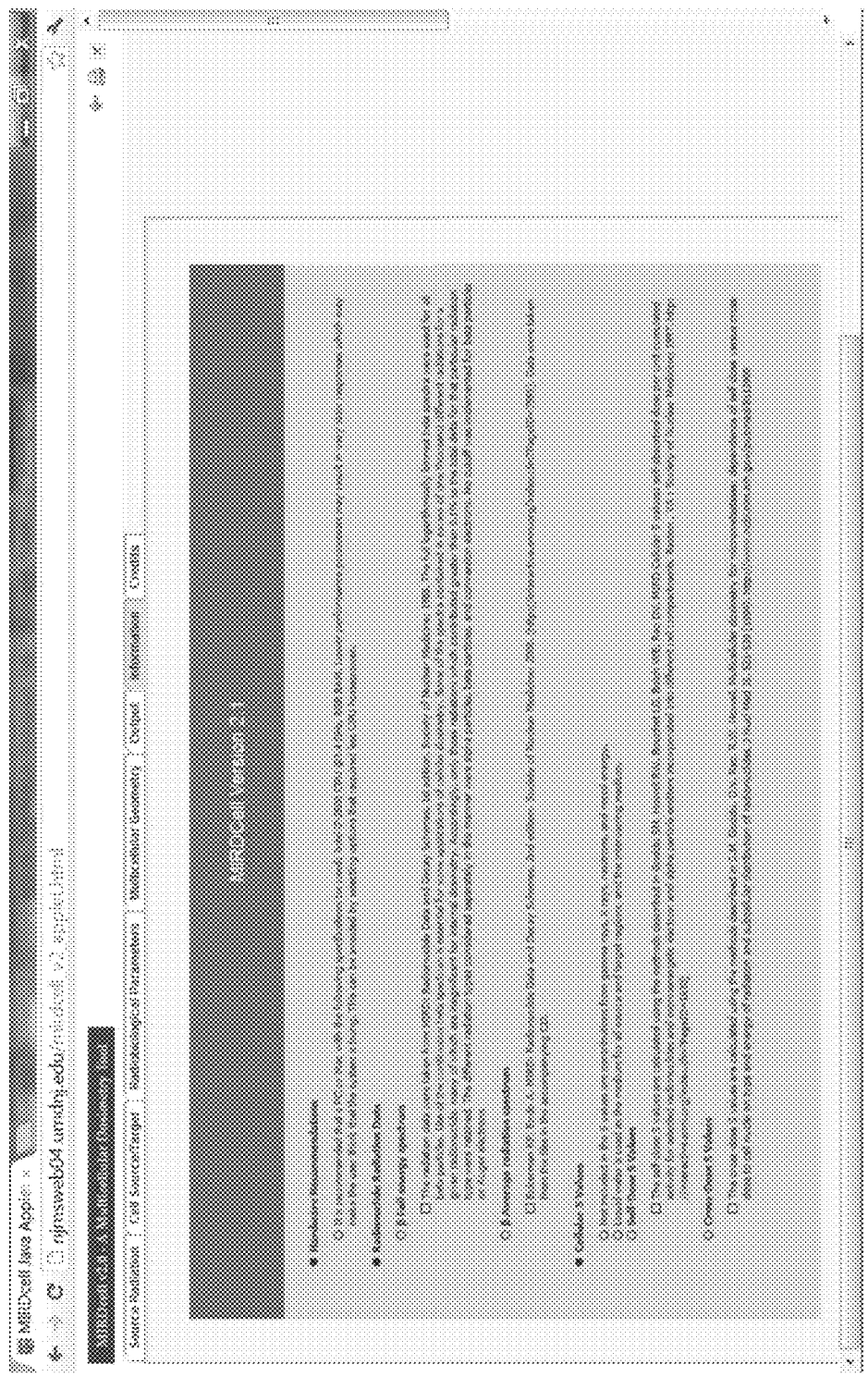
FIG. 24 illustrates an example GUI of an Information feature.

FIG. 24 illustrates a GUI for an Information feature 206. This information feature presents an abbreviated version of key information described above.

In the therapeutic setting there are often many clusters of cells that need to be sterilized. These clusters vary in shape and size. Another embodiment allows a user to specify the number of clusters and their sizes. The surviving fraction is calculated for each cluster and the probability of sterilizing all of the clusters is determined.

Figure 25:
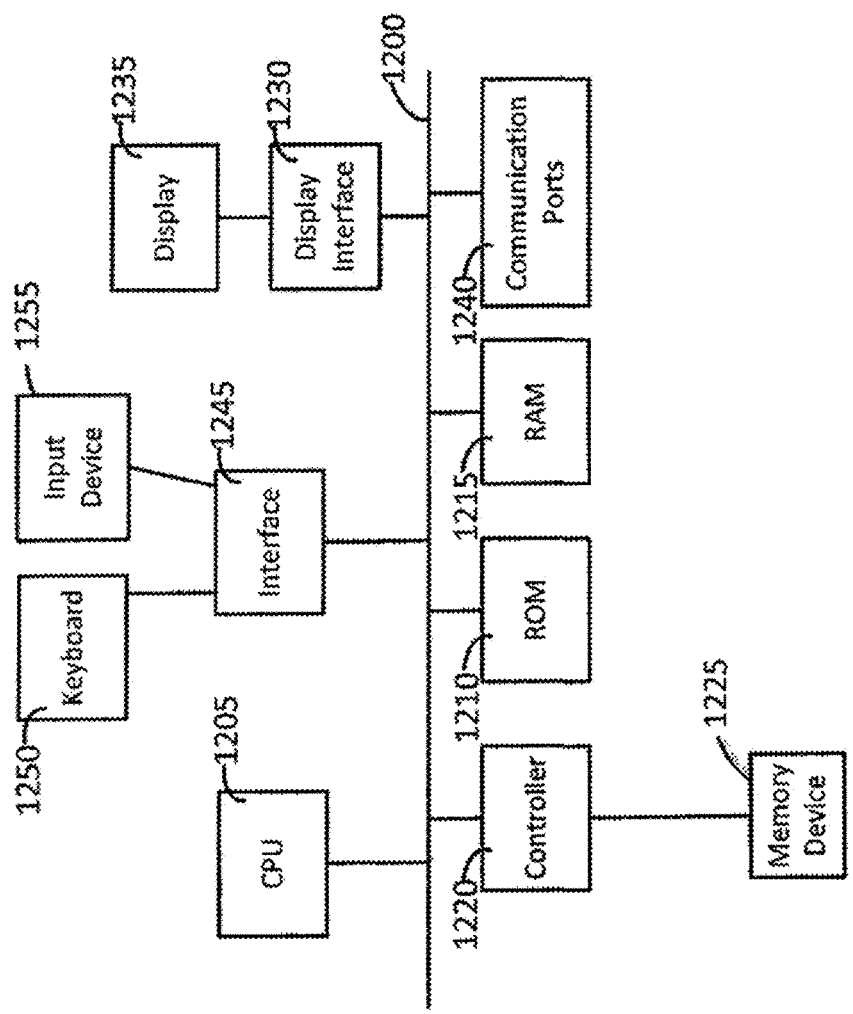
FIG. 25 illustrates a block diagram of example hardware that may be used to contain or implement program instructions according to an embodiment.

FIG. 25 depicts a block diagram of hardware that may be used to contain or implement an application according to the present invention. A bus 1200 serves as the main information highway interconnecting the other illustrated components of the hardware. CPU 1205 is the central processing unit of the system, performing calculations and logic operations required to execute an application and/or program instructions. CPU 1205, alone or in conjunction with one or more of the other elements disclosed in FIG. 22, is an example of a processing device, computing device or processor as such terms are used within this disclosure. Read only memory (ROM) 1210 and random access memory (RAM) 1215 constitute examples of memory devices.

A controller 1220 interfaces with one or more optional memory devices 1225 to the system bus 1200. These memory devices 1225 may include, for example, an external or internal DVD drive, a CD ROM drive, a hard drive, flash memory, a USB drive or the like. As indicated previously, these various drives and controllers are optional devices.

Program instructions, software or interactive modules for providing the interface and performing any querying or analysis associated with one or more data sets may be stored in the ROM 1210 and/or the RAM 1215. Optionally, the program instructions may be stored on a tangible computer readable medium such as a compact disk, a digital disk, flash memory, a memory card, a USB drive, an optical disc storage medium, such as a Blu-ray™ disc, and/or other recording medium.

An optional display interface 1230 may permit information from the bus 1200 to be displayed on the display 1235 in audio, visual, graphic or alphanumeric format. Communication with external devices, such as a printing device, may occur using various communication ports 1240. A communication port 1240 may be attached to a communications network, such as the Internet or an intranet.

The hardware may also include an interface 1245 which allows for receipt of data from input devices such as a keyboard 1250 or other input device 1255 such as a mouse, a joystick, a touch screen, a remote control, a pointing device, a video input device and/or an audio input device.

Figure 26:
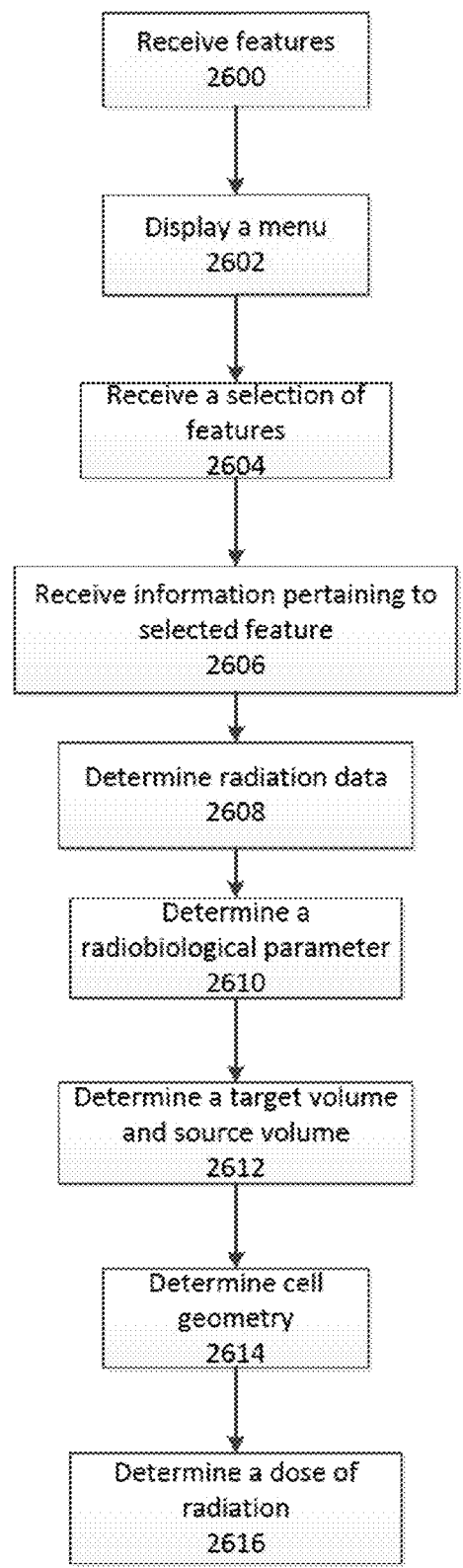
FIG. 26 illustrates a flow chart of an example method of determining a dose of radiation for a patient according to an embodiment. As illustrated by FIG. 26, the method may include receiving by a computing device 2600 one or more features associated with a dose of radiation. In an embodiment, the computing device may display 2602 a menu of one or more of the features associated with the dose of radiation. One or more of the features may correspond to a category of information.

FIG. 26 illustrates a flow chart of an example method of determining a dose of radiation for a patient according to an embodiment. This example is not limited to only determining a dose of radiation, and may include other types of agents to treat infections as well as cancer, such agents include biologic and chemotherapeutic agents. As illustrated by FIG. 26, the method may include receiving by a computing device 2600 one or more features associated with a dose of radiation. In an embodiment, the computing device may display 2602 a menu of one or more of the features associated with the dose of radiation. One or more of the features may correspond to a category of information as previously disclosed above.

In an embodiment, the computing device may receive 2604 a selection of one or more features from the menu of features. For example, the computing device may receive 2604 a selection of one or more features from a user. For one or more selected features, the computing device may receive 2606 information pertaining to the selected feature, determine 2608 radiation data for a radionuclide, determine 2610 a radiobiological parameter, determine 2612 a target volume and source volume, determine 2614 a cell geometry, and determine 2616 a dose of radiation based upon the selected feature. In a further embodiment, a recited feature may include data from a laboratory or patient sample as previously disclosed above.

As used in this document, the singular forms "a," "an," and "the" include plural references unless the context clearly dictates otherwise. Unless defined otherwise, all technical and scientific terms used herein have the same meanings as commonly understood by one of ordinary skill in the art. All publications mentioned in this document are incorporated by reference. All sizes recited in this document are by way of example only, and the invention is not limited to structures having the specific sizes or dimensions recited below. Nothing in this document is to be construed as an admission that the embodiments described in this document are not entitled to antedate such disclosure by virtue of prior invention. As used herein, the term "comprising" means "including, but not limited to."

TABLE 1

Organization of an Application and a Graphical User Interface

○ Source Radiation (FIG. 13)
  ■ Predefined MIRD Radionuclide
    ● β Full Energy Spectrum
    ● β Average Energy Spectrum
  ■ Monoenergetic Particle Emitter
  ■ User Created Radionuclide
    ● Add Radiation
    ● Confirm List of Radiations
  ■ Input Data for Calculation
○ Cell Source/Target (FIG. 14)
○ Radiobiological Parameters (FIG. 15)
○ Multicellular Geometry
  ■ 1-D Cell Pair (FIG. 16)
    ● Distance between cells
  ■ 2-D Colony
    ● 2-D Colony (FIG. 17A)
      ○ Cell Geometry
        ■ Number of cells
        ■ Distance between cells
        ■ Shape (Dimensions) (FIG. 17B)
          ● Circle (specify radius)
          ● Rectangle (specify length and width)
          ● Ellipse (specify short and long axis)
      ○ Cell Labeling
        ■ Labeling method
          ● Uniform
          ● Lognormal (specify sigma)
          ● Normal (specify sigma)
        ■ Mean activity per cell (all cells)
        ■ Time-integrated activity coefficient (ã)
        ■ Number of cells labeled
        ■ Percentage of cells that are labeled
    ● Surviving Fraction (FIG. 18)
      ○ SF labeled cells versus mean dose to labeled cells
      ○ SF unlabeled cells versus mean dose to unlabeled cells
      ○ SF all cells versus mean dose to all cells
    ● Activity Distribution (FIG. 19A, 19B)
  ■ 3-D Cluster
    ● 3-D Cluster (FIG. 20A)
      ○ Cell Geometry
        ■ Number of cells
        ■ Distance between cells
        ■ Shape (Dimensions) (FIG. 20B)
          ● Sphere (specify radius)
          ● Rod (specify length and width)
          ● Ellipsoid (specify short and long axis)
      ○ Cell Labeling
        ■ Labeling method
          ● Uniform TABLE 1-continued Organization of an Application and a Graphical User Interface ● Lognormal (specify sigma)
          ● Normal (specify sigma)
        ■ Mean activity per cell (all cells)
        ■ Time-integrated activity coefficient (ã)
        ■ Number of cells labeled
        ■ Percentage of cells that are labeled
    ● Surviving Fraction (FIG. 21)
      ○ SF labeled cells versus mean dose to labeled cells
      ○ SF unlabeled cells versus mean dose to unlabeled cells
      ○ SF all cells versus mean dose to all cells
    ● Activity Distribution (FIG. 2)
○ Output (FIG. 23)
○ Information (FIG. 24)

EXAMPLES

Predicting Cell Survival Based on Flow Cytometry Gating

Three approaches to modeling the surviving fraction of cells were undertaken. In the first approach, flow-cytometry fluorescence histograms of agent uptake were prepared and the cells were gated relative to control autofluorescence using FlowJo® software (TreeStar). The fractions of agent-negative cells were defined as the proportions of fluorescence spectra that had intensities below the maximum intensities of control samples (i.e. the fraction of fluorescence spectra below maximum autofluorescence). For $^{210}$Po, 0.1 mM citrate which corresponded to a nontoxic cellular activity of 0.03 mBq/cell was used for autofluorescence. In this simple approach, the gated subpopulations of agent-negative cells were considered as survivors, whereas gated subpopulations of agent-positive cells were considered dead. The surviving fraction was taken as the number of agent-negative divided by the sum of agent-negative and agent-positive cells.

Figure 5:
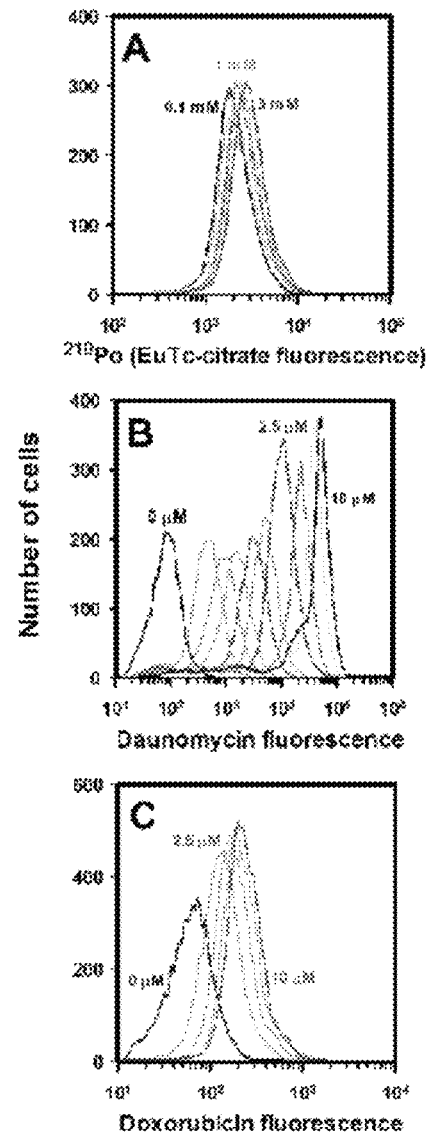
FIG. 5 shows a flow chart of the Monte Carlo procedure for determining fraction of surviving cells based on cellular fluorescence intensity profiles of the incorporated agent. In STEP 1, flow cytometry was used to obtain fluorescence intensity of EuTc-citrate ($^{210}$Po-citrate), daunomycin, and doxorubicin in individual V79 cells in a suspension culture. The distribution of measured cellular fluorescence intensities, adapted from FIG. 1, is shown in (A) 0.1-3 mM citrate, (B) 0-10 μM daunomycin, or (C) 0-10 μM doxorubicin. After calculating the probability of survival $P_i(I'_i)$ for the $i^{th}$ cell based on the normalized fluorescence intensity $I'_i$ (STEP 2), a random number $RAND_i (0<RAND_i \leq 1)$ was generated as depicted in STEP 3 by the dice. If $RAND_i<P_i(I'_i)$, then the cell was scored as a survivor, otherwise it was considered dead (STEP 4). A surviving cell is represented by a blossoming tree with leaves, while a dead cell is depicted by a tree without leaves. By repeating STEPS 1-4 for every cell in each population, the surviving fraction for any sample population was calculated as illustrated in STEP 5.

Predicting Cell Survival Based on Monte Carlo Analysis of Cellular Fluorescence Intensity The second approach, depicted in FIG. 5, employs a Monte Carlo simulation that uses experimental individual cell fluorescence intensities $I_i$ for the agent under consideration. The flow cytometry data for citrate, daunomycin, and doxorubicin, consisting of fluorescence intensities emitted by individual cells in a population after incorporation of a fluorescent agent $(I_1, I_2, I_3, \ldots, I_i)$, were exported into Microsoft Excel (Redmond, Wash.) spreadsheets. These raw values were normalized to $\langle I \rangle_{net}$ as per Equation (2).

$$I'_i = I_i\left(\frac{\langle I \rangle_{net}}{\langle I \rangle}\right), \quad (2)$$

where $$\langle I \rangle = \frac{1}{N}\sum_{i=1}^{N} I_i,$$

and N is the number of cells analyzed. The cytotoxicity of a therapeutic agent in a given cell is assumed to be exponentially related to the cellular uptake of the agent. Exponential functions are widely used to model the probability of cell death following cytotoxic insults from ionizing radiation and chemicals. Accordingly, the survival probability $P_i$ of the $i^{th}$ cell with normalized fluorescence intensity, $I'_i$, may be expressed as:

$$P_i(I'_i) = e^{\frac{I'_i}{\langle I \rangle_{net,37}}} \quad (3)$$

The resulting probability for each cell was compared with a random number generated from a uniform probability distribution by Excel, $0 < RAND_i \le 1$, and a binary value was assigned to the survival $s_i$ of the $i^{th}$ cell:

$$s_i = \begin{cases} 0 & \text{dead cell} \quad RAND_i > P_i(I'_i) \\ 1 & \text{live cell} \quad RAND_i \le P_i(I'_i) \end{cases} \quad (4)$$

A new random number was generated for each cell. This type of random number approach to determining the fate of each cell was also used in our recent communication (Rajon et al. 2011). Therefore, the surviving fraction of a population of N cells treated with a given concentration of an agent that yields net mean fluorescence intensity per cell, $\langle I \rangle_{net}$, may be expressed as:

$$SF(\langle I \rangle_{net}) = \frac{1}{N}\left(\sum_{i=1}^{N} s_i\right) \quad (5)$$

Care must be exercised when $$\sum_{i=1}^{N} s_i$$

is small because the statistical uncertainty of the Monte Carlo calculation of SF is high under such circumstances. This occurs at high agent concentrations that cause low surviving fractions. This is best circumvented by analyzing a larger number of cells. A less preferable alternative is to run additional simulations with new random number sequences and average the results.

Predicting Cell Survival Based on Mean Cellular Uptake

The third approach uses the same Monte Carlo approach for determining the fate of each cell, however, it is assumed that every cell in the population contains the same amount of drug. That is, each cell is assigned a fixed net mean fluorescence $\langle I \rangle_{net}$ which in essence corresponds to case wherein the lognormal shape parameter $\sigma \to 0$. In this instance, the probability of survival of the $i^{th}$ cell is given by $$P_i(\langle I \rangle_{net}) = e^{\frac{\langle I \rangle_{net}}{\langle I \rangle_{net,37}}} \quad (6)$$

The surviving fraction of the population is obtained using the same Monte Carlo method described above except that Equation (6) was used instead of Equation (3) to calculate the probability of survival.

Materials and Methods

Cell Line and Monolayer Culture

Chinese hamster V79 lung fibroblasts were used. Two different formulations of minimum essential media (MEMA and MEMB) were used, as known in the literature. All media and supplements were Gibco (Carlsbad, Calif.), including fetal calf serum (catalog no. 10437, lot no. 539574). For routine maintenance, cells were grown as monolayers in Falcon 25-cm$^2$ tissue culture flasks (BD, Franklin Lakes, N.J., catalog no. 353082) at 37° C., 5% $CO_2$-95% air, and subcultured twice weekly. For experiments, V79 cells (passage 4-11) were transferred into Falcon 225-cm$^2$ flasks (BD, catalog no. 353138), and were used upon reaching 80%-90% confluence.

Suspension Cell Culture

Cells grown in 225-cm$^2$ flasks were trypsinized (0.25% trypsin, Gibco, catalog no. 25200-056), and MEMB was added to obtain $2 \times 10^6$ cells/mL. Aliquots of 1 mL were placed in Falcon 17×100 mm polypropylene tubes (BD, catalog no. 352018) and placed on a rocker-roller (Thermo Fisher, Fair Lawn, N.J.) for 3 hours at 37° C. with 5% $CO_2$ and 95% air. After this conditioning period, cells were treated with drug or radiochemical. Cell cultures were exposed to radiochemical and drugs for 0.5 and 2.5 h, respectively.

Cellular Incorporation of $^{210}$Po-Citrate, Daunomycin, and Doxorubicin $^{210}$Po-Citrate. The uptake of $^{210}$Po-citrate was determined on a cell-by-cell basis by flow cytometric techniques, using $^{210}$Po-free citrate. Briefly, V79 cells ($2 \times 10^6$ cells/mL) were treated with 0-3 mmol/L of citrate and incubated on a rocker-roller as described earlier. Cellular uptake of citrate was tracked using an europium tetracycline (EuTc) conjugate. Samples were washed 2× with 10 mmol/L MOPS buffer (Sigma, St. Louis, catalog no. M3183), after a 30 min exposure to citrate. The cells were resuspended in 1 mL of MOPS buffer containing EuTc (Sigma, catalog nos. 203254 for Eu and T7660 for Tc), transferred into 7 ml polystyrene flow cytometry tubes (BD, catalog no. 352054), and were incubated at room temperature (~22° C.) in the dark for 30 min. The final concentration of EuTc was 100 μmol/L. EuTc forms a ternary complex with citrate (EuTc-citrate) which is excitable at 488 nm, and its emission can be captured within the wavelengths transmitted by the 610/20 filter. After washing 2× with MOPS buffer, the samples were resuspended in 1 mL of MOPS buffer, passed 5× through a 21-gauge needle, and were analyzed by flow cytometry using an LSR II flow cytometer (BD), equipped with a 488 nm laser. Cellular incorporation of citrate, expressed in terms of the fluorescence intensity per cell or mean fluorescence intensity (MFI) of EuTc-citrate, was used as a surrogate measure cellular uptake of $^{210}$Po-citrate.

Daunomycin and Doxorubicin.

To determine the cellular uptake of daunomycin and doxorubicin, the cells were treated with 0-10 μmol/L of each drug in MEMB and incubated on a rocker-roller for 2.5 h. The cells were washed 2× with phosphate buffered saline (PBS), resuspended in 1 mL of PBS, passed 5× through a needle, and were immediately subjected to flow cytometric analysis. The 488 nm laser was used to excite intracellular daunomycin and doxorubicin, and the emission spectra were captured within the wavelengths transmitted by the 575/26 and 530/30 filters, respectively. Cellular incorporation of drugs was also expressed as MFI.

Toxicity of $^{210}$Po-Citrate $^{210}$PoCl$_4$ in 2 mol/L HCl was obtained at 370 MBq/mL from Eckert&Ziegler Isotope Products (Valencia, Calif., catalog no. 6310). $^{210}$Po-citrate was prepared as follows. Briefly. PoCl$_4$ solution was mixed with 1 mol/L sodium citrate in the ratio of 1:7 (final pH 5.8), and was diluted with MEMB to a volume of 4 mL (final pH 6.9). One milliliter of MEMB containing $^{210}$Po-citrate was added to the 1 mL of conditioned V79 cultures (2×10$^6$ cells/mL), to arrive at a concentration of 0-250 kBq/mL (pH 6.9-7.0). After incubating for 30 min, the cells were washed 2× with MEMB, resuspended in 2 mL of MEMB, and incubated on a rocker-roller for 2.5 h to simulate concomitant drug exposure. The cells were resuspended in a 5 mL of MEMB, passed 5× through a needle, and counted with a Beckman Coulter Model Z2 (Brea, Calif.). Aliquots (500 µL) of the cell suspension were transferred to vials, mixed with 5 mL Ecolume (MP Biomedical, Solon, Ohio, catalog no. 882470), and counted with a Beckman Coulter LS6500, and the mean activity per cell was determined (efficiency, 50% as per prior studies). Aliquots of about 5×10$^5$ cells were counted in triplicate for $^{210}$Po activity and the cpm ranged from 10$^3$-10$^5$. The triplicate measurements kept statistical variations to a minimum. Each sample was serially diluted and plated in Falcon 60×15 mm tissue culture dishes for colony formation. Cultures were incubated for 7 days, and the colonies were fixed in 95% ethanol, stained with 0.01% Amido Black, washed in tap-water, air-dried, and counted.

Biologic Clearance of $^{210}$Po

To determine the biologic clearance of $^{210}$Po from the cells, 4×10$^6$ cells/mL were treated with $^{210}$Pocitrate as described above. After two washes with MEMB, the cells were resuspended in 5 mL of MEMB, passed 5× through a needle, and Coulter counted. Aliquots of 500 µL of cells were transferred to vials and mixed with Ecolume. The remaining cell suspension was plated into 25-cm$^2$ flasks (1.0, 0.5, 0.5, 0.2 and 0.2×10$^6$ cells/flask). The cultures were harvested after 24, 48, 72, and 96 h, respectively. Each sample was processed for cell counting and liquid scintillation counting as described. All vials were counted after the last harvest. The ratio of cellular activity at each time point to that immediately after treatment was calculated and plotted.

Toxicity of Daunomycin and Doxorubicin

After conditioning, the cell cultures were treated with daunomycin (Sigma, catalog no. D8809) or doxorubicin (Sigma, catalog no. 44583) to a final concentration of 0-10 µmol/L in MEMB. The tubes were returned to the rocker-roller for 2.5 h. The cells were then processed for colony formation as described above.

Analysis of the Flow Cytometry Data for Cocktails of Agents

Samples.

Flow cytometry control samples consisted of cells treated with the following agents: 1) untreated, 2) 3 mM citrate, 3) 0.63 µM daunomycin, and 4) 2.50 µM doxorubicin, Daunomycin+citrate test samples were 0.63 µM daunomycin+0.1, 0.2, 0.5, 1.0, 1.5, 2.0, 2.5, or 3.0 mM citrate. Doxorubicin+citrate test samples were 2.50 µM doxorubicin+0.1, 0.2, 0.5, 1.0, 1.5, 2.0, 2.5, or 3.0 mM citrate.

Acquisition.

Fluorescence intensity histograms were acquired for each sample using an LSR II flow cytometer (BD). The europium tetracycline-citrate complex, daunomycin, and doxorubicin were excited with a 488 nm laser, and their emission spectra were captured within the wavelengths transmitted by the 610/20, 575/26 and 530/30 filters, respectively.

Analysis.

FlowJo software (TreeStar) was used to analyze each sample. Dot plots of forward scatter versus side scatter were created to gate cells from debris. Fluorescence intensities were compensated for overlapping emission spectra.

Results

Predicting Cell Survival Based on Flow Cytometry Gating

Cells with fluorescence intensities greater than the maximum autofluorescence were considered as agent-positive, while those with lower intensities were agent-negative. For $^{210}$Po-citrate and doxorubicin, most cells emerged as agent-negative regardless of agent concentration. This occurred because of the relatively small increase in <I> with increasing extracellular concentration of the agent. The proportion of daunomycin-positive cells consistently increased with increasing drug concentration. Conversely, the proportion of daunomycin-negative cells decreased substantially with increasing drug concentration. When surviving fraction, defined in this instance as fraction of agent-negative cells, was plotted as a function of agent concentration, it was apparent that agent-negativity, based on what might be considered conventional flow-cytometry gating, is not necessarily indicative of the ability of a cell to survive. For $^{210}$Po and doxorubicin, the fraction of agent-negative cells was found to significantly overestimate cell survival over the entire range of agent concentrations assessed. While there was relatively good agreement between daunomycin-negativity and clonogenic cell survival at low concentrations, the fraction of cells that were apparently drug negative failed to accurately predict survival at higher drug concentrations.

Predicting Cell Survival Based on Monte Carlo Analysis of Cellular Fluorescence Intensity To assess the capacity of Monte Carlo simulation of cell death and survival from cellular fluorescence data acquired by flow cytometry, the procedure depicted in FIG. 5 was employed. Only the net mean lethal fluorescence intensity, <I>$_{net,37}$ and the measured fluorescence intensity in each cell of the treated population were needed to theoretically model the surviving fraction following treatment by each drug. Panels A, B and C of FIG. 5 show the lognormal nature of the distribution of measured fluorescence intensities following treatment with graded concentrations each drug. Application of Equation (3) to the two cell populations provides the survival probabilities P$_i$(I'$_i$) of each cell in populations treated with 0 or 5 µM daunomycin. By generating a random number RAND$_i$ between 0 and 1 (FIG. 5, STEP 3), and comparing it with the survival probability P$_i$(I'$_i$), the fate (s$_i$) of each cell was determined according to Equation (4) (FIG. 5, STEP 4). The surviving fraction of cells, SF(<I>$_{net}$), based on normalized individual fluorescence intensities I'$_i$, were then calculated using Equation (5) (FIG. 5, STEP 5). There is a transition from nearly all live cells to nearly all dead cells as the agent concentration is increased.

The process described above for determining the surviving fraction SF(<I>$_{net}$) was carried out for each of the cell populations which were treated with 0.1-3 mM citrate. The resulting theoretically modeled surviving fractions SF(<I>$_{net}$) are plotted in FIG. 6A for $^{210}$P-citrate, along with the experimental clonogenic survival data. This process was repeated for daunomycin and doxorubicin to create the theoretical data points in FIGS. 6B and 6C, respectively. The Monte Carlo simulated cell survival is in good agreement with colony forming ability of V79 cells after treatment with the cytotoxic agents.

Predicting Cell Survival Based on Mean Cellular Uptake

Survival curves based on Monte Carlo analysis wherein each cell in the population contains the same amount of drug are presented as straight, dashed lines in FIG. 6. These provide an important point of comparison with the flow cytometry gating model and the Monte Carlo model that accounts for the lognormal distribution of cellular uptake of the agent.

Prediction of Multiple Agent Toxicity

The approach for modeling cell survival using a Monte Carlo simulation is based on individual cell fluorescence intensities $I_i$ for a single agent as described above. When cells were concomitantly treated with multiple agents, the fluorescence intensities of all agents within each cell of each treated population were measured simultaneously using flow cytometry. These data were used to perform a Monte Carlo analysis to simulate the surviving fraction of cells after treatment with all possible combinations of the agents. This process is depicted for a cocktail of agents in FIG. 8.

Flow cytometry of a population of N cells treated with a cocktail of agents provided the fluorescence intensity of each agent in each cell. These data were exported into Microsoft Excel (Redmond, Wash.) spreadsheets. The raw fluorescence intensities for the $j^{th}$ agent in the $i^{th}$ cell, $I_{ij}$, were normalized to $\langle I_j \rangle_{net}$ for each agent as per Equation (2A)

$$I'_{ij} = I_{ij} \left( \frac{\langle I_j \rangle_{net}}{\langle I_j \rangle} \right), \quad (2A)$$

where $$\langle I_j \rangle = \frac{1}{N} \sum_{i=1}^{N} I_{ij}, \text{ and } \langle I_j \rangle_{net}$$

denotes the net mean fluorescence intensity per cell following exposure to the $j^{th}$ agent. $\langle I_j \rangle_{net}$ is determined by subtracting the mean control autofluorescence, $\langle I_j \rangle_{control}$, from the mean fluorescence intensity per cell in a treated population as defined by Equation (1A):

$$\langle I_j \rangle_{net} = \langle I_j \rangle - \langle I_j \rangle_{control} \quad (1A)$$

For $^{210}$Po-citrate, a citrate concentration of 0.1 mM, which was found to correspond to a nonlethal cellular activity of 0.03 mBq/cell, was used for control autofluorescence. The net mean cellular fluorescence intensity of Agent j that yields 37% survival is denoted $\langle I_j \rangle_{net,37}$ [20]. To account for natural variations in $\langle I_j \rangle_{net,37}$ from experiment to experiment, it is necessary to obtain an $\langle I'_j \rangle_{37}$ for each experiment from a calibration of an experimentally determined surviving fraction. Assuming that the toxicity of the $j^{th}$ agent in a given cell population is exponentially related to the cellular uptake of the agent, the surviving fraction of such a population based on its net mean fluorescence intensity, $\langle I'_j \rangle$, is:

$$SF_j = e^{\langle I'_j \rangle / \langle I'_j \rangle_{37}}$$

For instance, using the net mean fluorescence intensity of a cell population corresponding to 10% cell survival, $$\langle I'_j \rangle_{37} = -\frac{\langle I'_j \rangle}{\ln(0.1)}.$$

At the single-cell level, the survival probability of the $i^{th}$ cell with normalized fluorescence intensity, $I'_{ij}$, may be expressed as (FIG. 8, STEP 2):

$$P_i(I'_{ij}) = e^{-I'_{ij} / \langle I'_j \rangle_{37}} \quad (6A)$$

Therefore, the survival probabilities for the $i^{th}$ cell when treated with Agent 1 or Agent 2 are given by $P_i(I'_{i1}) = e^{-I'_{i1}/\langle I'_1 \rangle_{37}}$ and $P_i(I'_{i2}) = e^{-I'_{i2}/\langle I'_2 \rangle_{37}}$, respectively.

To model cell survival following treatment with a cocktail of two agents, we hypothesize that a cell may die due to Agents 1 and 2 working independently or interactively. The survival probability $P_i(I'_{i1}, I'_{i2})$ of the $i^{th}$ cell is represented by:

$$P_i(I'_{i1}, I'_{i2}) = \Omega(I'_{i1}, I'_{i2}) P_i(I'_{i1}, I'_{i2}) P_i(I'_{i1}) P_i(I'_{i2}) \quad (8)$$

$$\Omega(I'_{i1}, I'_{i2}) = \begin{cases} 1 & \text{agents work independently} \\ P_i(I'_{i1}) P_i(I'_{i2}) & \text{agents work interactively} \end{cases} \quad (8A)$$

where $\Omega_i(I'_{i1}, I'_{i2})$ is a term that accounts for the interaction of the two agents.

The probability calculated with Equations (8) and (8A) was then compared with a random number, $0 < RAND_i \le 1$ (FIG. 8, STEP 3), and a binary value was assigned to the survival $s_i$ of the $i^{th}$ cell:

$$s_i = \begin{cases} 0 & \text{dead cell} \quad RAND_i > P_i(I'_{i1}, I'_{i2}) \\ 1 & \text{live cell} \quad RAND_i \le P_i(I'_{i1}, I'_{i2}) \end{cases} \quad (4A)$$

A new random number was generated for each cell. This approach to determining the fate of each cell (FIG. 8, STEP 4) was also used in our recent communications. Therefore, the surviving fraction of a population of N cells treated with Agent 1+Agent 2 is given by (FIG. 8, STEP 5):

$$SF_i(I'_{i1}, I'_{i2}) = \frac{1}{N} \left( \sum_{i=1}^{N} s_i \right) \quad (5A)$$

One embodiment of the invention employs a Monte Carlo approach to simulate the fate of each cell based on its experimentally determined drug uptake and used this information to calculate a surviving fraction for the entire cell population. The resulting surviving fractions were compared to experimentally determined values. Two different methods of predicting cell survival following a toxic insult were considered. The first approach addressed the role of individual agent uptake (i.e. cell fluorescence) in cell survival. The fate of individual cells can be determined based on their incorporation of a given agent, in this case daunomycin. However, it is worth noting that the magnitude of a cell's survival probability, per se, is not conclusive as to whether a cell survives or dies. Hence, there is a need to simulate the fate of each cell within the population using Monte Carlo techniques.

In FIG. 6, experimentally determined cell survival data are compared with theoretical cell survival data that were simulated by Monte Carlo analysis. However, before applying the Monte Carlo approach to account for the experimental lognormal uptake distributions, it is instructive to first see how this model behaves when each cell is assumed to contain the same uptake (i.e. the mean uptake). As expected, when theoretical survival is simulated assuming that each cell in the population contains an agent quantity corresponding to the net mean cellular fluorescence intensity, the resulting survival curve is monoexponential (FIG. 6, dashed lines). In this approach, the fact that each cell in the population is assumed to incorporate the same amount of agent implies $\sigma \to 0$. The data clearly show that, regardless of the agent, the theoretical survival derived from mean cellular fluorescence can recapitulate clonogenic survival only within the first exponential component of cell kill.

Figures 6A, 6B, 6C:
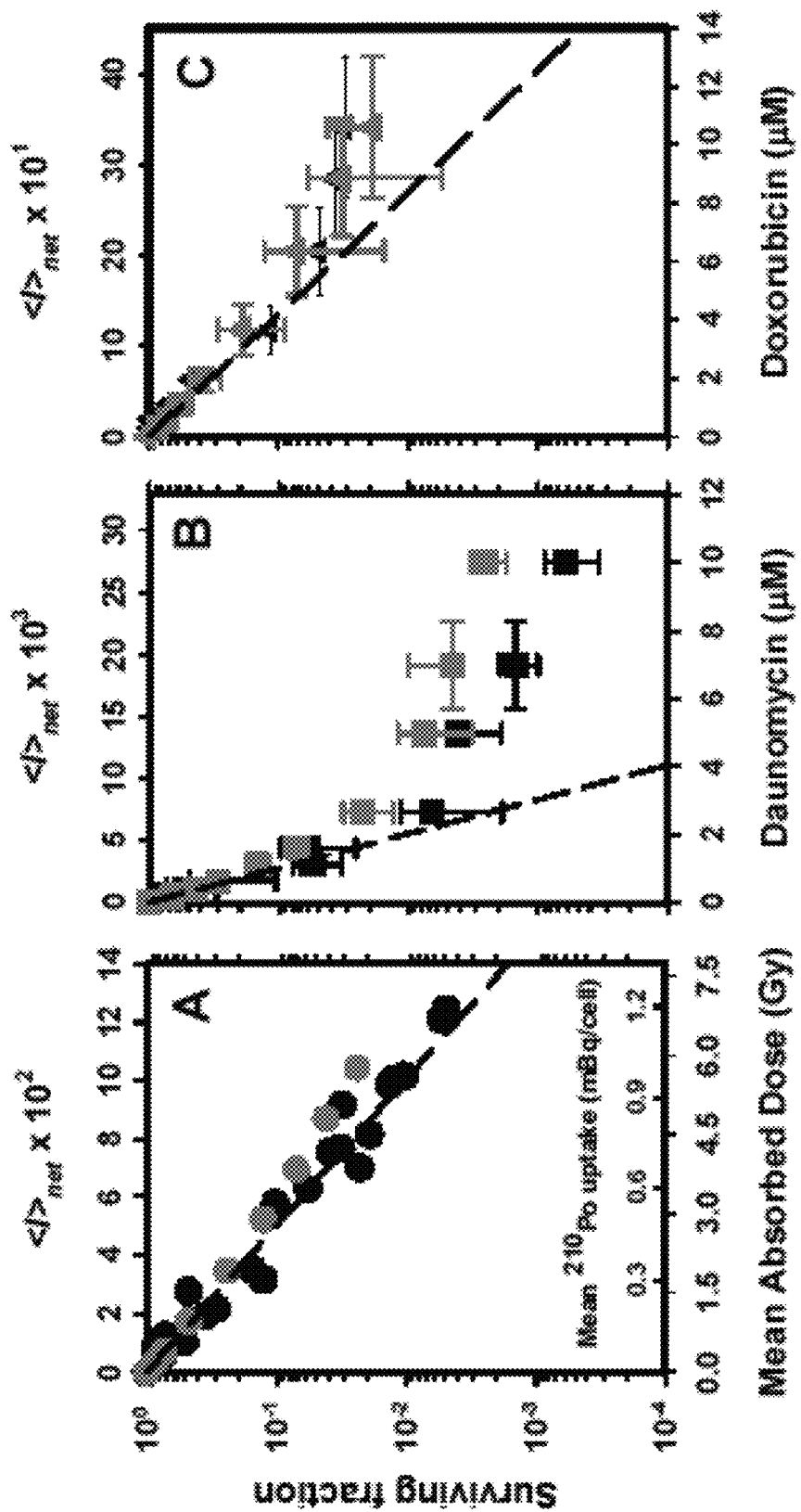
FIG. 6 shows comparison of Monte Carlo simulated cell survival (light symbols) with experimental clonogenic cell survival (black symbols) of V79 cells after treatment with (A) $^{210}$Po-citrate, (B) daunomycin, or (C) doxorubicin. The surviving fraction for $^{210}$Po-citrate are plotted against mean absorbed dose to the cell nucleus, mean intracellular $^{210}$Po activity, and mean fluorescence intensity of the europium tetracycline-citrate complex. Dashed lines represent Monte Carlo simulations of cell survival when every cell in the population is assumed to contain the same amount of drug that corresponds to the mean drug uptake for the respective extracellular concentration (i.e. net mean fluorescence intensity). Error bars represent the SE for $\langle I \rangle_{net}$ based on fluorescence data from two and three independent experiments for daunomycin and doxorubicin, respectively. Error bars for $^{210}$Po citrate data are smaller than the symbols.
Figures 7A, 7B:
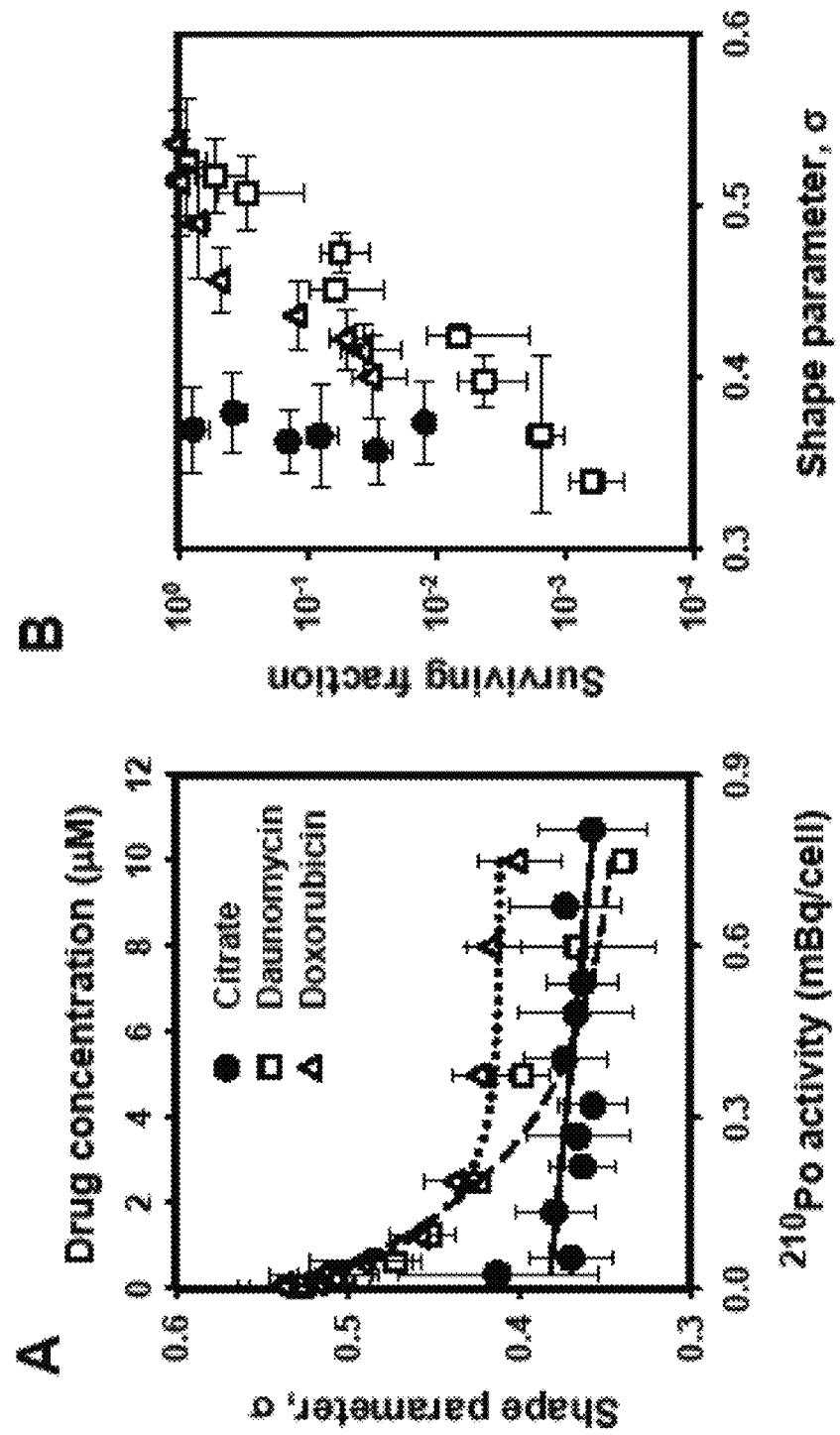
FIG. 7A displays the lognormal shape parameters σ for $^{210}$Po-citrate, daunomycin, and doxorubicin plotted against intracellular $^{210}$Po activity (●, solid line), and extracellular concentration of daunomycin (□, dashed line) and doxorubicin (Δ, dotted line), respectively. B displays the surviving fraction versus shape parameter for $^{210}$Po-citrate (●), daunomycin (□), and doxorubicin (Δ). Error bars represent SE of three independent experiments.

In contrast to the poor match between experimental data and the mean approach, Monte Carlo simulation of cell survival in a manner that accounts for the lognormal uptake distribution provides a very good prediction of clonogenic survival following treatment with $^{210}$Po-citrate, daunomycin, and doxorubicin (FIG. 6). Moreover, this model accurately predicts the transition between the first and second components of cell killing. This transition coincides with that observed when the lognormal shape parameter is plotted as a function of drug concentration. It should be noted that in the case of daunomycin, the Monte Carlo approach accurately predicts cell survival at low drug concentrations within the first log of cell kill but there is some deviation from experimental values at high drug concentrations (FIG. 6B). Nevertheless, the fit is remarkably good compared with the more conventional approach based on mean drug uptake (FIG. 6, dashed lines). Approaches based on mean uptake adequately predict the response in the low-dose realm, but fail to predict the upward trend in the survival curve that arises as a consequence of the lognormal distribution of drug uptake.

Toxicity of Cocktails

To evaluate cytotoxicity of combined treatment of V79 cells with $^{210}$Po-citrate and daunomycin, or $^{210}$Po-citrate and doxorubicin, the surviving fraction of clonogens was plotted as a function of mean cellular uptake of $^{210}$Po (FIG. 9) and as a function of mean absorbed dose to the cell nucleus. When cells were only treated with $^{210}$Po-citrate, the survival curve can be described by a 1-component exponential function. When cells were concomitantly treated with a single drug concentration and varying amounts of $^{210}$Po-citrate, the dose-response curves followed a 2-component exponential function. The data corresponding to the combined treatments were then corrected for drug toxicity, by dividing the surviving fraction for each datum point by the surviving fraction for drug alone (SF=0.10), and replotted in FIG. 9. Both of the corrected cell survival curves emerged below those obtained for $^{210}$Po-citrate alone. This indicates that daunomycin and doxorubicin enhance the radiotoxicity of $\alpha$-particles in V79 cells. As illustrated in FIG. 9A, the enhancement of $\alpha$-particle radiotoxicity by daunomycin was independent of radiation absorbed dose beyond about 0.5 Gy (~0.09 mBq/cell). On the other hand, the increased kill provided by doxorubicin showed a dose-dependent increase (FIG. 9B).

Figure 8:
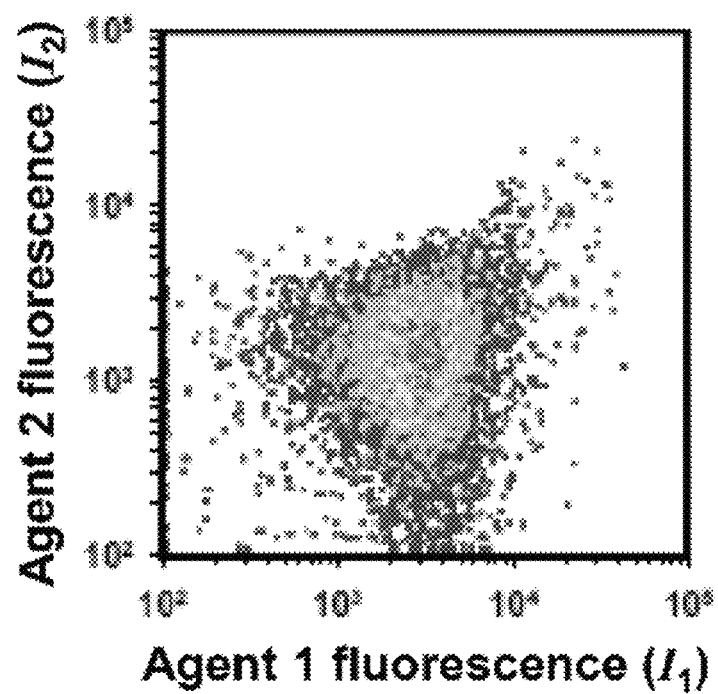
FIG. 8 shows a flow chart of the Monte Carlo procedure for determining fraction of surviving cells based on cellular fluorescence intensity distributions that arise after treatment of cells with a cocktail of two therapy agents (Agent 1 and Agent 2). In STEP 1, flow cytometry is used to obtain a fluorescence intensity dot-plot of the treated cells. STEP 2 calculates the probability $P(I'_{i1}, I'_{i2})$ that the $i^{th}$ cell survives treatment with Agents 1 and 2, based on the respective normalized fluorescence intensities $I'_{i1}$ and $I'_{i2}$. A random number $RAND_i (0<RAND_i \leq 1)$ is then generated as depicted in STEP 3 by the dice. If $RAND_i<P(I'_{i1},I'_{i2})$, then the cell is scored as a survivor, otherwise it is considered dead (STEP 4). By repeating STEPS 1-4 for every cell, the surviving fraction for any sample population is calculated as illustrated in STEP 5.
Figures 10A, 10B:
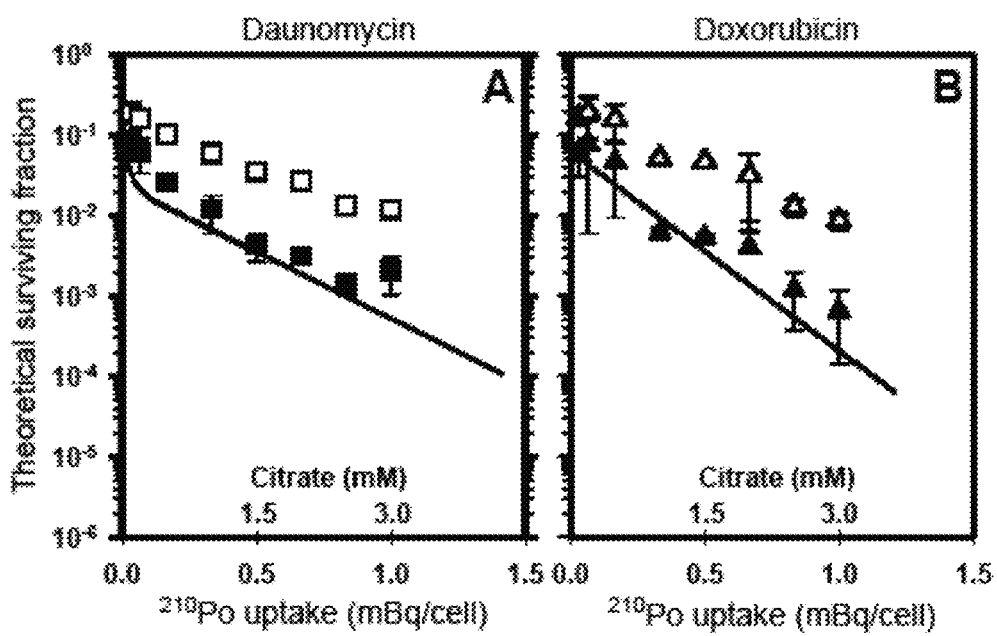
FIG. 10 displays the comparison of Monte Carlo simulated cell survival (symbols) with experimental clonogenic cell survival (solid curves) of V79 cells after treatment with combinations of (A) $^{210}$Po-citrate+0.63 μM daunomycin or (B) $^{210}$Po-citrate+2.50 μM doxorubicin. The experimental survival curves are least squares fits of the data presented in FIG. 9. Open and closed symbols represent Monte Carlo simulations of cell survival when the agents are assumed to act independently and interactively, respectively. Error bars represent the SE for simulated surviving fraction based on fluorescence data from two independent experiments for each cocktail. Some error bars are smaller than the symbols.

Predicting Cell Survival Based on Monte Carlo Analysis of Cellular Fluorescence Intensity The procedure depicted in FIG. 8 was used to assess the capacity of flow-cytometry assisted Monte Carlo simulation to recapitulate cell death and survival after exposure to $^{210}$Po-citrate+daunomycin or $^{210}$Po-citrate+doxorubicin. Following STEPS 2-4 of FIG. 8, application of Equations (6A), (8), (8A) and (4A) yields a plot of live and dead cells for fixed daunomycin concentration and varying concentrations of $^{210}$Po-citrate. The surviving fraction of a given cell population, based on normalized individual fluorescence intensities, $I'_{ij}$, was then calculated using Equation (5A) (FIG. 8, STEP 5). The symbols in FIG. 10 represent the theoretically modeled surviving fractions for $^{210}$P-citrate+daunomycin and $^{210}$P-citrate+doxorubicin. The theoretical data are superimposed on curves representing least squares fits to the experimental clonogenic survival data that were shown in FIG. 9. The open symbols were obtained assuming independent action of the agents (upper form of Equation (8A)), while closed symbols represent modeled cell survival when the agents are considered to interact (lower form of Equation (8A)). The Monte Carlo simulation that implemented agent-interaction is in excellent agreement with the experimental data.

These data provide experimental evidence that treatment of Chinese hamster V79 cells with a cocktail of $^{210}$Po-citrate and a chemotherapy drug (daunomycin or doxorubicin) causes cytotoxicity greater than expected based on the lethality of the agents when used alone (FIG. 9). These data show that when the effect of each chemotherapy drug is corrected for, the corrected survival curves do not coincide with that for the $^{210}$Po alone treatment. The curves emerge below the $^{210}$Po survival curve. This is indicative of a chemical enhancement of $\alpha$-particle radiotoxicity, or perhaps that cells that are not adequately labeled with $^{210}$Po-citrate (e.g. low end of the lognormal uptake distribution) are killed by the chemotherapy drug. The flow-cytometry assisted Monte Carlo simulation of cell survival can distinguish these possibilities.

In the cocktail embodiment, the flow cytometry-assisted Monte Carlo model has been applied to agent-incorporation data obtained after treating cells with a cocktail of $^{210}$Po-citrate+daunomycin or $^{210}$Po-citrate+doxorubicin. The test of the capacity of this approach to predict the cytotoxicity of a combination therapy is presented in FIG. 10 where experimentally determined cell survival curves (solid curves) are compared with theoretical cell survival as simulated by Monte Carlo analysis (symbols). When it is assumed that the agents act independently, the model fails to predict clonogenic cell survival (FIG. 10, open symbols). However, when the agents are assumed to interact, the Monte Carlo simulation predicts cell survival exquisitely at all intracellular activities of $^{210}$Po (FIG. 10, closed symbols). This suggests that, at the levels of cell kill observed, the chemotherapy agents provide a chemical enhancement of the $\alpha$-particle radiotoxicity in V79 cells rather than killing cells that are inadequately labeled with $^{210}$Po-citrate. The latter possibility may become important at very high levels of cell kill (i.e. 5 or 6 logs of kill).

The cocktail approach accurately predicts the experimental toxicity of the $^{210}$Po-citrate+daunomycin/doxorubicin cocktails based only on knowledge of the initial slope of the dose-response curves for each agent (i.e. $<I_j>_{37,net}$) and the cellular uptake distribution of the ingredients of the cocktail. This can be extremely helpful in designing more effective cocktails for targeted therapy; these cocktails may consist of a sizeable number of agents.

Although the use of $\alpha$-emitting radionuclides in radioimmunotherapy has gained considerable interest, the relatively high potency of $\alpha$-particles limits the amount of activity that can be administered. To benefit from the potency of $\alpha$-particles and yet maintain low normal tissue toxicity, the use of low doses of cocktails of $\alpha$-particle based radioimmunotherapeutics and chemotherapy drugs that effectively target all malignant cells is warranted. Yet, only one study has been reported to demonstrate enhancement of the anti-tumor effects of $\alpha$-particles in a mouse tumor model by paclitaxel. While the exact mechanism of that enhancement is not known, it was suggested to be dependent on the sequence of the administration of the therapeutic agents, and was both angiogenic and apoptotic by nature. Predicting response to radionuclide therapy and chemotherapy drugs on a cell-by-cell basis enables the dissecting of mechanisms involved with drug interaction, and thereby improves the design of more effective cocktails for targeted therapy. Therefore, it is possible that agents previously discarded on the basis of single-agent toxicity may become key ingredients in a cocktail by virtue of their capacity to target a few cells that only incorporate small amounts of the primary drug.

Of particular importance in the above-described embodiments is the fact that the flow-cytometry assisted Monte Carlo simulation of cell survival requires knowledge of only the initial slope of the dose-response curve (i.e. $<I>_{net,37}$) and the uptake distribution of the radiopharmaceutical or drug. With these two pieces of information, the entire clonogenic survival curve can be recapitulated including both the 1- or 2-component exponential shapes. The approach applies equally well for drugs that are not likely to be characterized by a lognormal uptake distribution such as Hoechst 33342, whose uptake is directly proportional to DNA content.

Special attention should be given to the process of normalizing the fluorescence data obtained by flow cytometry. The measured fluorescence intensities are dependent on flow cytometry hardware (e.g. laser wavelength and intensity), settings (e.g. amplification), etc. Given that the fluorescence intensity is ultimately related to drug uptake in terms of quantities such as mass (g) and/or activity (Bq), there will be a need to implement calibrations for these quantities. The mean activity per cell can be readily measured with high accuracy and precision using standard radiation detection devices. This information, along with the distribution of cellular fluorescence intensities, provides detailed knowledge of the activity in each cell of the population. Furthermore, calibration with drugs with known specific activity (Bq/g) can provide detailed knowledge of the mass of drug in each cell of the population. Accordingly, survival probabilities might be represented by $$P_i = e^{-\frac{m_i}{\langle m \rangle_{37}}} \text{ and } e^{-\frac{a_i}{\langle a \rangle_{37}}},$$

respectively, where the mass of drug in the cell, $m_i = \xi \ I'_i$ and/or the amount of radioactivity in the cell $a_i = \kappa \ I'_i$. The constants $\xi$ and $\kappa$ represent the slopes of plots of $<m>$ and $<a>$ versus $<I>_{net}$, respectively. These probabilities would be independent of flow cytometry hardware and instrument settings.

Not specifically addressed are the underlying reasons why the experimental and Monte Carlo derived clonogenic survival curves deviate most from those for an average concentration of agent at the higher concentrations. Although not wishing to be bound by any theory, in the realm of chemotherapy, this is often ascribed to resistant subpopulations that may express high levels of the multidrug resistant protein MDR1. One function of this protein is to facilitate the active removal of toxins from the cell, thereby foiling its therapeutic intent. Low cellular uptake by some cells within a population is also especially important for receptor-targeted agents such as radiolabeled antibodies used for radioimmunotherapy. The number of receptors on a given cell can vary widely over a cell population such that sublethal activity may be taken up by a subpopulation. The flow cytometry assisted Monte Carlo embodiment described above can be extremely useful in modeling the consequence of such nonuniformities, thereby reducing the level of experimental effort that is needed to optimize a therapy. Furthermore, a variety of other capabilities can be built into the model to account for other toxic insults to the cell population such as cross-dose received from radiations emitted by neighboring cells, and radiation- or chemically-induced bystander effects.

The use of flow cytometry to predict clonogenic survival using either agent-negative subpopulations of cells or flow cytometry-assisted Monte Carlo simulation has been demonstrated in the present disclosure. Generally, the fraction of apparently agent-negative cells cannot predict cell survival as determined by colony forming ability. However, it has been demonstrated that Monte Carlo simulation using cellular agent incorporation based on individual cell fluorescence intensity of therapeutic agents is a suitable predictor of cell survival. This flow cytomety based approach, which takes explicit account of the lognormal distribution of cellular uptake of the agents, offers a rapid means for determining treatment response on a cell-by-cell basis, and is invaluable in the selection of agents for the design of highly effective therapeutic cocktails that are capable of targeting the diversity in tumor cell populations. Such cocktails can be created not only for treatment of cancer, but also for infectious diseases and other diseases that may be amenable to targeted therapies. Furthermore, the single-cell Monte Carlo embodiment can be used to resolve difficulties encountered when attempting to predict biological response at the multicellular level using macroscopic mean agent doses.

The invention has been described via the specific embodiments and examples provided above which, however, do not limit the invention in any way.

What is claimed is:

1. A computer-implemented method of determining a dose of radiation when planning treatment for a patient with targeted radionuclide therapy, the method comprising:
   i. determining cellular incorporation of a radiopharmaceutical in a cell population on a cell-by-cell basis using a flow cytometer, wherein the flow cytometer measures fluorescence intensity;
   ii. displaying, by a computing device, a menu of a plurality of radiobiological parameter features associated with a dose of radiation;
   iii. receiving, by the computing device from a user, information pertaining to one or more radiobiological parameter features from the menu of features;
   iv. determining, by the computing device, a dose of radiation based upon the information pertaining to the one or more radiobiological parameter features by:
      performing a flow cytometry-assisted Monte Carlo simulation on said measured fluorescence intensities to predict surviving fractions of said cell population on a cell-by-cell basis under a plurality of dosing parameters, and
      using the determined surviving fractions to determine the dose of radiation.

2. The method of claim 1, further comprising, by the computing device:
   displaying a menu of a plurality of source radiation features; and
   receiving information pertaining to one or more of the source radiation features,
   wherein a source of radiation is selected from a radionuclide or a monoenergetic particle.

3. The method of claim 1 further comprising, by the computing device:
   displaying a menu of a plurality of cell source features; and
   receiving information pertaining to one or more of the cell source features, wherein information pertaining to one or more of the cell source features comprises a target volume in a cell.

4. The method of claim 1, further comprising, by the computing device:
displaying a menu of a plurality of cell geometry features; and
receiving information pertaining to one or more of the cell geometry features,
wherein information pertaining to one or more of the cell geometry features comprises one of the following:
a one dimension cell pair,
a cell population that resides on a plane, or
a three dimensional configuration of cells.

5. The method of claim 1, further comprising, by the computing device:
displaying a menu of a plurality of source radiation features; and
receiving information pertaining to one or more of the source radiation features,
wherein information pertaining to one or more of the source radiation features comprises select values for radiopharmaceutical agents.

6. The method of claim 1, wherein the cell population comprises a population of tumor cells from the patient for targeted radionuclide therapy treatment planning.

* * * * *